(12) United States Patent
Rahmo

(10) Patent No.: US 12,146,164 B2
(45) Date of Patent: Nov. 19, 2024

(54) COMPOSITIONS AND METHODS FOR USING SMALL MOBILE STEM CELLS

(71) Applicant: SMSBIOTECH, INC., Irvine, CA (US)

(72) Inventor: Abdulkader Rahmo, Glendale, CA (US)

(73) Assignee: SMSbiotech, Inc., San Marcos, CA (US)

( * ) Notice: Subject to any disclaimer, the term of this patent is extended or adjusted under 35 U.S.C. 154(b) by 1175 days.

(21) Appl. No.: 16/088,367

(22) PCT Filed: Mar. 27, 2017

(86) PCT No.: PCT/US2017/024357
§ 371 (c)(1),
(2) Date: Sep. 25, 2018

(87) PCT Pub. No.: WO2017/172638
PCT Pub. Date: Oct. 5, 2017

(65) Prior Publication Data
US 2020/0299649 A1    Sep. 24, 2020

Related U.S. Application Data

(60) Provisional application No. 62/314,874, filed on Mar. 29, 2016.

(51) Int. Cl.
| | |
|---|---|
| A61K 47/69 | (2017.01) |
| A61K 9/06 | (2006.01) |
| A61K 9/14 | (2006.01) |
| A61K 38/17 | (2006.01) |
| B01L 3/00 | (2006.01) |
| C12M 1/12 | (2006.01) |
| C12M 1/24 | (2006.01) |
| C12M 3/06 | (2006.01) |
| C12N 5/0775 | (2010.01) |
| C12P 21/00 | (2006.01) |

(52) U.S. Cl.
CPC .............. *C12N 5/0662* (2013.01); *A61K 9/06* (2013.01); *A61K 9/14* (2013.01); *A61K 38/17* (2013.01); *A61K 47/6955* (2017.08); *B01L 3/5027* (2013.01); *C12M 23/08* (2013.01); *C12M 23/16* (2013.01); *C12M 25/14* (2013.01); *C12P 21/00* (2013.01); *B01L 2200/10* (2013.01); *C12N 2513/00* (2013.01); *C12N 2533/90* (2013.01)

(58) Field of Classification Search
CPC .............................. C12N 5/0662; C12M 23/16
See application file for complete search history.

(56) References Cited

U.S. PATENT DOCUMENTS

| | | |
|---|---|---|
| 5,736,396 A | 4/1998 | Bruder |
| 5,750,397 A | 5/1998 | Tsukamoto |
| 2013/0236961 A1* | 9/2013 | Amit .................. C12N 5/0655 435/366 |

FOREIGN PATENT DOCUMENTS

| | | | |
|---|---|---|---|
| EP | 1617854 | 8/2014 | |
| JP | 2010-136655 A | 6/2010 | |
| JP | 2015-164406 A | 9/2015 | |
| WO | WO 2011/034106 A1 | 3/2011 | |
| WO | WO 2014/200940 | 12/2014 | |
| WO | WO-2014200940 A1 * | 12/2014 | ............. A61K 35/28 |

OTHER PUBLICATIONS

Thermo Fisher Scientific, Nalgene™ Single-Use PETG Erlenmeyer Flasks with Plain Bottom: Sterile, Mar. 5, 2013, https://www.thermofisher.com/order/catalog/product/4115-2800?SID=srch-srp-4115-2800, accessed on Sep. 26, 2023. (Year: 2013).*
Millipore Sigma, Cell Culture 96-Well Plate For Suspension Cells, (https://www.sigmaaldrich.com/US/en/search/cell-culture-96-well-plate-for-suspension-cells?focus=products&page=1&perpage=30&sort=relevance&term=cell%20culture%2096-well%20plate%20for%20suspension%20cells&type=product_name), Feb. 23, 2024 (Year: 2024).*
Rahmo et al. Introducing a Novel Human Stem Cell with Exceptional Characteristics: Small, Mobile Stem Cells (SMS) (2013), Journal of Life Sciences and Technologies, 1, pp. 56-61. (Year: 2013).*
Gui Fang Zhao et al: "Large-scale expansion of Wharton?s jelly derived mesenchymal stem cells on gelatin microbeads, with retention of self-renewal and multipotency characteristics and the capacity for enhancing skin wound healing", Stem Cell Research & Therapy, vol. 6, No. 1, Mar. 19, 2015 (Mar. 19, 2015), p. 38ff.
Jorge M Santos et al: "Three-dimensional spheroid cell culture of umbilical cord tissue-derived mesenchymal stromal cells leads to enhanced paracrine induction of wound healing", Stem Cell Research & Therapy, vol. 6, No. 1, May 9, 2015 (May 9, 2015), p. 90ff.
A. Rahmo: "Introducing a Novel Human Stem Cell with Exceptional Characteristics: Small, Mobile Stem Cells (SMS)", Journal of Life Sciences and Technologies, Jan. 1, 2013 (Jan. 1, 2013), pp. 56-61.

(Continued)

*Primary Examiner* — Kara D Johnson
*Assistant Examiner* — Maytee Marie Contes De Jesus
(74) *Attorney, Agent, or Firm* — Knobbe Martens Olson & Bear LLP

(57) ABSTRACT

Disclosed herein are small mobile stem (SMS) cells and methods of culturing, isolating, and using SMS cells. Also disclosed are methods of culturing SMS cells in an undifferentiated state for prolonged periods of time, and for using SMS cells for the production of a variety of molecules, including proteins, extracellular matrix (ECM) proteins, and the use of SMS cells in microfluidic devices.

10 Claims, 45 Drawing Sheets

(56) References Cited

OTHER PUBLICATIONS

Extended Search Report issued in European application No. 17776405.7, dated Sep. 24, 2019.
92(2014), p. 469-472.
Office Action issued in JP application No. 2019-503387, dated Mar. 2, 2021.
Ali et al. (2012) 2 (1) Stem Cell Discovery 15-23.
Caplan et al. (2001) 7 Trends Mol Med 259-64.
Danova et al. (2012) 7 PLoS One e34899.
Dawn et al. (2008) 26 Stem cells 1646-55.
Hussain et al. Biochm Eng J, 77(100), 2013, 246-257.
Kassis et al. Bone Marrow Transplantation, 37(10), 2006, 967-976.
Körbling et al. (2002) 346 N Engl J Med 738-746.
Kucia et al. (2008) 26 Stem Cells 2083-2092.
Rajamani et al. Cell Transplantation, 24(3), 2015, 493-507.
Ratajczak et al., Circulation Res, 120(1), 2017, 166-178.
Schwartz et al. (2000) 109 J Clin Invest 1291-1302.
Stamm et al. (2003) 361 Lancet 45-46.
Truong, Connector Series: SMSbiotech, Oct. 11, 2016.
Yoo et al. (1998) 80 J Bone Joint Surg Am 1745-57.
Young et al. (1998) 16 J Orthop Res 406-13.
Zuba-Surma et al. (2011) 15 J Cell Mol Med 1319-28.
International Search Report in application No. PCT/US2017/024357, mailed Jun. 22, 2017.

\* cited by examiner

Formation of membranous Extracellular Matrix

COMPOSITIONS AND METHODS FOR USING SMALL MOBILE STEM CELLS

CROSS-REFERENCE TO RELATED APPLICATIONS

This application is a U.S. National Phase Application of PCT International Application Number PCT/US2017/024357, filed on Mar. 27, 2017, designating the United States of America and published in the English language, which is an International Application of and claims the benefit of priority to U.S. Provisional Application No. 62/314,874 filed Mar. 29, 2016, the disclosures of which are hereby expressly incorporated by reference in their entireties.

FIELD OF THE INVENTION

The present disclosure relates generally to methods and compositions of culturing, isolating, and using a population of stem cells identified as small mobile stem (SMS) cells. More particularly, the present disclosure relates to methods of culturing SMS cells in an undifferentiated state for prolonged periods of time, and for using SMS cells for the production of a variety of molecules, including extracellular matrix (ECM) proteins, and the use of SMS cells in microfluidic devices.

BACKGROUND

Stem cells are immature, unspecialized cells that are capable of renewing themselves for extended periods through cell division. Under certain conditions, they differentiate into mature, functional cells.

The use of stem cells and stem cell derivatives is currently of great interest to medical research, particularly for the prospects of providing reagents for treating tissue which has been damaged by various causes such as genetic disorders, injuries, and/or disease processes. Stem cells are capable of asymmetric division, can replenish themselves, and can differentiate into various cell types. In theory, stem cells could replace any damaged cells and tissues of an organism of choice. This process of regeneration is inherently present, to various extents, in all living multicellular organisms. Human organs, however, vary greatly in their potential for regeneration and repair. Many vital organs such as the heart and the brain show little capacity for repair after injury.

Significant effort has been concentrated at isolating and identifying human stem cells from a number of different tissues for use in regenerative medicine. Because bone marrow transplants have been successfully performed for decades, such efforts were concentrated initially on identifying stem cells in bone marrow. U.S. Pat. No. 5,750,397 discloses the isolation and growth of human hematopoietic stem cells that are reported to be capable of differentiating into lymphoid, erythroid, and myelomonocytic lineages. U.S. Pat. No. 5,736,396 discloses methods for lineage-directed differentiation of isolated human mesenchymal stem cells under the influence of appropriate growth and/or differentiation factors. The derived cells can then be introduced into a host for mesenchymal tissue regeneration or repair.

Another area of interest was the use of embryonic stem (ES) cells. These stem cells have been shown in mice to have the potential to differentiate into all the different cell types of the animal. Mouse ES cells are derived from cells of the inner cell mass of early mouse embryos at the blastocyst stage, and other pluripotent and/or totipotent cells have been isolated from germinal tissue (e.g., primordial germ cells; PGCs). Unfortunately, the development of human ES (hES) cells was not as successful.

In addition to the ethical controversy inherent to the use of hES cells, significant other challenges face the use of ES cells or other pluripotent cells for regenerative therapy. The control of growth and differentiation of the cells into the particular cell type required for treatment of a subject is difficult. There have been several reports of the effect of growth factors on the differentiation of ES cells. For example, Schuldiner et al. report the effects of eight growth factors on the differentiation of cells into different cell types from hES cells (Schuldiner et al. (2000) 97 PNAS USA 1 1307-1 1312). As disclosed therein, after initiating differentiation through embryoid body-like formation, the cells were cultured in the presence of bFGF, TGFpi, activin-A, BMP-4, HGF, EGF, PNGF, or retinoic acid. Each growth factor had a unique effect on the differentiation pathway, but none of the growth factors directed differentiation exclusively to one cell type. Also the current strategies for isolating ES cell lines, particularly human ES cell lines, preclude isolating the cells from a subject and reintroducing them into the same subject (autologous transfer). The use of a subject's own cells would obviate the need for adjunct immunosuppressive therapy, maintaining thereby full competency of the immune system.

Adult human stem cells such as mesenchymal stem cells (MSCs) have been shown to have the potential to differentiate into several lineages including bone (Haynesworth et al. (1992) 13 Bone 81-88), cartilage (Mackay et al. (1998) 4 Tissue Eng 415-28; Yoo et al. (1998) 80 J Bone Joint Surg Am 1745-57), adipose tissue (Pittenger et al. (2000) 251 Curr Top Microbiollmmunol 3-11), tendon (Young et al. (1998) 16 J Orthop Res 406-13), muscle, and stroma (Caplan et al. (2001) 7 Trends Mol Med 259-64).

Another population of cells, multipotent adult progenitor cells (MAPCs), has also been purified from bone marrow (BM; Reyes et al. (2001) 98 Blood 2615-2625; Reyes & Verfaillie (2001) 938 Ann NY AcadSci 231-235). These cells have been shown to be capable of expansion in vitro for more than 100 population doublings. MAPCs have also been shown to be able to differentiate under defined culture conditions into various mesenchymal cell types (e.g., osteoblasts, chondroblasts, adipocytes, and skeletal myoblasts), endothelium, neuroectoderm cells, and more recently, into hepatocytes (Schwartz et al. (2000) 109 J Clin Invest 1291-1302).

In vivo experiments in humans demonstrated that transplantation of $CD34^+$ peripheral blood (PB) stem cells led to the appearance of donor-derived hepatocytes (Korbling et al. (2002) 346 N Engl J Med 738-746), epithelial cells (Korbling et al. (2002) 346 N Engl J Med 738-746), and neurons (Hao et al. (2003) 12 J Hematother Stem Cell Res 23-32). Additionally, human BM-derived cells have been shown to contribute to the regeneration of infarcted myocardium (Stamm et al. (2003) 361 Lancet 45-46). Currently Adult stem cells such as mesenchymal stem cells are widely investigated in clinical trials for a variety of diseases (Ali et al. (2012) 2 (1) Stem Cell Discovery 15-23).

Very small embryonic like stem cells (VSELs) is a rare cell population that possess very primitive morphology and express pluripotent stem cell markers (e.g., Oct4, Nanog, and SSEA-4) as well as the surface phenotype Scal+/CD133+Lin− CD 45− in mice/humans. VSELs can be mobilized into peripheral blood following acute myocardial infarction (Kucia et al. (2008) 26 Stem Cells 2083-2092), and is reported to improve heart function and alleviate cardiac remodeling (Dawn et al. (2008) 26 Stem cells 1646-55; Zuba-Surma et al. (2011) 15 J Cell Mol Med 1319-28).

Attempts to culture VSEL were unsuccessful, which led some researchers to question their very presence in human (Danova et al. (2012) 7 PLoS One e34899). Other researchers such as Gu et al. (2013) found also that it is very difficult expand or culture human VSELs in vitro using general culture conditions. Thus it is not clear yet whether these cells are merely developmental remnants found in the adult tissue that cannot be harnessed effectively for regeneration or that they represent real stem cell population suitable for regenerative medicine.

Generally, obtaining adult stem cells from tissues other than bone marrow continues to be difficult; especially for the case of providing sufficient cells for autologous transfer. Non autologous transfer of cells implanting stem cells to others is on the other hand prone to problems associated with an immune rejection reaction and would require an adjunct immune suppressive therapy. Ex vivo culturing of adult stem cells is used as an alternative for providing sufficient cells. However adult stem cells are relatively sensitive to incubation conditions and if successfully cultured require strict control of these conditions (Bhattacharya et al, (2009) Frontiers of cord blood science, Springer-Verlag London Limited).

Small mobile stem (SMS) cells have recently been isolated and characterized. WO 2014/200940 characterizes SMS cells as adherent cells that are from 4.5 to 5.5 μm in diameter, and are obtained from sources such as umbilical cord, peripheral blood, bone marrow, or solid tissue. Furthermore, SMS cells are highly mobile.

Although the promise of SMS cells for basic scientific research pharmacology and regenerative medicine is remarkable, the exploitation of SMS cells for most applications depends upon further development. Improved control of the growth of undifferentiated SMS cells and the development of methods and tools which direct the differentiation and generate pure cultures of mature functional cells of a specific type are required.

ECM is a structure, scaffold, or platform made up of a chemically or biochemically defined material to which various cells (e.g. dermal, muscle, nerve, connective tissue, fascia, dura or peritoneum) of higher vertebrates can adhere to and multiply without causing toxicity or inhibition of cell replication. Components of ECM can include proteoglycans, glycoproteins, non-proteoglycan saccharides, and fibers.

From a physiological standpoint, ECM is essential for regrowth and healing of tissue. In human fetuses, for example, the ECM works with stem cells to grow and regrow all parts of the human body, and fetuses can regrow anything that gets damaged in the womb. However, after reaching full development, the ECM stops functioning.

ECM is also useful in medical applications, where it is used applications of injury repair and tissue engineering by preventing the immune system from responding to the injury with inflammation. In addition, the ECM facilitates the surrounding cells to repair the tissue instead of forming scar tissue. In these cases, the ECM is often extracted from a source, such as from pig bladders, decellularized, and used in the given application. Such applications include the treatment of ulcers, reconstructive surgery, and injury repair. ECM powders can also be used for tissue engineering.

ECM proteins are commonly used in cell culture systems to maintain stem and precursor cells in an undifferentiated state during cell culture and function to induce differentiation of epithelial, endothelial and smooth muscle cells in vitro. Extracellular matrix proteins can also be used to support 3D cell culture in vitro for modeling tumor development.

There continues to be a need in cell therapy for new approaches to maintain populations of transplantable cells in an undifferentiated state that are suitable for a variety of applications. In addition, there is a need to be able to produce ECM proteins in culture, in a simple, inexpensive, and efficient manner.

SUMMARY

The present disclosure shows that small mobile stem (SMS) cells can be maintained in an undifferentiated state for extended periods of time under proper conditions. As a result, the SMS cells can be conveniently cultured over extended periods until required for differentiation or expression of various molecules.

Accordingly, the present disclosure relates to methods of culturing a population of SMS cells under conditions that maintain the SMS cells in an undifferentiated state. The method includes culturing in suspension an isolated population of SMS cells in a growth medium preferably under conditions that maintain the isolated population of SMS cells in an undifferentiated state. In some embodiments, the SMS cells are cultured in a growth medium that is a high sugar basal medium. In some embodiments, the high sugar basal medium further includes calf serum, insulin, or both. In some embodiments, the isolated population of SMS cells is cultured at 37° C. and 5% $CO_2$. Non-adherence of the SMS cells to surfaces necessitates, for example, a surface like polypropylene plastic instead of polystyrene.

In some embodiments, the isolated population of SMS cells are isolated from umbilical cord blood, peripheral blood, bone marrow, or a solid tissue. In some embodiments, the solid tissue is placenta, liver, heart, brain, kidney, or tissue from the gastrointestinal tract. The population of SMS cells can be isolated from the peripheral blood of humans, primates, domestic animals, such as cats and dogs, and mammals such as camels, horses, pigs, and cattle.

In some embodiments, the method of culturing SMS cells encoding a gene product further includes isolating or purifying the gene product.

In some embodiments, the isolated population of suspended SMS cells is separated from adherent cells. In some embodiments, the method further includes removing clumps of differentiated cells by low-speed centrifugation. In some embodiments, the isolated population of suspended SMS cells is isolated by differential centrifugation.

In some embodiments, the method of culturing SMS cells in an undifferentiated state further includes isolating or passaging the isolated population of SMS cells by centrifugation or filtration after said culturing. In some embodiments, the centrifugation is carried out at 3000 g, 3500 g, 4000 g, 4100 g, 4200 g, 4300 g, 4500 g, or 5000 g or by centrifugation at a speed that is within a range defined by any two of the aforementioned speeds for a time equivalent to 15 minutes at 4200 g. In some embodiments, the filtration is carried out using differential filtration, wherein a filter having larger pores is used initially, followed by filters having progressively smaller pores. In some embodiments, the filter has pores of around 3-5 μm to capture the SMS cells. In particular, undifferentiated SMS cells do not clump in suspension and are therefore readily subject to filtration isolation.

In some embodiments, the population of SMS cells is introduced in a flask, container, chamber, channel, tube, vessel, niche, or bioreactor, optionally with movement and/or circulation of a medium. In some embodiments, the SMS cells are grown in the flask, container, chamber, channel, tube, vessel, niche, or bioreactor. In some embodiments, the SMS cells are seeded in the flask, container, chamber, channel, tube, vessel, niche, or bioreactor. In some embodiments, the SMS cells are placed in the flask, container, chamber, channel, tube, vessel, niche, or bioreactor, and frozen or stored for subsequent use. In some embodiments, the surface of the flask, container, chamber, channel, tube, vessel, niche, or bioreactor is pretreated. In some embodiments, the pretreatment of the surface of the flask, container, chamber, channel, tube, vessel, niche, or bioreactor includes etching the surface with one or more predetermined geometric shape, wherein the one or more geometric shape acts as a guide for the SMS cells. In some embodiments, the etching of the surface coordinates, directs, or otherwise signals the growth and organization of the SMS cells. In some embodiments, the one or more geometric shape is a line, a curve, a web, a groove, a ridge, or other shape. In some embodiments, the one or more geometric shape is smooth or rough.

In some embodiments, the channel is a microfluidic channel. In some embodiments, the microfluidic channel is incorporated into a microfluidic device. In some embodiments, the microfluidic device is a microfluidic chip. In some embodiments, the microfluidic chip is a lab-on-a-chip device that integrates one or more laboratory functions on a single chip. In some embodiments, the microfluidic device is a cell-on-a-chip, tissue-on-a-chip, or organ-on-a-chip device that stimulates the activities, mechanics, and physiological response of cells, tissues, and entire organs and organ systems.

In some embodiments, the method of culturing SMS cells further includes transfecting an isolated population of SMS cells with a gene that encodes a gene product, preferably a gene that encodes a protein, such as, a growth factor, a cytokine, a peptide hormone, a protein hormone, an enzyme, a protein fragment, or an extracellular matrix protein.

In some embodiments, the gene product includes, for example, an epidermal growth factor (EGF), a platelet derived growth factor (PDGF), a fibroblast growth factor (FGF and bFGF), a transforming growth factor (TGF-α and TGF-β 1, 2, & 3), a vascular endothelial growth factor (VEGF), a hepatocyte growth factor (HGF), a keratinocyte growth factor (KGF), a nerve growth factor (NGF), erythropoietin (EPO), an insulin-like growth factors (IGF-I and IGF-II), an interleukin cytokine (IL-1α, IL-1β, IL-2, IL-3, IL-4, IL-5, IL-6, IL-7, IL-8, IL-9, IL-10, IL-11, IL-12, IL-13), an interferon (IFN-α, IFN-β, and IFN-γ), a tumor necrosis factor (TNFα and TNF-β), a colony stimulating factor (GM-CSF and M-CSF), insulin, parathyroid hormone, collagenase, collagen, elastin, laminin, agrin, nidogen, and entactin or variations and/or combinations thereof.

Some embodiments concern a method of using an isolated population of small mobile stem (SMS) cells for the production of a molecule, including providing an isolated population of SMS cells and inducing the isolated population of SMS cells to produce the molecule.

In some embodiments, the molecule is a protein, such as a growth factor, a cytokine, a peptide hormone, a protein hormone, or an extracellular matrix protein.

In some embodiments, the molecule includes, for example, an epidermal growth factor (EGF), a platelet derived growth factor (PDGF), a fibroblast growth factor (FGF and bFGF), a transforming growth factor (TGF-α and TGF-β 1, 2, & 3), a vascular endothelial growth factor (VEGF), a hepatocyte growth factor (HGF), a keratinocyte growth factor (KGF), a nerve growth factor (NGF), erythropoietin (EPO), an insulin-like growth factors (IGF-I and IGF-II), an interleukin cytokine (IL-1α, IL-1β, IL-2, IL-3, IL-4, IL-5, IL-6, IL-7, IL-8, IL-9, IL-10, IL-11, IL-12, IL-13), an interferon (IFN-α, IFN-β, and IFN-γ), a tumor necrosis factor (TNFα and TNF-β), a colony stimulating factor (GM-CSF and M-CSF), insulin, parathyroid hormone, collagenase, collagen, elastin, laminin, agrin, nidogen, and entactin or variations and/or combinations thereof.

In some embodiments, the protein is coagulation factor XIII A chain, apolipoprotein E, anithrombin III, bone morphogenic protein 1, vitronectin, acidic leucine-rich nuclear phosphoprotein 32 family member A (ANP32A), calcineurin-like phosphoesterase, peptidyl-prolyl cis-trans isomerase, β-enolase, fermitin family homolog 1, microtubule-associated protein RP/EB (MAPRE1), a heat shock protein, LIM and senescent cell antigen-like-containing domain protein 1 (LIMS1), myosin regulatory protein, profilin-1, glycogen phosphorylase, flavin reductase, mitogen activated protein kinase, protein phosphatase, tubulin, chloride intracellular channel proteins, wings apart-like protein homolog (WAPAL), cell division control proteins, osteopontin, BPI fold-containing, elongation factor, plasminogen, aldo-keto reductase, or keratin.

In some embodiments, the cells are induced with one or more chemical inducers. In some embodiments, the one or more chemical inducers is dimethyl sulfoxide (DMSO), butylated hydroxyanisole, β-mercaptoethanol, ascorbic acid-2-phosphate, dexamethasone, β-glycerophosphate, dimethylsulfoxide, insulin, isobutylmethylxanthine, or indomethacin, or combinations thereof. In some embodiments, the chemical inducers comprise dexamethasone present in an amount of 0.1 μM, ascorbic acid-2-phosphate present in an amount of 0.05 mM, and β-glycerophosphate present in an amount of 10 mM.

Some embodiments concern a method of differentiating an isolated population of undifferentiated small mobile stem (SMS) cells, including providing an isolated population of undifferentiated SMS cells, and contacting the isolated population of undifferentiated SMS cells with one or more chemical inducers, wherein the isolated population of undifferentiated SMS cells are induced to differentiate into one or more differentiated cell types, tissues, tissue like structures, organoids, or organs.

In some embodiments, the one or more chemical inducers include, for example ascorbic acid 2 phosphate, dexamethasone, beta glycerophosphate, dimethylsulfoxide, and butylated hydroxyanisole.

Some embodiments concern a method of applying small mobile stem (SMS) cells as a substrate for the process of generating spatially-controlled cell patterns using a 3D bioprinting device including providing an isolated population of undifferentiated SMS cells, and generating a spatially-controlled cell pattern using a 3D bioprinting apparatus and said isolated population of undifferentiated SMS cells as a substrate.

In some embodiments, the 3D bioprinting device includes, for example, BioBot1®, 3D-Bioplotter®, 3DS Alpha®, or 3Dynamic Omega®.

Some embodiments concern a method of producing an extracellular matrix (ECM) protein in culture using small mobile stem (SMS) cells, the method including providing an isolated population of undifferentiated SMS cells and inducing said isolated population of undifferentiated SMS cells to produce an ECM protein.

In some embodiments, the isolated population of undifferentiated SMS cells are induced to produce an ECM protein by contacting said isolated population of undifferentiated SMS with one or more chemical inducers of ECM protein production such as, a hedgehog inhibitor, a TGF/BMP activator, ascorbic acid, ascorbic acid 2 phosphate, serum present in the growth medium, and/or polystyrene.

In some embodiments, the produced ECM protein includes one or both of suspended ECM protein and attached ECM protein. In some embodiments, the method of producing ECM protein further includes isolating the suspended ECM protein e.g., by centrifugation, precipitation, or filtration. In some embodiments, the method of producing ECM protein further includes isolating the attached ECM protein e.g., by scraping the culturing vessel. In some embodiments, the method of isolating ECM components or proteins from SMS cells further includes lysing or removing any remaining cells from the isolated ECM. In some embodiments, the ECM components include, for example, agrin, nidogen, cadherins, clathrin, collagen, defensin, elastin, entactin, fibrillin, fibronectin, keratin, laminin, microtubule-actin cross-linking factor 1, SPARC-like protein, nesprin (nesprin-1, nesprin-2, nesprin-3), fibrous sheath-interacting protein, myomesin, nebulin, plakophilin, integrin, talins, exportins, transportin, tenascin, perlecan, sortilin-related receptor, tensin, titin, total protein, and/or a fragment of any one or more of the aforementioned proteins. In some embodiments, the method of isolating ECM protein from SMS cells further includes modifying the ECM protein e.g., by freezing, lyophilizing, cross-linking, drying and/or pulverizing the isolated ECM. In some embodiments, the modified ECM protein is suitable for promoting cell growth or cell differentiation in vitro or in vivo.

In some embodiments, the method of isolating ECM protein from SMS cells includes culturing the isolated population of undifferentiated SMS cells on a scaffold. In some embodiments, the scaffold is a porous and/or implantable scaffold such as, for example, a scaffold including a native decellularized bone, carbon, porous carbon, activated carbon, a soft decellularized collagen, a decellularized organ, chitosan, demineralized bone matrix, membrane and/or barrier allographs, or a combination thereof. In some embodiments, the scaffold is synthetic, semi-synthetic, or native.

Some embodiments concern a method for the production of a soft tissue, including culturing an isolated population of undifferentiated SMS cells in the presence of peripheral blood, forming a gel-like structure, freezing the gel-like structure, thawing the frozen gel-like structure, and culturing the thawed gel-like structure, wherein the thawed gel-like structure forms a soft tissue-like structure. In some embodiments, the gel-like structure is frozen at −20° C.

Some embodiments provided herein relate to a composition comprising one or more extracellular matrix (ECM) proteins obtained from a culture of small mobile stem (SMS) cells. In some embodiments, the one or more ECM proteins is denatured. In some embodiments, the one or more ECM proteins is modified by acetylation, acylation, carboxylation, glycosylation, hydroxylation, lipidation, methylation, pegylation, phosphorylation, prenylation, sulfation, or ubiquitination. In some embodiments, the one or more ECM proteins is selected from the group consisting of agrin, nidogen, cadherins, clathrin, collagen, defensin, elastin, entactin, fibrillin, fibronectin, keratin, laminin, microtubule-actin cross-linking factor 1, SPARC-like protein, nesprin (nesprin-1, nesprin-2, nesprin-3), fibrous sheath-interacting protein, myomesin, nebulin, plakophilin, integrin, talins, exportins, transportin, tenascin, perlecan, sortilin-related receptor, tensin, titin, total protein, and/or a fragment of any one or more of the aforementioned proteins. In some embodiments, the one or more ECM proteins comprise a molecule that inhibits microbial growth, such as a bacteria and/or fungi, inhibiting compound. In some embodiments, the microbial growth inhibiting compound is an anti-microbial protein selected from the group consisting of collectin, C-type lectin family 4, septin 12, and pancreatic ribonuclease. In some embodiments, the composition is formulated as an aerosol, a cream, an emulsion, a foam, a foamable liquid, a gel, a lotion, an ointment, a paste, a salve, a serum, a solution, or a spray.

Some embodiments provided herein relate to a system for wound healing. In some embodiments, the system for wound healing comprises a wound dressing material. In some embodiments, the wound dressing material comprises a composition that comprises an extracellular matrix (ECM) protein prepared or derived from SMS cells. In some embodiments, the wound dressing material comprises a bandage, a wipe, a gauze, a sponge, a mesh, a pad, an adhesive bandage, or an absorbent wound dressing material. In some embodiments, the ECM protein included in the system for wound healing or the wound dressing material is selected from the group consisting of agrin, nidogen, cadherins, clathrin, collagen, defensin, elastin, entactin, fibrillin, fibronectin, keratin, laminin, microtubule-actin cross-linking factor 1, SPARC-like protein, nesprin (nesprin-1, nesprin-2, nesprin-3), fibrous sheath-interacting protein, myomesin, nebulin, plakophilin, integrin, talins, exportins, transportin, tenascin, perlecan, sortilin-related receptor, tensin, titin, total protein, and/or a fragment of any one or more of the aforementioned proteins.

Some embodiments provided herein relate to a method of treating or ameliorating a wound. In some embodiments, the method of treating or ameliorating a wound comprises contacting a wound of a subject with a composition comprising one or more ECM proteins obtained or derived from SMS cells. Preferably, the ECM proteins obtained or derived from said SMS cells comprise an antimicrobial compound or said ECM proteins obtained or derived from said SMS cells exhibit or possess anti-microbial activity, such as, antiviral, antibacterial, or anti-fungal activity. In some embodiments, the method of treating or ameliorating a wound comprises contacting a wound of a subject with a system that comprises a wound dressing material and said wound dressing material comprises one or more ECM proteins obtained or derived from SMS cells, preferably, ECM proteins obtained or derived from said SMS cells, which comprise an antimicrobial compound, such as, antiviral, antibacterial, or anti-fungal compound.

Some embodiments provided herein relate to a method of producing proteins from SMS cells. In some embodiments, the method comprises culturing an isolated population of undifferentiated small mobile stem (SMS) cells in growth media in a vessel. In some embodiments, the method of producing proteins from SMS cells comprises inducing said SMS cells to produce a protein. In some of these methods, the cells are cultured in the absence of $CO_2$. In some embodiments, the cells are cultured in the absence of an antibiotic. In some embodiments, the cells are grown in culture media in a container comprising a volume of between 300 mL and 500 L, such as 300 mL, 500 mL, 1 L, 5 L, 10 L, 20 L, 30 L, 40 L, 50 L, 60 L, 70 L, 80 L, 90 L, 100 L, 200 L, 300 L, 400 L, or 500 L or in a volume that is within a range defined by any two of the aforementioned volumes. In some methods of producing a protein, the SMS cells produce or are induced to produce coagulation factor XIII A chain, apolipoprotein E, anithrombin III, bone morphogenic protein 1, vitronectin, acidic leucine-rich nuclear phosphoprotein 32 family member A (ANP32A), calcineurin-like phosphoesterase, peptidyl-prolyl cis-trans isomerase, O-enolase, fermitin family homolog 1, microtubule-associated protein RP/EB (MAPRE1), heat shock proteins, LIM and senescent cell antigen-like-containing domain protein 1 (LIMS1), myosin regulatory protein, profilin-1, glycogen phosphorylase, flavin reductase, mitogen activated protein kinase, protein phosphatase, tubulin, chloride intracellular channel proteins, wings apart-like protein homolog (WAPAL), cell division control proteins, osteopontin, BPI fold-containing, elongation factor, plasminogen, aldo-keto reductase, or keratin, or an extracellular matrix protein (ECM), or a fragment of any one or more of the aforementioned proteins. In some embodiments, the ECM protein that is produced by said SMS cells with or without induction is agrin, nidogen, cadherins, clathrin, collagen, defensin, elastin, entactin, fibrillin, fibronectin, keratin, laminin, microtubule-actin cross-linking factor 1, SPARC-like protein, nesprin (nesprin-1, nesprin-2, nesprin-3), fibrous sheath-interacting protein, myomesin, nebulin, plakophilin, integrin, talins, exportins, transportin, tenascin, perlecan, sortilin-related receptor, tensin, titin, total protein, and/or a fragment of any one or more of the aforementioned proteins. In some embodiments, the vessel used to expand the SMS cells promotes or is configured to promote the growth of SMS cells in suspension. In some embodiments, the vessel is a polypropylene vessel, or a pretreated siliconized vessel, or a vessel that is configured to promote the growth of SMS cells in suspension (e.g., a flask or bioreactor having a circulation of media, such as that generated by stirring, shaking, or swirling). In some embodiments, the vessel promotes SMS cell adherence. In some embodiments, the SMS cells are induced with one or more chemical inducers. In some embodiments, the one or more chemical inducers is dimethyl sulfoxide (DMSO), butylated hydroxyanisole, β-mercaptoethanol, ascorbic acid-2-phosphate, dexamethasone, β-glycerophosphate, dimethylsulfoxide, insulin, isobutylmethylxanthine, or indomethacin, or any combinations thereof. In some embodiments, the chemical inducers comprise dexamethasone present in an amount of 0.1 µM, ascorbic acid-2-phosphate present in an amount of 0.05 mM, and β-glycerophosphate present in an amount of 10 mM.

Some embodiments provided herein relate to a method of producing a tubule or vessel structure comprising culturing endothelial cells with SMS-derived extracellular matrix (ECM). In some embodiments, the endothelial cells migrate into and interact with said SMS-derived ECM thereby producing a tubule or vessel structure.

Some embodiments provided herein relate to a method of selecting an agent or compound that induces, promotes, or contributes to vessel formation, angiogenesis, or arteriogenesis by a cell population. In some embodiments, the method includes providing extracellular matrix (ECM) produced from SMS cells as described herein. In some embodiments, the method includes contacting said ECM produced from said SMS cells with a first cell population comprising cells capable of vessel formation, angiogenesis, or arteriogenesis, such as endothelial cells. In some embodiments, the method includes contacting said first cell population that is in contact with said ECM with an agent or compound. In some embodiments, the method includes determining whether said agent or compound induces, promotes, or contributes to vessel formation, angiogenesis, or arteriogenesis in said first cell population by comparing the quality or quantity of vessel formation, angiogenesis, or arteriogenesis in said first cell population in contact with said ECM after contact with said agent or compound with a second cell population, preferably of the same cell type as the first cell population, grown in said ECM in the absence of contact with said agent or compound. In some embodiments, the an increase in quantity or quality of vessel formation, angiogenesis, or arteriogenesis in said first cell population as compared to said second cell population identifies said agent or compound as one for selection as an agent or compound that induces, promotes, or contributes to vessel formation, angiogenesis, or arteriogenesis by a cell population.

Accordingly, some aspects of the present invention relate to the following alternatives:

1. A method of culturing a population of small mobile stem (SMS) cells, comprising:
    culturing an isolated population of SMS cells in a growth medium, in a suspension, preferably, under conditions that maintain the isolated population of SMS cells in a suspension and/or in an undifferentiated state.

2. The method of alternative 1, wherein the growth medium is a high sugar basal medium.

3. The method of alternative 2, wherein the high sugar basal medium further comprises calf serum, insulin, or combinations thereof.

4. The method of any one of alternatives 1-3, wherein the isolated population of SMS cells are cultured at 37° C. and 5% $CO_2$.

5. The method of any one of alternatives 1-4, wherein the isolated population of SMS cells are cultured in a vessel configured to prevent adherence of the SMS cells, such as a polypropylene vessel or tube.

6. The method of anyone of alternatives 1-5, wherein the isolated population of SMS cells are isolated from umbilical cord blood, peripheral blood, bone marrow, or a solid tissue such as, e.g., from the peripheral blood of humans, primates, domestic animals, such as cats and dogs, and mammals such as camels, horses, pigs, and cattle.

7. The method of alternative 6, wherein the solid tissue is placenta, liver, heart, brain, kidney, or tissue from the gastrointestinal tract.

8. The method of anyone of alternatives 1-7, wherein the population of SMS cells is introduced in a flask, container, chamber, channel, tube, vessel, niche, or bioreactor, optionally with movement and/or circulation of the medium that the isolated population of SMS cells are grown in.

9. The method of alternative 8, further comprising pretreating a surface of the flask, container, chamber, channel, tube, vessel, niche, or bioreactor.

10. The method of alternative 9, wherein the pretreatment comprises etching the surface with a predetermined geometric shape, wherein the geometric shape acts as a guide to organize the SMS cells.

11. The method of alternative 10, wherein the geometric shape is a line, web, groove, ridge, or other shape.

12. The method of alternative 8, wherein the channel is a microfluidic channel incorporated in a microfluidic device.

13. The method of anyone of alternatives 1-8, further comprising isolating or passaging the isolated population of SMS cells by centrifugation or filtration after said culturing.

14. The method of anyone of alternatives 1-9, further comprising transfecting the isolated population of SMS cells with a gene that encodes a gene product, preferably a gene that encodes a protein, such as, a growth factor, a cytokine, a peptide hormone, a protein hormone, an enzyme, a protein fragment, or an extracellular matrix protein.

15. The method of alternative 14, wherein gene product is selected from the group consisting of insulin growth factor 2, interleukin 6, insulin, parathyroid hormone, collagenase, collagen, elastin, laminin, agrin, nidogen, and entactin.

16. The method of alternative 14, further comprising isolating or purifying the gene product.

17. The method of anyone of alternatives 1-16, wherein the isolated population of suspended SMS cells are separated from adherent cells.

18. The method of anyone of alternative 1-17, wherein the isolated population of SMS cells are cultured at 37° C. and 5% $CO_2$.

19. The method of anyone of alternatives 1-18, further comprising removing clumps of differentiated cells by low-speed centrifugation.

20. The method of anyone of alternatives 1-19, wherein the isolated population of suspended SMS cells are isolated by differential centrifugation.

21. A method of using an isolated population of small mobile stem (SMS) cells for the production of a molecule, the method comprising:
providing an isolated population of SMS cells, e.g., the isolated population of suspended SMS cells obtained by the methods of anyone of alternatives 1-20; and
inducing the isolated population of SMS cells to produce the molecule.

22. The method of alternative 21, wherein the molecule is a protein, such as a growth factor, a cytokine, a peptide hormone, a protein hormone, or an extracellular matrix protein.

23. The method of anyone of alternatives 21 or 22, wherein the molecule is selected from the group consisting of insulin growth factor 2, interleukin 6, insulin, parathyroid hormone, collagenase, collagen, elastin, laminin, agrin, nidogen, and entactin.

24. The method of any one of alternatives 21-23, wherein the protein is coagulation factor XIII A chain, apolipoprotein E, anithrombin III, bone morphogenic protein 1, vitronectin, acidic leucine-rich nuclear phosphoprotein 32 family member A (ANP32A), calcineurin-like phosphoesterase, peptidyl-prolyl cis-trans isomerase, β-enolase, fermitin family homolog 1, microtubule-associated protein RP/EB (MAPRE1), heat shock proteins, LIM and senescent cell antigen-like-containing domain protein 1 (LIMS1), myosin regulatory protein, profilin-1, glycogen phosphorylase, flavin reductase, mitogen activated protein kinase, protein phosphatase, tubulin, chloride intracellular channel proteins, wings apart-like protein homolog (WAPAL), cell division control proteins, osteopontin, BPI fold-containing, elongation factor, plasminogen, aldo-keto reductase, or keratin.

25. The method of any one of alternatives 21-24, wherein the cells are induced with one or more chemical inducers.

26. The method of alternative 25, wherein the one or more chemical inducers is dimethyl sulfoxide (DMSO), butylated hydroxyanisole, β-mercaptoethanol, ascorbic acid-2-phosphate, dexamethasone, β-glycerophosphate, dimethylsulfoxide, insulin, isobutylmethylxanthine, or indomethacin, or combinations thereof.

27. The method of any one of alternatives 25-26, wherein the chemical inducers include dexamethasone present in an amount of 0.1 µM, ascorbic acid-2-phosphate present in an amount of 0.05 mM, and β-glycerophosphate present in an amount of 10 mM.

28. A method of differentiating an isolated population of undifferentiated small mobile stem (SMS) cells, the method comprising:
providing an isolated population of undifferentiated SMS cells, e.g., the isolated population of suspended SMS cells obtained by the methods of anyone of alternatives 1-20; and
contacting the isolated population of undifferentiated SMS cells with one or more chemical inducers, wherein the isolated population of undifferentiated SMS cells are induced to differentiate into one or more differentiated cell types, tissues, tissue like structures, organoids, or organs.

29. The method of alternative 28, wherein the one or more chemical inducers are selected from the group consisting of ascorbic acid 2 phosphate, dexamethasone, beta glycerophosphate, dimethylsulfoxide, and butylated hydroxyanisole.

30. A method of applying small mobile stem (SMS) cells as a substrate for the process of generating spatially-controlled cell patterns using 3D bioprinting device comprising:
providing an isolated population of undifferentiated SMS cells, e.g., the isolated population of suspended SMS cells obtained by the methods of anyone of alternative 1-20; and
generating a spatially-controlled cell pattern using a 3D bioprinting apparatus and said isolated population of undifferentiated SMS cells as a substrate.

31. The method of alternative 30, wherein the 3D bioprinting device is selected from the group consisting of BioBot1®, 3D-Bioplotter®, 3DS Alpha®, and 3Dynamic Omega®.

32. A method of producing an extracellular matrix (ECM) protein in culture using small mobile stem (SMS) cells, the method comprising:
providing an isolated population of undifferentiated SMS cells, e.g., the isolated population of suspended SMS cells obtained by the methods of anyone of alternatives 1-20; and inducing said isolated population of undifferentiated SMS cells to produce an ECM protein.

33. The method of alternative 32, wherein said isolated population of undifferentiated SMS cells are induced to produce an ECM protein by contacting said isolated population of undifferentiated SMS with one or more chemical inducers of ECM protein production such as, a hedgehog inhibitor, a TGF/BMP activator, ascorbic acid, ascorbic acid 2 phosphate, serum present in the growth medium, and/or polystyrene.

34. The method of alternative 33, wherein the produced ECM protein comprises one or both of suspended ECM protein and attached ECM protein.

35. The method of anyone of alternatives 32-34, further comprising isolating the suspended ECM protein e.g., by centrifugation, filtration, or precipitation and/or isolating the attached ECM protein e.g., by scraping the culturing vessel.

36. The method of alternative 35, further comprising lysing or removing any remaining cells from the isolated ECM.

37. The method of any one of alternatives 32-36, wherein the ECM protein is selected from the group consisting of agrin, nidogen, cadherins, clathrin, collagen, defensin, elastin, entactin, fibrillin, fibronectin, keratin, laminin, microtubule-actin cross-linking factor 1, SPARC-like protein, nesprin (nesprin-1, nesprin-2, nesprin-3), fibrous sheath-interacting protein, myomesin, nebulin, plakophilin, integrin, talins, exportins, transportin, tenascin, perlecan, sortilin-related receptor, tensin, titin, total protein, and/or a fragment of any one or more of the aforementioned proteins.

38. The method of any one of alternatives 32-37, further comprising modifying the ECM protein e.g., by freezing, lyophilizing, cross-linking, drying and/or pulverizing the isolated ECM.

39. The method of alternative 38, wherein the modified ECM protein is suitable for promoting cell growth or cell differentiation in vitro or in vivo.

40. The method of any one of alternatives 32-39, wherein the isolated population of undifferentiated SMS cells are cultured on a scaffold, preferably a porous and/or implantable scaffold such as, a scaffold comprising a native decellularized bone, a soft decellularized collagen, a decellularized organ, chitosan, demineralized bone matrix, membrane and barrier allographs, or a combination thereof.

41. The method of alternative 40, wherein the scaffold is synthetic, semi-synthetic, or native.

42. A method for the production of a soft tissue, comprising:
culturing an isolated population of undifferentiated SMS cells, e.g., the isolated population of suspended SMS cells obtained by the methods of anyone of alternatives 1-20, in the presence of peripheral blood;
forming a gel-like structure;
freezing the gel-like structure;
thawing the frozen gel-like structure; and
culturing the thawed gel-like structure, wherein the thawed gel-like structure forms a soft tissue-like structure.

43. The method of alternative 42, wherein the freezing step is performed at −20° C.

44. A composition comprising one or more extracellular matrix (ECM) proteins obtained from a culture of small mobile stem (SMS) cells.

45. The composition of alternative 44, wherein the one or more ECM proteins is denatured.

46. The composition of any one of alternatives 44-45, wherein the one or more ECM proteins is modified by acetylation, acylation, carboxylation, glycosylation, hydroxylation, lipidation, methylation, pegylation, phosphorylation, prenylation, sulfation, or ubiquitination.

47. The composition of any one of alternatives 44-46, wherein the one or more ECM proteins is selected from the group consisting of agrin, nidogen, cadherins, clathrin, collagen, defensin, elastin, entactin, fibrillin, fibronectin, keratin, laminin, microtubule-actin cross-linking factor 1, SPARC-like protein, nesprin (nesprin-1, nesprin-2, nesprin-3), fibrous sheath-interacting protein, myomesin, nebulin, plakophilin, integrin, talins, exportins, transportin, tenascin, perlecan, sortilin-related receptor, tensin, titin, total protein, and/or a fragment of any one or more of the aforementioned proteins.

48. The composition of any one of alternatives 44-47, wherein the one or more ECM proteins comprises a compound or is itself a compound that inhibits microbial growth, such as a bacterial and/or fungi inhibiting compound.

49. The composition of alternative 48, wherein the microbial growth inhibiting compound is an anti-microbial protein selected from the group consisting of collectin, C-type lectin family 4, septin 12, and pancreatic ribonuclease.

50. The composition of any one of alternatives 44-49, wherein the composition is formulated as an aerosol, a cream, an emulsion, a foam, a foamable liquid, a gel, a lotion, an ointment, a paste, a salve, a serum, a solution, or a spray.

51. A system for wound healing comprising a wound dressing material comprising a composition that comprises an extracellular matrix (ECM) protein prepared in accordance with any one of alternatives 44-50.

52. The system of alternative 51, wherein the wound dressing material is a bandage, a wipe, a gauze, a sponge, a mesh, a pad, an adhesive bandage, or an absorbent wound dressing material.

53. The system of any one of alternatives 51-52, wherein the ECM protein is selected from the group consisting of agrin, nidogen, cadherins, clathrin, collagen, defensin, elastin, entactin, fibrillin, fibronectin, keratin, laminin, microtubule-actin cross-linking factor 1, SPARC-like protein, nesprin (nesprin-1, nesprin-2, nesprin-3), fibrous sheath-interacting protein, myomesin, nebulin, plakophilin, integrin, talins, exportins, transportin, tenascin, perlecan, sortilin-related receptor, tensin, titin, total protein, and/or a fragment of any one or more of the aforementioned proteins.

54. A method of treating or ameliorating or promoting the healing of a wound of a subject comprising contacting a wound of a subject with the composition of any one of alternatives 44-50 or with the system of any one of alternatives 51-53.

55. A method of producing a protein comprising:
culturing an isolated population of undifferentiated small mobile stem (SMS) cells in a growth media in a vessel, wherein said growth media promotes production of said protein; optionally
inducing production of proteins; and optionally isolating or purifying said protein.

56. The method of alternative 55, wherein the cells are cultured in the absence of $CO_2$.

57. The method of any one of alternatives 55-56, wherein the cells are cultured in the absence of an antibiotic.

58. The method of any one of alternatives 55-57, wherein the cells are grown in culture media in a vessel having a volume of between 300 mL and 500 L.

59. The method of any one of alternatives 55-58, wherein the protein is coagulation factor XIII A chain, apolipoprotein E, anithrombin III, bone morphogenic protein 1, vitronectin, acidic leucine-rich nuclear phosphoprotein 32 family member A (ANP32A), calcineurin-like phosphoesterase, peptidyl-prolyl cis-trans isomerase, β-enolase, fermitin family homolog 1, microtubule-associated protein RP/EB (MAPRE1), heat shock proteins, LIM and senescent cell antigen-like-containing domain protein 1 (LIMS1), myosin regulatory protein, profilin-1, glycogen phosphorylase, flavin reductase, mitogen activated protein kinase, protein phosphatase, tubulin, chloride intracellular channel proteins, wings apart-like protein homolog (WAPAL), cell division control proteins, osteopontin, BPI fold-containing, elongation factor, plasminogen, aldo-keto reductase, or keratin, or an extracellular matrix protein (ECM), or a fragment of any one or more of the aforementioned proteins.

60. The method of alternative 59, wherein the ECM protein agrin, nidogen, cadherins, clathrin, collagen, defensin, elastin, entactin, fibrillin, fibronectin, keratin, laminin, microtubule-actin cross-linking factor 1, SPARC-like protein, nesprin (nesprin-1, nesprin-2, nesprin-3), fibrous sheath-interacting protein, myomesin, nebulin, plakophilin, integrin, talins, exportins, transportin, tenascin, perlecan, sortilin-related receptor, tensin, titin, total protein, and/or a fragment of any one or more of the aforementioned proteins.

61. The method of any one of alternatives 55-60, wherein the vessel promotes or is configured to promote the growth of SMS cells in suspension.

62. The method of any one of alternatives 55-61, wherein the vessel is a polypropylene vessel, a pretreated siliconized vessel, or a vessel that is configured to promote the growth of SMS cells in suspension.

63. The method of any one of alternatives 55-60, wherein the vessel promotes cell adherence.

64. The method of any one of alternatives 55-63, wherein the cells are induced with one or more chemical inducers.

65. The method of alternative 64, wherein the one or more chemical inducers is dimethyl sulfoxide (DMSO), butylated hydroxyanisole, β-mercaptoethanol, ascorbic acid-2-phosphate, dexamethasone, β-glycerophosphate, dimethylsulfoxide, insulin, isobutylmethylxanthine, or indomethacin, or combinations thereof.

66. The method of any one of alternatives 64-65, wherein the chemical inducers include dexamethasone present in an amount of 0.1 μM, ascorbic acid-2-phosphate present in an amount of 0.05 mM, and β-glycerophosphate present in an amount of 10 mM.

67. A method of producing a tubule or vessel structure comprising culturing endothelial cells with SMS-derived extracellular matrix (ECM), wherein said endothelial cells migrate into and interact with said SMS-derived ECM thereby producing a tubule or vessel structure.

68. A method of selecting an agent or compound that induces, promotes, or contributes to vessel formation, angiogenesis, or arteriogenesis by a cell population, comprising: providing extracellular matrix (ECM) produced from SMS cells, such as the ECM produced according to any of the aforementioned alternatives; contacting said ECM produced from said SMS cells with a first cell population comprising cells capable of vessel formation, angiogenesis, or arteriogenesis, such as endothelial cells; contacting said first cell population that is in contact with said ECM with an agent or compound; and determining whether said agent or compound induces, promotes, or contributes to vessel formation, angiogenesis, or arteriogenesis in said first cell population by comparing the quality or quantity of vessel formation, angiogenesis, or arteriogenesis in said first cell population in contact with said ECM after contact with said agent or compound with a second cell population, preferably of the same cell type as the first cell population, grown in said ECM in the absence of contact with said agent or compound, wherein an increase in quantity or quality of vessel formation, angiogenesis, or arteriogenesis in said first cell population as compared to said second cell population identifies said agent or compound as one for selection as an agent or compound that induces, promotes, or contributes to vessel formation, angiogenesis, or arteriogenesis by a cell population.

BRIEF DESCRIPTION OF THE DRAWINGS

In addition to the features described above, additional features and variations will be readily apparent from the following descriptions of the drawings and exemplary embodiments. It is to be understood that these drawings depict typical embodiments, and are not intended to be limiting in scope.

FIG. 28B—200×).

FIG. 29B—100×; FIG. 29C—200×; FIG. 29D—400×).

FIG. 30B—40×).

FIGS. 33B and 33C—400×).

DETAILED DESCRIPTION

Figure 1:
FIG. 1 shows cultured adherent multi-cellular layers of SMS cells, appearing opaque at the bottom of the flask. The medium contains floating undifferentiated SMS cells.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

SMS cells are unique stem cells because they are highly mobile, and because they have a remarkable potential to differentiate into specialized lineages, including various somatic cells and tissues. Given the unique properties of SMS cells, they are expected to have far-reaching applications in the areas of basic scientific research, pharmacology, and regenerative medicine. SMS cell lines can provide a powerful in vitro model for the study of the molecular and cellular biology of early human development, for functional genomics, drug screening, and discovery. They may serve for toxicology and teratogenicity high throughput screening. Because SMS are capable of self-renewal and differentiation, they can serve as a renewable source of functionally mature differentiated cells or tissues for transplantation therapy. In addition, transplanted genetically-modified SMS cells can serve as vectors to carry and express genes in target organs in the course of gene therapy. Importantly, SMS cells can be used for the production of numerous gene products, and are useful for the production of ECM proteins.

Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, NY 1994); Sambrook et al., Molecular Cloning, A Laboratory Manual, Cold Springs Harbor Press (Cold Springs Harbor, N Y 1989). For purposes of the present disclosure, the following terms are defined below.

The articles "a" and "an" are used herein to refer to one or to more than one (for example, at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

Throughout this specification, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

In some embodiments, the "purity" of any given agent (e.g., antibody, polypeptide binding agent) in a composition may be specifically defined. For instance, certain compositions may comprise an agent that is at least 80, 85, 90, 91, 92, 93, 94, 95, 96, 97, 98, 99, or 100% pure, including all decimals in between, as measured, for example and by no means limiting, by high pressure liquid chromatography (HPLC), a well-known form of column chromatography used frequently in biochemistry and analytical chemistry to separate, identify, and quantify compounds.

As used herein, the terms "function" and "functional" and the like refer to a biological, enzymatic, or therapeutic function.

The term "isolated" is meant material that is substantially or essentially free from components that normally accompany it in its native state. For example, an "isolated polynucleotide," as used herein, includes a polynucleotide that has been purified from the sequences that flank it in its naturally-occurring state, e.g., a DNA fragment which has been removed from the sequences that are normally adjacent to the fragment. Alternatively, an "isolated peptide" or an "isolated polypeptide" and the like, as used herein, includes the in vitro isolation and/or purification of a peptide or polypeptide molecule from its natural cellular environment, and from association with other components of the cell; for example, it is not significantly associated with in vivo substances.

The practice of the present disclosure will employ, unless indicated specifically to the contrary, conventional methods of molecular biology and recombinant DNA techniques within the skill of the art, many of which are described below for the purpose of illustration. Such techniques are explained fully in the literature. See, e.g., Sambrook, el al, Molecular Cloning: A Laboratory Manual ($3^{rd}$ Edition, 2000); DNA Cloning: A Practical Approach, vol. 1 & II (D. Glover, ed.); Oligonucleotide Synthesis (N. Gait, ed., 1984); Oligonucleotide Synthesis: Methods and Applications (P. Herdewijn, ed., 2004); Nucleic Acid Hybridization (B. Hames & S. Higgins, eds., 1985); Nucleic Acid Hybridization: Modern Applications (Buzdin and Lukyanov, eds., 2009); Transcription and Translation (B. Hames & S. Higgins, eds., 1984); Animal Cell Culture (R. Freshney, ed., 1986); Freshney, R. I. (2005) Culture of Animal Cells, a Manual of Basic Technique, $5^{th}$ Ed. Hoboken NJ, John Wiley & Sons; B. Perbal, A Practical Guide to Molecular Cloning ($3^{rd}$ Edition 2010); Farrell, R., RNA Methodologies: A Laboratory Guide for Isolation and Characterization ($3^{rd}$ Edition 2005).

Wound Healing

The term "wound" is understood to mean a break in the continuity of body tissues with or without substance loss, such a break in general being caused by mechanical injuries or physically caused cell damage. A wound can include skin damage, a burn, radiation damage, sun burn, an abrasion, a laceration, an incision, a sore, a puncture wound, a penetration wound, a gunshot wound, or a crushing injury. A wound may include mechanical wounds, including cutting, laceration, scratch, abrasion, piercing, puncture, penetration, crushing, blunt force trauma, and contusion wounds. A wound may include thermal wounds, which are caused by the action of extreme heat or cold. A wound may include chemical wounds caused by the action of chemicals, in particular by erosion by acids or alkalis. A wound may further include tissue breaks or damage which arise under the action of actinic radiation, e.g. ultraviolet radiation and/or ionizing radiation, are described as radiation wounds. A wound may be necrotizing, infected, chronic, or acute.

As used herein, the term "wound healing" described the phases of a wound from injury to healing. In the first phase, also described as latency or inflammatory phase, within the first hours after wounding has occurred, exudation of body fluids takes place, in particular of blood, to free the wound opening from foreign bodies, germs and dead tissue. Next, a scab, which protects the wound externally from the penetration of germs and foreign bodies, is formed through clotting of the blood that has emerged. After the formation of the scab, the resorption phase of the latency phase begins, in which a catabolic autolysis also takes place, which includes macrophage migration into the wound tissue and phagocytosis of coagulated blood in the wound opening. Foreign bodies or microorganisms which may have penetrated are degraded in this phase, which can be associated with mild to moderate inflammatory symptoms. Further, in the resorption phase the build-up of the basal epithelium and of granulation tissue begins. After about one to three days after causation of the wound, the latency phase is generally completed and the latency phase passes into the second phase, a proliferation or granulation phase, which in general lasts from the fourth to the seventh day after the injury. During this phase, anabolic repair begins. This repair includes the formation of collagen by fibroblasts. In the final phase, the repair or epithelization phase, which begins from about the eighth day after the occurrence of the wound, final scar tissue is formed and the squamous epithelium of the skin is renewed. The scar tissue formed has neither sebaceous nor sweat glands and appears white to mother-of-pearl on the skin. In contrast to undamaged tissue, the collagen in the scar tissue is no longer complexly linked, but is instead aligned parallel.

Further information on the term "wound healing" can be found in Pschyrembel—Clinical Dictionary, 257$^{th}$ edition, 1994, Verlag de Gruyter, Berlin/New York, which is expressly incorporated by reference herein in its entirety.

Impaired wound healing is a major complication underlying several disease processes. Efficient wound healing is hampered by a wide variety of processes including hypoxia (oxygen deprivation), inflammation, infection, and oxidative stress through the generation of harmful reactive oxygen species (ROS). The inherent complexity of wound healing has resulted in limited efficacy of most therapies that target single parameters involved in the slow healing processes.

Wound healing strays from its normal process as a result of microbial infections. A variety of microbes can infect a wound, complicating the normal healing process. Many wound infections are caused by microbes such as *Proteus mirabilis, Pseudomonas aeruginosa, Staphylococcus epidermidis, Staphylococcus aureus*, and *Escherichia coli*. Although antibiotics have been developed to mitigate microbial infections, a variety of strains have developed resistance. For example, numerous strains of *Staphylococcus aureus* have developed resistance to beta-lactam antibiotics, such as methicillin and oxacillin, and various other antibiotic classes such as glycopeptide antibiotics, sulfonamides, quinolones, or tetracyclines. In some embodiments, the wound healing formulations described herein have anti-microbial properties, capable of removing microorganisms from a wound, inhibiting the growth of microorganisms in a wound, preventing the growth of microorganisms in a wound, or killing microorganisms that may be present in a wound.

As used herein, the term "wound healing compound" or "system for wound healing" refers to a compound or system that is capable of healing a wound. A wound healing compound has anti-microbial properties, capable of removing microorganisms from a wound, and capable of preventing growth and proliferation of microorganisms on a surface. In some embodiments, the wound healing compound is capable of accelerating wound healing. In some embodiments, the wound healing compound is formulated within a composition, such as an aerosol, an emulsion, a foam, a foamable liquid, a paste, an ointment, a cream, a spray, a spritz, a mist, a liquid, a salve, a serum, a gel, a lotion, or a solution. In some embodiments, the formulation is configured within a system that includes wound healing compounds to be applied to a wound dressing material, including a bandage, a wipe, a gauze, a sponge, a mesh, a pad, an adhesive bandage, or an absorbent wound dressing material. As described herein, a compound may be formulated as a topical formulation, prepared for topical application.

Stem Cells

"Stem cells", as used herein, refers to cells which under suitable conditions are capable of differentiating into other cell types having a particular, specialized function (for example, "fully differentiated" cells) while under other suitable conditions are capable of self-renewing and remaining in an undifferentiated multipotent or pluripotent state as detailed below. A "cell" as used herein refers to a single cell as well as to a population of (for example, more than one) cells. The population may be a pure population including one cell type. Alternatively, the population may include more than one cell type. The stem cells are preferably, small mobile stem (SMS) cells obtained from, for example, peripheral blood, umbilical cord blood, bone marrow, or a solid tissue.

"SMS cells", as used herein refers to a cell or a cell population characterized in that the cells are adherent cells of about 5 µm in diameter. The SMS cells are equi-dimensional, with strict radial symmetry, and exhibit a translucent cytoplasm and circular nucleus that includes a centrally located circle of a different light contrast, as viewed in a light microscope. In addition, SMS cells demonstrate an extraordinary resistance to various non-physiological conditions, including low and high temperature, freezing and thawing in standard growth medium, dehydration, high pH values, and variations of ionic strength. Furthermore, SMS cells are characterized by their high mobility of up to about 1.5 µm/sec "Cell culture" or "cultured cell", as used herein, refer to cells or tissues that are maintained, cultured, cultivated or grown in an artificial, in vitro environment. Included within this term are continuous cell lines (e.g. with an immortal phenotype), primary cell cultures, finite cell lines (e.g., non-transformed cells), and any other cell population maintained in vitro. In this connection, a primary cell is a cell which is directly obtained from a tissue or organ of an animal, including a human, in the absence of culture. Typically, though not necessarily, a primary cell is capable of undergoing ten or fewer passages in vitro before senescence and/or cessation of proliferation.

"Undifferentiated", as used herein, refers to cultured cells when a substantial proportion (at least 20%, and possibly over 50% or 80%) of the cells and their derivatives in the population display morphological characteristics of undifferentiated cells, distinguishing them from differentiated cells of embryo or adult origin. Cells are recognized as proliferating in an undifferentiated state when they go through at least 1 population doubling during a cultivation period of at least 3 weeks, while retaining at least about 50%, or the same proportion of cells bearing characteristic markers or morphological characteristics of undifferentiated cells after said cultivation period.

"Maintenance" means continued survival of a cell or population of cells, at times, with or without an increase in the numbers of cells. "Proliferation", "propagation", "expansion" and "growth", which may be used interchangeably with each other, refer to an increase in cell number. According to one embodiment, this term refers to a continuous survival of the cells for at least 6, 7, 8, 9, 10, 11, 12, 13, 14, 15, 16, 17, 18, 19, 20, 21, 22, 23, 24, 25, 26, 32, 48, 52, 104 or more weeks or within a range defined by any two of the aforementioned time frames. In the alternative, the continuous survival of the cells continues for at least 25, 26, 27, 28, 29, or 30 or more passages or within a range defined by any two of the aforementioned number of passages.

"Cell suspension" as used herein, refers to a culture of cells in which the majority of the cells freely float in the medium, typically a culture medium (system), and the cells floating as single cells, as cell clusters and/or as cell aggregates. In other words, the cells survive and propagate in the medium without being attached to a solid or semi solid substrate. "Adherent cells" as used herein refers to a cell or cell population that adheres to a substrate or surface.

"Culture system" as used herein, refers to culture conditions for supporting the maintenance and propagation of SMS cells or somatic cells derived therefrom, as well as, under selected conditions, for supporting derivation and propagation of undifferentiated or differentiated SMS cells. The term denotes a combination of elements, which can include a basic medium (a cell culture medium usually including a defined base solution, which includes salts, sugars and amino acids) and a serum replacement supplement. The culture system may further include other elements such as, without being limited thereto, an extracellular matrix (ECM) component, additional serum or serum replacements, a culture (nutrient) medium and other exogenously added factors, which together provide suitable conditions that support SMS cell growth, cell culture maintenance, cell differentiation, or expression of various molecules. In the relevant context, the term "culture system" also encompasses the cells cultured therein.

As used herein, "extracellular matrix (ECM)" is the extracellular component consisting of an intricate network of proteins and polysaccharides that are secreted by cells. SMS-derived ECM refers to ECM that has been produced by small mobile stem cells. Some embodiments provided herein related to methods of producing SMS-derived ECM. Some embodiments herein relate to methods of culturing cells, including endothelial cells, keratinocytes, fibroblasts, or other cells together with SMS-derived ECM. In some embodiments, the cultured cells, for example, including endothelial cells, keratinocytes, fibroblasts, or other cells interact with SMS-derived ECM. In some embodiments, the cultured cells, including endothelial cells, keratinocytes, fibroblasts, or other cells migrate into SMS-derived ECM. In some embodiments, the cultured cells, including endothelial cells, keratinocytes, fibroblasts, or other cells proliferate in SMS-derived ECM. In some embodiments, the cultured cells, including endothelial cells, keratinocytes, fibroblasts, or other cells form adherent layers on the SMS-derived ECM. In some embodiments, the cultured cells, including endothelial cells, keratinocytes, fibroblasts, or other cells form stable complexes or associations on the SMS-derived ECM. In some embodiments, the cultured cells, including endothelial cells, keratinocytes, fibroblasts, or other cells survive for extended periods of time, for example, for 1 week, 2, weeks, 3 weeks, 1 month, 2 months, 3 months, 4 months, 5 months, 6 months, 9 months, 1 year, or longer on the SMS-derived ECM.

In some embodiments, the cultured cells, for example, endothelial cells, form tubules or vessel structures on the ECM obtained from the SMS cells. Some embodiments provided herein relate to methods of determining the efficacy of one or more agents or compounds to inhibit or promote the formation of tubules or vessel structures in ECM obtained from the SMS cells. In some embodiments, the tubules or vessel structures that have formed from endothelial cell interaction with SMS-derived ECM are contacted with one or more agents or compounds that inhibit or promote angiogenesis or arteriogenesis. In some embodiments, the inhibition or promotion of angiogenesis or arteriogenesis of a cell in contact with the ECM obtained from the SMS cells, such as a population of endothelial cells, is compared to a control cell population, such as a control endothelial cell population, grown on the ECM obtained from the SMS cells, which has not received the one or more agents or compounds so as to determine the efficacy of the one or more agents or compounds for inhibiting or promoting angiogenesis or arteriogenesis by the cells, e.g., endothelial cells, which are in contact with the ECM obtained from the SMS cells. In some embodiments, the inhibition or promotion of angiogenesis or arteriogenesis is determined by measuring the extent of vessel growth and/or the quality of vessel formation, and comparing these characteristics to the control sample that has not received the one or more agents.

The present disclosure concerns culture systems and methods for the maintenance and preferably propagation of undifferentiated, SMS cells in a culture system that supports the maintenance of the SMS cells in an undifferentiated multipotent or pluripotent state. The culture system provided herein has been found to be especially suitable for large scale and long term maintenance of undifferentiated stem cells.

The term "extracellular matrix" is recognized in the art. Its components include one or more of the following proteins: fibronectin, laminin, vitronectin, tenascin, entactin, thrombospondin, elastin, gelatin, collagen, fibrillin, merosin, anchorin, chondronectin, link protein, bone sialoprotein, osteocalcin, osteopontin, epinectin, hyaluronectin, undulin, epiligrin, and/or kalinin. It is intended that the term "extracellular matrix" encompass a presently unknown extracellular matrix that may be discovered in the future, since its characterization as an extracellular matrix will be readily determinable by persons skilled in the art.

"Gene products" as used herein refers to the product of a gene that is transfected into a cell or population of cells. The gene that is transfected can encode, for example, a protein, such as a growth factor, a cytokine, a peptide hormone, a protein hormone, an enzyme, a protein fragment, or an extracellular matrix protein. Specific examples include, an epidermal growth factor (EGF), a platelet derived growth factor (PDGF), a fibroblast growth factor (FGF and bFGF), a transforming growth factor (TGF-α and TGF-β 1, 2, & 3), a vascular endothelial growth factor (VEGF), a hepatocyte growth factor (HGF), a keratinocyte growth factor (KGF), a nerve growth factor (NGF), erythropoietin (EPO), an insulin-like growth factors (IGF-I and IGF-II), an interleukin cytokine (IL-la, IL-13, IL-2, IL-3, IL-4, IL-5, IL-6, IL-7, IL-8, IL-9, IL-10, IL-11, IL-12, IL-13), an interferon (IFN-α, IFN-β, and IFN-γ), a tumor necrosis factor (TNFα and TNF-β), a colony stimulating factor (GM-CSF and M-CSF), insulin, parathyroid hormone, fibronectin, vitronectin, tenascin, thrombospondin, gelatin, fibrillin, merosin, anchorin, chondronectin, link protein, bone sialoprotein, osteocalcin, osteopontin, epinectin, hyaluronectin, undulin, epiligrin, kalinin, collagenase, collagen, elastin, laminin, agrin, nidogen, and/or entactin or variations and/or combinations thereof.

"Cell marker", as used herein, refers to is any phenotypic feature of a cell that can be used to characterize it or discriminate it from other cell types. A marker may be a protein (including secreted, cell surface, or internal proteins; either synthesized or taken up by the cell); a nucleic acid (such as an mRNA, or enzymatically active nucleic acid molecule) or a polysaccharide. Included are determinants of any such cell components that are detectable by antibody, lectin, probe or nucleic acid amplification reaction that are specific for the cell type of interest. The markers can also be identified by a biochemical or enzyme assay that depends on the function of the gene product. Associated with each marker is the gene that encodes the transcript, and the events that lead to marker expression. A marker is said to be preferentially expressed in an undifferentiated or differentiated cell population, if it is expressed at a level that is at least 5 times higher (in terms of total gene product measured in an antibody or PCR assay) or 5 times more frequently (in terms of positive cells in the population). Markers that are expressed 10, 100, or 10,000 times higher or more frequently are increasingly more preferred.

Small mobile stem (SMS) cells are conveniently grown in T25 flasks using growth medium (e.g., in an incubator at 37° C. and 5% $CO_2$). The SMS cell population may contain a heterogeneous cell population of undifferentiated SMS cells and SMS derived differentiated cells. SMS undifferentiated cells are present as a floating and an adherent fraction and the floating fraction is predominantly undifferentiated SMS cells (e.g., greater than or equal to 50%, 55%, 60%, 65%, 70%, 75%, 80%, 85%, 90%, or 95% undifferentiated SMS cells or an amount of undifferentiated SMS cells that is within a range defined by any two of the aforementioned values). Accordingly, some alternatives concern a suspension of non-adherent and undifferentiated SMS cells, which are preferably grown in a liquid media in a manner that prevents adherence (e.g., in a polypropylene vessel or flask). In some alternatives, the floating and undifferentiated SMS cell population is greater than or equal to 50%, 55%, 60%, 65%, 70%, 75%, 80%, 85%, 90%, or 95% undifferentiated SMS cells or an amount of undifferentiated SMS cells that is within a range defined by any two of the aforementioned values.

Undifferentiated SMS cells can be isolated or purified by differential centrifugation, removing clumps of cells or differentiated cells at low centrifugation speed followed by centrifuging undifferentiated SMS cells at high speed. Alternatively, the undifferentiated cells may be isolated by filtration, including differential filtration using filters having progressively smaller pore sizes to a pore size of 3-5 µm. Alternatively, the undifferentiated cells may be isolated by immune conjugation (e.g., a binding partner specific for a stem cell receptor on SMS cells, wherein the binding partner, such as an antibody, is conjugated to a bead, such as a magnetic bead or via FACS cell sorting), or differential filtration using filters having progressively smaller pore sizes to a pore size of 3-5 µm The isolated undifferentiated SMS cells are examined under the microscope for homogeneity. By passing the cells for at least 25 passages (e.g., 25, 26, 27, 28, 29, 30, 31, 32, 33, 34, 35, 36, 37, 38, 39, or 40 passages or within a range defined by any two of the aforementioned number of passages) prior to employing one or more of the isolation protocols above, one can obtain an improved homogeneous population of SMS cells.

The SMS cells can be grown a variety of mediums with or without serum and with or without inclusion of a differentiation induction compound (e.g., insulin). The cell growth medium is replaced every week by centrifuging the SMS cells at 4200 g for 15 min. The centrifugation may be varied at 3000 g, 3500 g, 4000 g, 4100 g, 4200 g, 4300 g, 4500 g, or 5000 g or by centrifugation at a speed that is within a range defined by any two of the aforementioned speeds, and the time adjusted accordingly. Under these conditions the volume size of the medium (cell crowdedness) is growth limiting to SMS cells. The SMS cell homogeneity is assessed microscopically and the SMS cell count is estimated by assessing spectroscopically turbidity of the suspension and/or by measuring the size of the pellet after centrifugation at high speed. Suspension cultures of SMS cells facilitate transfer and cloning as the cells are easily split and/or transferred to a new tube with growth medium and such methods of splitting and/or transferring a culture of cells from an existing culture to a new culture is performed without using an enzyme that liberates the cells from the culture dish or a basal cell layer (e.g., trypsin). SMS cells predominantly grow as individual cells, without clumping and the SMS cell suspensions can remain undifferentiated despite transfer procedures. The suspension culture is also scalable such that increasing the volume of the medium increases the number of cells obtained.

SMS cells can be differentiated into a variety of cells, including, for example, adipogenic cells, neurogenic cells, or osteogenic cells. The SMS cells are first grown to confluence and then incubated with an appropriate induction medium, which can include dimethyl sulfoxide (DMSO), butylated hydroxyanisole, β-mercaptoethanol, ascorbic acid-2-phosphate, dexamethasone, β-glycerophosphate, dimethylsulfoxide, insulin, isobutylmethylxanthine, indomethacin, or combinations thereof. In some embodiments, one or more of the aforementioned chemical inducers may be present in an amount of 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10%, or an amount within a range defined by any two of the aforementioned values. In some embodiments, one or more of the aforementioned chemical inducers may be present in an amount of 0.0001, 0.0005, 0.001, 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, or 10 mM or an amount within a range defined by any two of the aforementioned values. In some embodiments, the induction medium lacks serum. Accordingly, in some embodiments, the induction medium includes one or more of dimethyl sulfoxide (DMSO), butylated hydroxyanisole, β-mercaptoethanol, ascorbic acid-2-phosphate, dexamethasone, β-glycerophosphate, dimethylsulfoxide, insulin, isobutylmethylxanthine, or indomethacin, in the absence of serum.

Without wishing to be bound by theory, it is contemplated that in some embodiments, the chemical inducer DMSO acts as a facilitating inducers, allowing access of additional compounds to the cells. While still not wishing to be bound by theory, it is contemplated that in some embodiments, β-mercaptoethanol acts to reduce SH groups.

In some embodiments, the differentiated cells express specific markers (for example, adipogenic cells express markers specific for adipogenic cells; neurogenic cells express markers specific for neurogenic cells; and osteogenic cells express markers specific for osteogenic cells). In some embodiments, SMS cells that have differentiated into adipose cells express adipose specific markers, including CD44, integrin, and ICAM-1/CD54, or other markers of adipocyte differentiation. In some embodiments, SMS cells that have differentiated into neural cells express neural specific markers, including doublecortin domain containing protein 2C (DCDC2), keratin associated protein (KRTAP) 5-1, nestin, SOX2, ABCG2, FGF R4, frizzled-9, NCAM, Musashi-1, neuron-specific Class III β-tubulin, microtubule-associated protein 2, neuron specific enolase, calretinin, tyrosinse hydroxylase, choline acetyltransferase, calbindin, neuronal nuclei antigen, GABA, or other markers of neuronal cell differentiation. In some embodiments, SMS cells that have differentiated into osteogenic cells express osteocyte specific markers, including alkaline phosphatase, runt-related transcription factor 2, annexin A1 and/or A5, choline transporter-like protein 1, or osteocalcin, or other markers of osteogenic cell differentiation.

Undifferentiated SMS cells can be used in a variety of therapeutic, protein production, drug discovery, and diagnostic approaches. SMS cell functionality is assessed by testing differentiation capacity of SMS cells using various different differentiation induction media. Native or genetically modified SMS cells can be used to produce various small and large compounds including but not limited to proteins, such as growth factors and extracellular matrix proteins). SMS cells can also be used to generate other cells vis a vis differentiation, formation of tissues or tissue like structures, organoids or organs. SMS cells can also be applied as a substrate for the process of generating spatially-controlled cell patterns using 3D printing (3D bioprinting). This can be achieved by using a 3D bioprinter, which includes, for example, BioBot1®, 3D-Bioplotter®, 3DS Alpha®, and 3Dynamic Omega® in conjunction with the SMS cells described herein. Furthermore, genetically modified SMS cells (containing a marker such as GFP) can be used to trace cellular interactions, differentiation and other cell based activities.

In some embodiments, SMS cells are used for the production of a protein. In some embodiments, induction of SMS cells causes differential expression of proteins of SMS cells grown in suspension. SMS cells can be grown in a suspension volume of 0.001, 0.005, 0.010, 0.05, 0.1, 0.2, 0.3, 0.4, 0.5, 0.6, 0.7, 0.8, 0.9, 1, 2, 3, 4, 5, 6, 7, 8, 9, 10, 15, 20, 30, 40, 50, 60, 70, 80, 90, 100, 150, 200, 250, 300, 350, 400, 450, 500, 600, 700, 800, 900, or 1000 L, or in a volume within a range defined by any two of the aforementioned values. In some embodiments, the SMS cells are grown in a bioreactor having a volume from 0.001 L to 1000 L. In some embodiments, the SMS cells are grown in a bioreactor having a volume of 0.001, 0.005, 0.010, 0.05, 0.1, 0.2, 0.3, 0.4, 0.5, 0.6, 0.7, 0.8, 0.9, 1, 2, 3, 4, 5, 6, 7, 8, 9, 10, 15, 20, 30, 40, 50, 60, 70, 80, 90, 100, 150, 200, 250, 300, 350, 400, 450, 500, 600, 700, 800, 900, or 1000 L, or in a volume within a range defined by any two of the aforementioned values. In some embodiments, SMS cells are grown in a WAVE® bioreactor. As used herein, the term "container" refers to a container wherein SMS cells are grown, and can include a bioreactor, a culture vessel, a flask, a test tube, a dish, or other vessel capable of growing cultures of cells.

In some embodiments, the culture vessel promotes the growth of SMS cells in suspension. In some embodiments, the culture vessel is a polypropylene vessel, a pretreated siliconized vessel, or a vessel that otherwise promotes or is configured to promote the growth or expansion of SMS cells in culture. In some embodiments, the culture vessel promotes cell adherence.

In some embodiments, SMS cells are grown in the presence of one or more chemical inducers, which causes increased SMS cell concentration, production of proteins, or both. In some embodiments, the one or more chemical inducers includes one or more of dimethyl sulfoxide (DMSO), butylated hydroxyanisole, β-mercaptoethanol, ascorbic acid-2-phosphate, dexamethasone, β-glycerophosphate, dimethylsulfoxide, insulin, isobutylmethylxanthine, or indomethacin. In some embodiments, one or more of the aforementioned chemical inducers may be present in an amount of 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10%, or an amount within a range defined by any two of the aforementioned values. In some embodiments, one or more of the aforementioned chemical inducers may be present in an amount of 0.0001, 0.0005, 0.001, 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, or 10 mM or an amount within a range defined by any two of the aforementioned values. In some embodiments, the induction medium lacks serum.

In some embodiments, the induction of SMS cells in suspension results in an increased concentration of SMS cells as compared to SMS cells grown in the absence of one or more inducer. In some embodiments, SMS cell concentration increases by an amount of 5, 10, 15, 20, 25, 30, 35, 40, 45, 50, 55, 60, 65, 70, 75, 80, 85, 90, 95, 100, 150, 200, 300, 400, or 500% or greater, or an amount within a range defined by any two of the aforementioned values as compared to a control population of SMS cells that are grown in the absence of one or more chemical inducers. In some embodiments, SMS cell concentration increases by 1, 2, 3, 4, 5, 6, 7, 8, 9, or 10 fold, or an amount within a range defined by any two of the aforementioned values, as compared to a control population of SMS cells that are grown in the absence of one or more chemical inducers.

In some embodiments, SMS cells grown in the presence of one or more chemical inducers that induce the production of one or more proteins. In some embodiments, the one or more proteins produced by inducing SMS cells include one or more of coagulation factor XIII A chain, apolipoprotein E, anithrombin III, bone morphogenic protein 1, vitronectin, acidic leucine-rich nuclear phosphoprotein 32 family member A (ANP32A), calcineurin-like phosphoesterase, peptidyl-prolyl cis-trans isomerase, O-enolase, fermitin family homolog 1, microtubule-associated protein RP/EB (MAPRE1), heat shock proteins, LIM and senescent cell antigen-like-containing domain protein 1 (LIMS1), myosin regulatory protein, profilin-1, glycogen phosphorylase, flavin reductase, mitogen activated protein kinase, protein phosphatase, tubulin, chloride intracellular channel proteins, wings apart-like protein homolog (WAPAL), cell division control proteins, osteopontin, BPI fold-containing, elongation factor, plasminogen, aldo-keto reductase, or keratin.

In some embodiments, one or more proteins produced by induction of SMS cells in culture are enriched, isolated, and/or purified. In some embodiments, one or more of coagulation factor XIII A chain, apolipoprotein E, anithrombin III, bone morphogenic protein 1, vitronectin, acidic leucine-rich nuclear phosphoprotein 32 family member A (ANP32A), calcineurin-like phosphoesterase, peptidyl-prolyl cis-trans isomerase, β-enolase, fermitin family homolog 1, microtubule-associated protein RP/EB (MAPRE1), heat shock proteins, LIM and senescent cell antigen-like-containing domain protein 1 (LIMS1), myosin regulatory protein, profilin-1, glycogen phosphorylase, flavin reductase, mitogen activated protein kinase, protein phosphatase, tubulin, chloride intracellular channel proteins, wings apart-like protein homolog (WAPAL), cell division control proteins, osteopontin, BPI fold-containing, elongation factor, plasminogen, aldo-keto reductase, or keratin is enriched, isolated and/or purified. In some embodiments, the production of one or more proteins may be carried out in large scale, for example in a volume of greater than or equal to 1 liter, including 1, 2, 3, 4, 5, 6, 7, 8, 9, 10, 20, 30, 40, 50, 100, 150, 200, 250, 300, 350, 400, 450, 500, 600, 700, 800, 900, 1000 or greater, or a volume within a range defined by any two of the aforementioned values.

In some embodiments, SMS cells are grown in a medium that promotes enlargement of the cells. In some embodiments, a medium that promotes SMS cell enlargement includes basal medium MesenPRO™. In some embodiments, enlarged SMS cells adhere to a surface. In some embodiments, enlarged SMS cells undergo morphological changes.

In some preferred alternatives, the SMS cells are used to generate extracellular matrix (ECM) proteins while remaining in suspension. In some alternatives, The SMS cells (whether in suspension or adherent) are transformed with a gene encoding an ECM protein. SMS cells can be grown in suspension (whether transformed with a gene encoding an ECM protein or a native SMS cell) and are preferably maintained in an undifferentiated state. Several passages of the cells are made so as to obtain a homogeneous population of undifferentiated SMS cells in suspension (e.g., greater than or equal to 50%, 55%, 60%, 65%, 70%, 75%, 80%, 85%, 90%, or 95% undifferentiated SMS cells or an amount of undifferentiated SMS cells that is within a range defined by any two of the aforementioned values). Chemical inducers of ECM protein production are provided to the culture (e.g., a hedgehog inhibitor and/or a TGF/BMP activator) and the ECM generated in the suspension is recovered (e.g., by filtration, centrifugation, or immune conjugation). Similarly, ECM can be made with the adherent SMS cells described herein. In this alternative, SMS cells (whether transformed with an gene encoding an ECM protein or a native SMS cell) are seeded on T25 flasks or plates (e.g., polystyrene; physical surface inducers) and the adherent cells are grown for several passages so as to obtain a homogeneous population of undifferentiated SMS cells in suspension (e.g., greater than or equal to 50%, 55%, 60%, 65%, 70%, 75%, 80%, 85%, 90%, or 95% undifferentiated SMS cells or an amount of undifferentiated SMS cells that is within a range defined by any two of the aforementioned values). Once a desired level of homogeneity is obtained, chemical inducers of ECM production are provided to the medium, including, for example, a hedgehog inhibitor and/or a TGF/BMP activator. The ECM generated in the suspension is then recovered (e.g., by filtration, centrifugation, or immune conjugation). After about two weeks, floating ECM is preferably harvested by centrifugation at high speed. Adherent ECM is harvested at about the same time by scrapping the proteins from bottom of the flask or dish.

In some embodiments, a SMS-derived ECM produces one or more anti-microbial compounds or the ECM protein itself has anti-microbial, such as antibacterial, antiviral, or antifungal properties. In some embodiments, the antimicrobial compounds or ECM proteins having antimicrobial properties produced by SMS cells comprise collectin, C-type lectin family 4, septin 12, or pancreatic ribonuclease. In some embodiments, SMS cells may be grown in the absence of an antibiotic due to the self-production of anti-microbial compounds.

Some embodiments herein relate to a composition comprising one or more ECM proteins obtained from a culture of SMS cells. In some embodiments, the one or more ECM protein is modified. In some embodiments, a modified ECM protein is modified by denaturation, acetylation, acylation, carboxylation, glycosylation, hydroxylation, lipidation, methylation, pegylation, phosphorylation, prenylation, sulfation, and/or ubiquitination. In some embodiments, the one or more ECM proteins comprise one or more of agrin, nidogen, cadherins, clathrin, collagen, defensin, elastin, entactin, fibrillin, fibronectin, keratin, laminin, microtubule-actin cross-linking factor 1, SPARC-like protein, nesprin (nesprin-1, nesprin-2, nesprin-3), fibrous sheath-interacting protein, myomesin, nebulin, plakophilin, integrin, talins, exportins, transportin, tenascin, perlecan, sortilin-related receptor, tensin, titin, total protein, and/or a fragment of any one or more of the aforementioned proteins. In some embodiments, the one or more ECM proteins comprise a microbial growth inhibiting compound, including, for example, collectin, C-type lectin family 4, septin 12, or pancreatic ribonuclease. In some embodiments, the composition is formulated as an aerosol, a cream, an emulsion, a foam, a foamable liquid, a gel, a lotion, an ointment, a paste, a salve, a serum, a solution, or a spray. In some embodiments, the composition is applied to a wound dressing material to form a wound healing system. In some embodiments, the wound dressing material is a bandage, a wipe, a gauze, a sponge, a mesh, a pad, an adhesive bandage, or an absorbent wound dressing material.

In some embodiments, SMS-derived ECM is obtained from SMS cells grown in in suspension. In some embodiments, SMS-derived ECM is obtained from SMS cells grown in suspension In some embodiments, a variety of cells is grown with and interacts with SMS-derived ECM. In some embodiments, cells including endothelial cells, keratinocytes, or fibroblast cells are grown in the presence of SMS-derived ECM and/or interact with SMS-derived ECM.

Figure 25A:
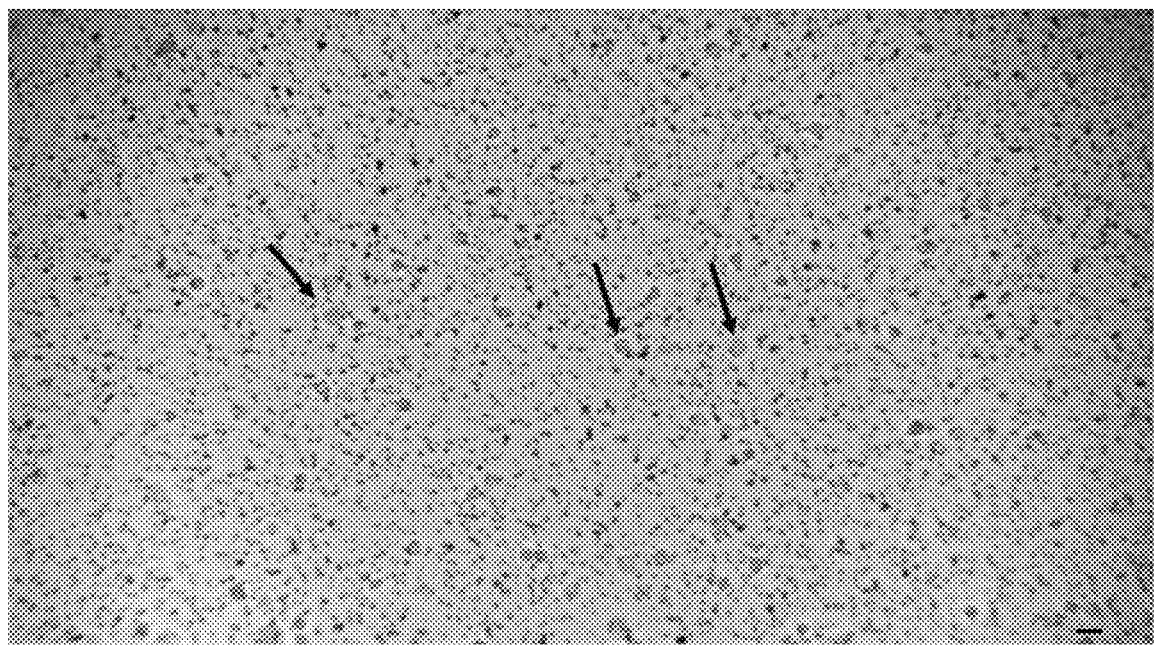
FIGS. 25A and 25B depict human umbilical cord vascular endothelial cells (arrows) migrating into the ECM derived by SMS cells (100×; bar=50 μm).
Figure 25B:
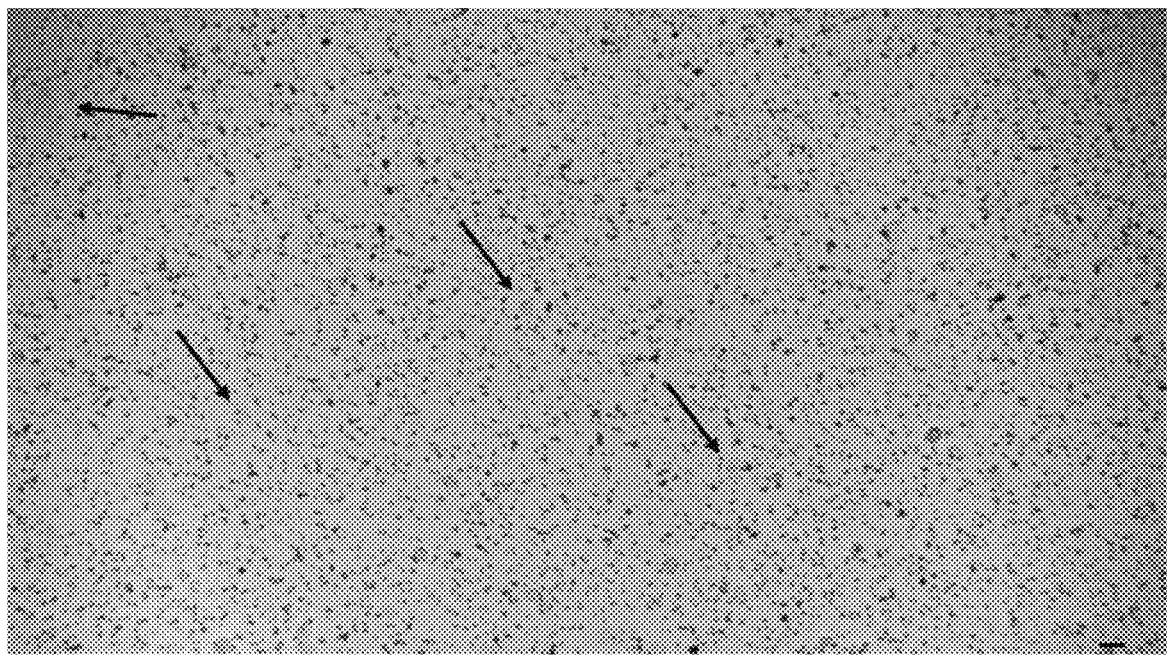
Figure 26A:
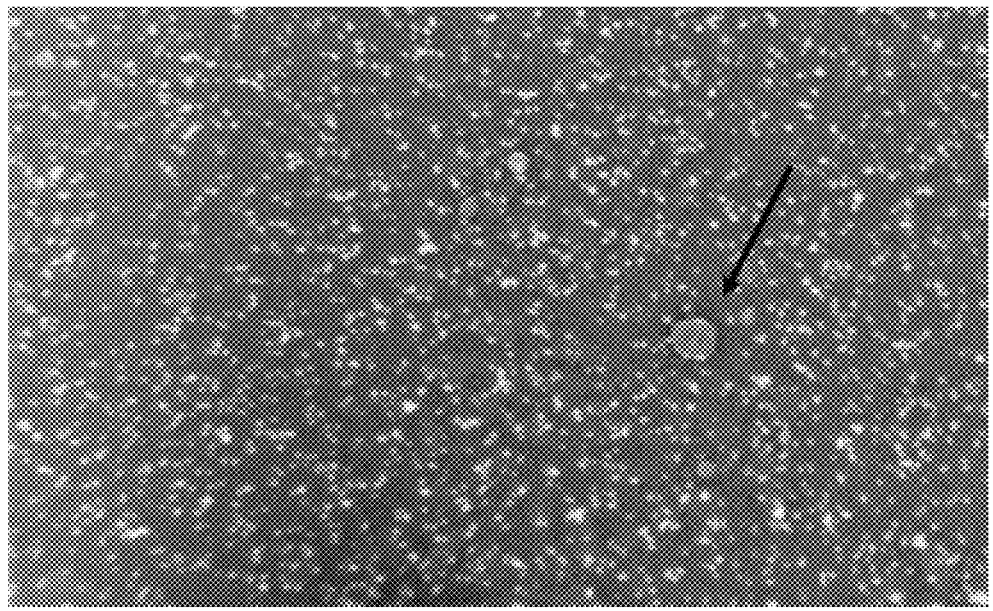
FIGS. 26A, 26B, and 26C depict human umbilical cord vascular endothelial cells (arrows) actively proliferating within the ECM derived by SMS cells (100×).
Figure 26B:
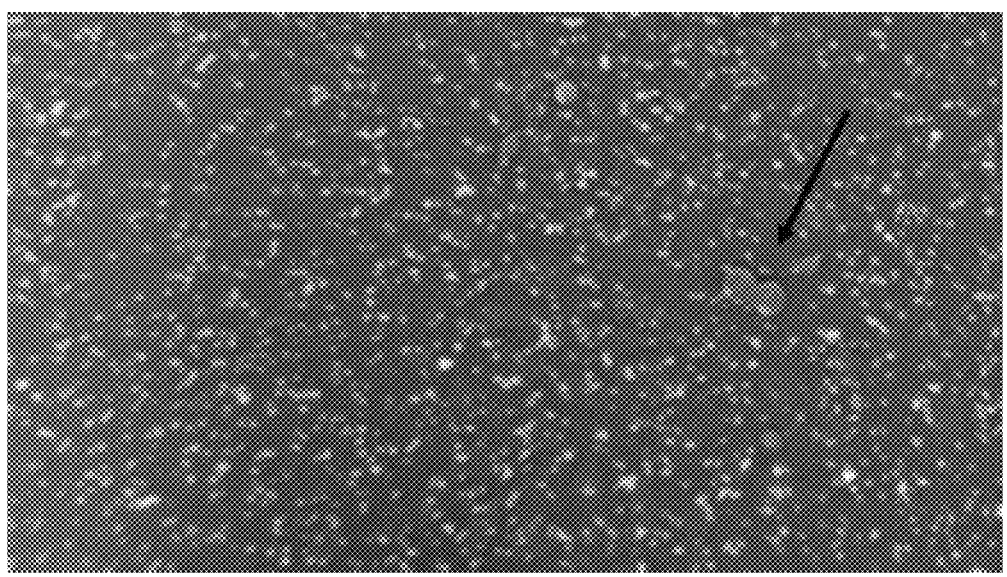
Figure 26C:
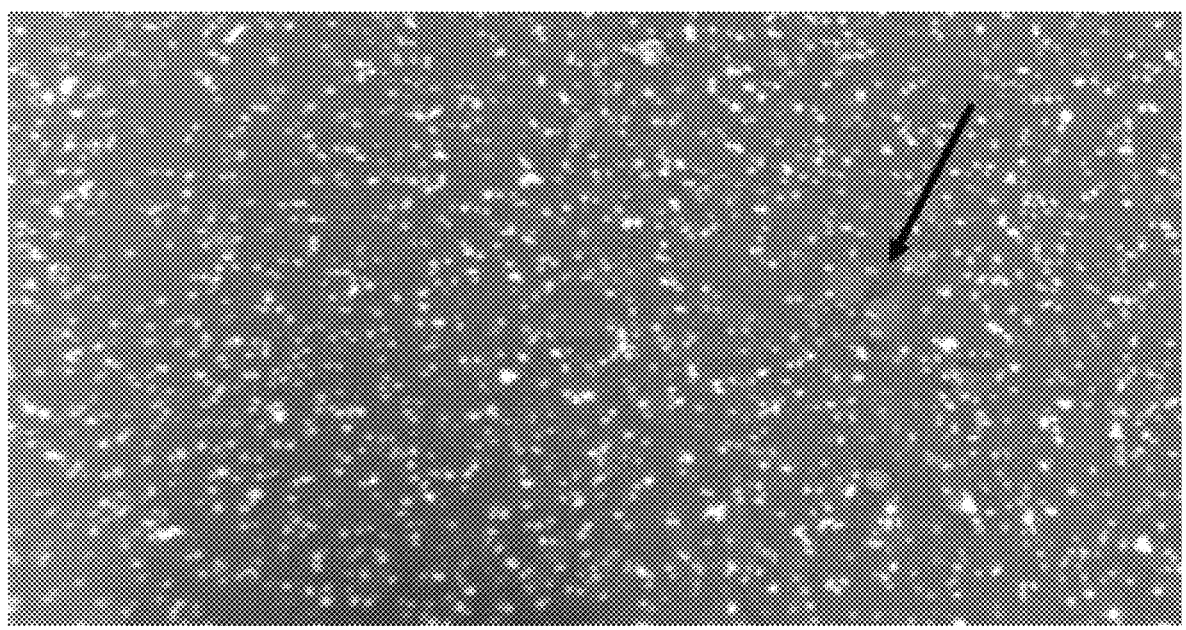
Figure 27A:
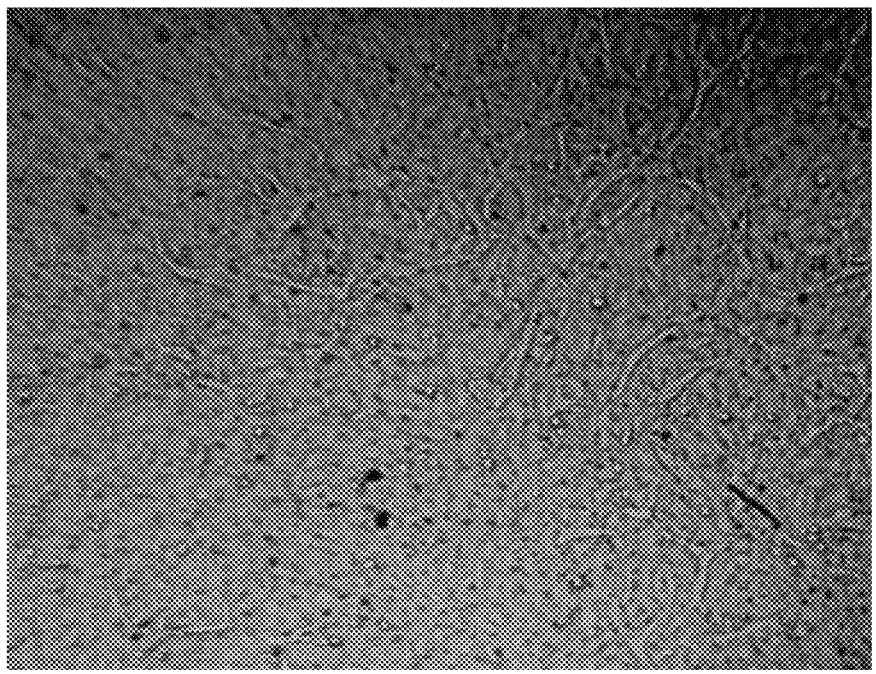
FIGS. 27A and 27B depict human umbilical cord vascular endothelial cells forming tubular structures within the ECM derived by SMS cells (100×).
Figure 27B:
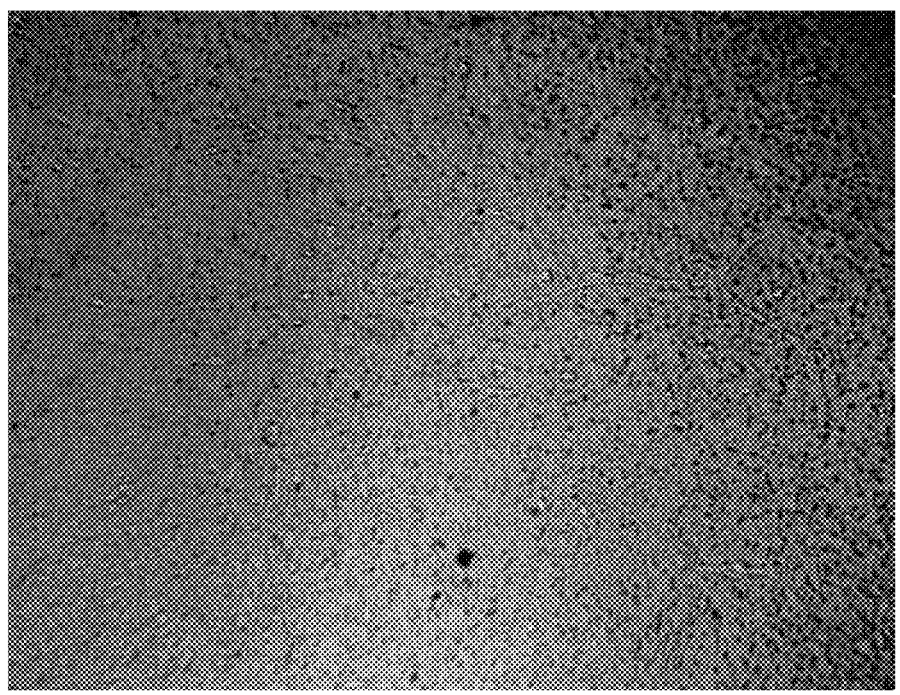
Figure 28A:
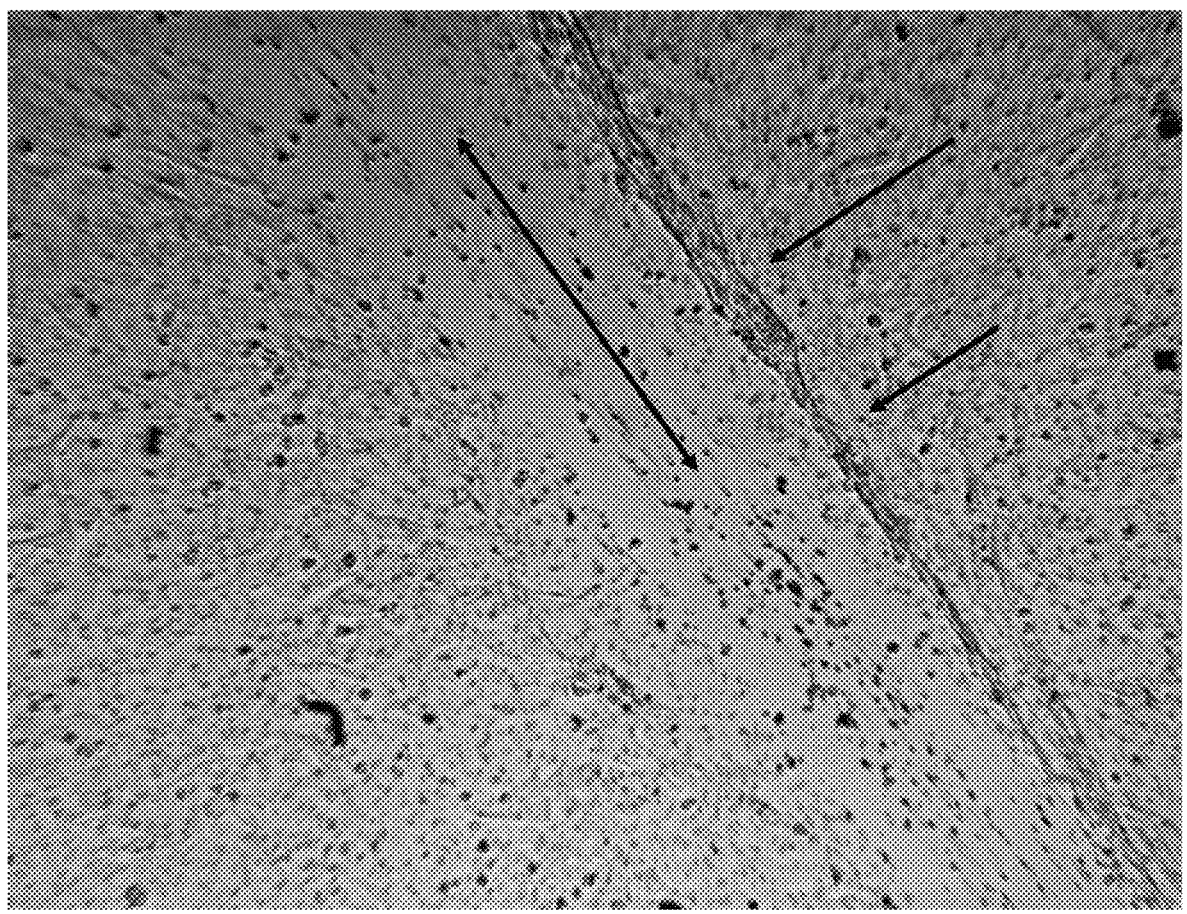
FIGS. 28A, 28B, and 28C depict human umbilical cord vascular endothelial cells (arrows) aligned in a wall like structure. The alignment appears to be guided by differential organization of the ECM derived by SMS cells. Endothelial cells are few to absent (double headed arrow) bordered by the aligned endothelial cells (arrows) (FIGS. 28A and 28C—100×.
Figure 28B:
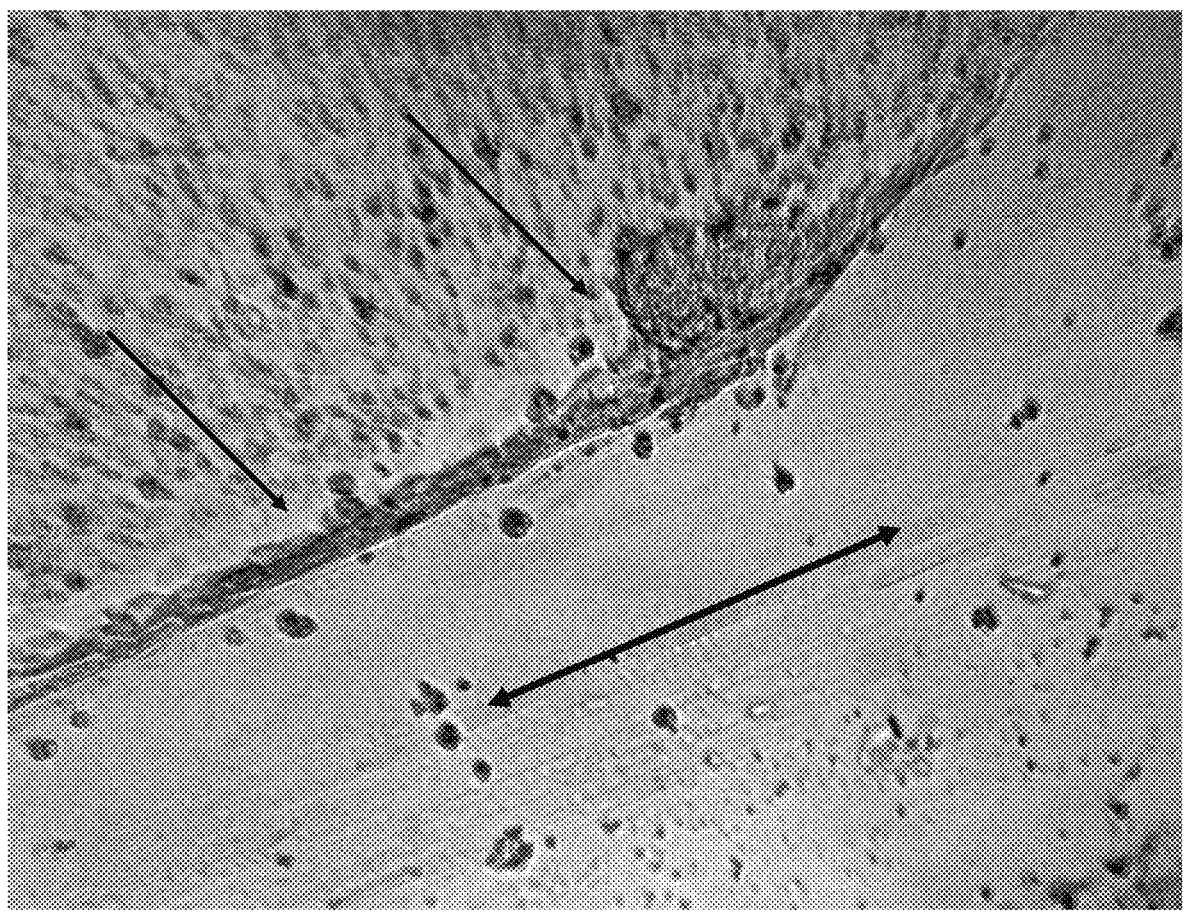
Figure 28C:
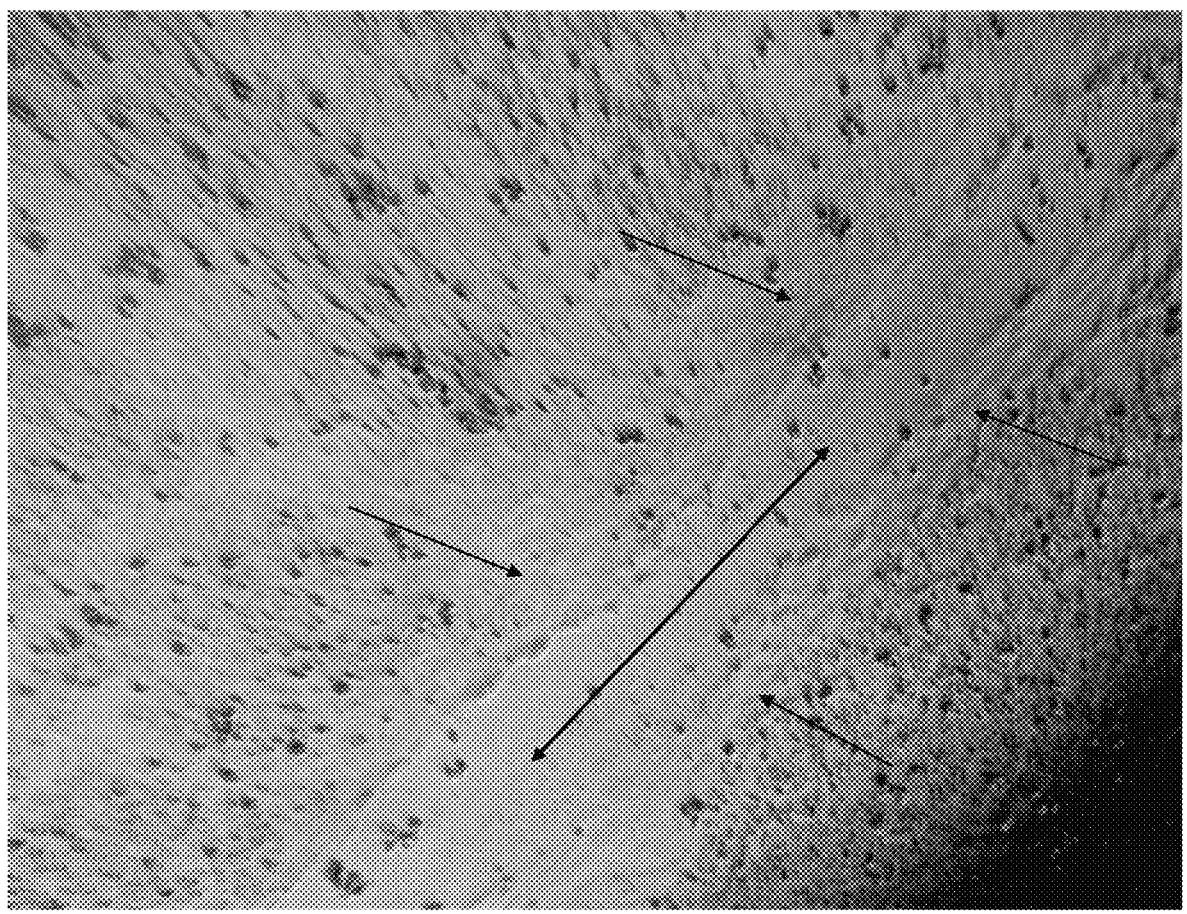
Figure 29A:
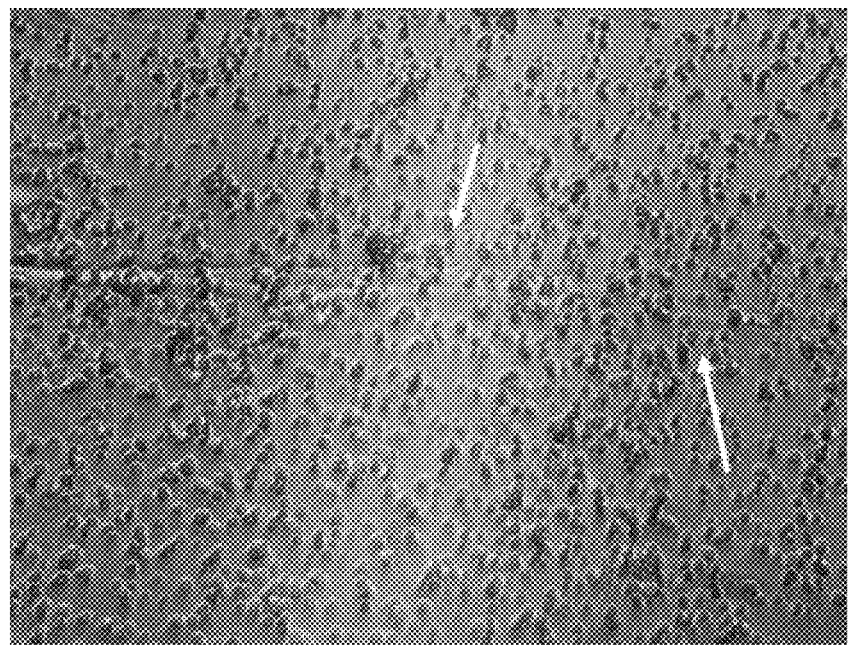
FIGS. 29A-29D depict human umbilical cord vessel endothelial cells forming a vessel with a firm anchorage into the adherent endothelial cell layer embedded with the ECM derived from SMS cells (FIG. 29A—200×.
Figure 29B:
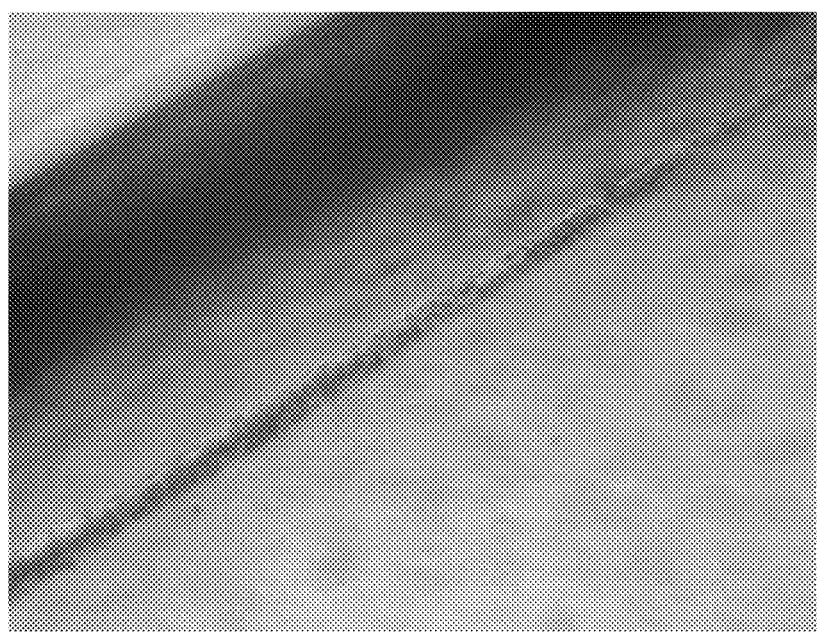
Figure 29C:
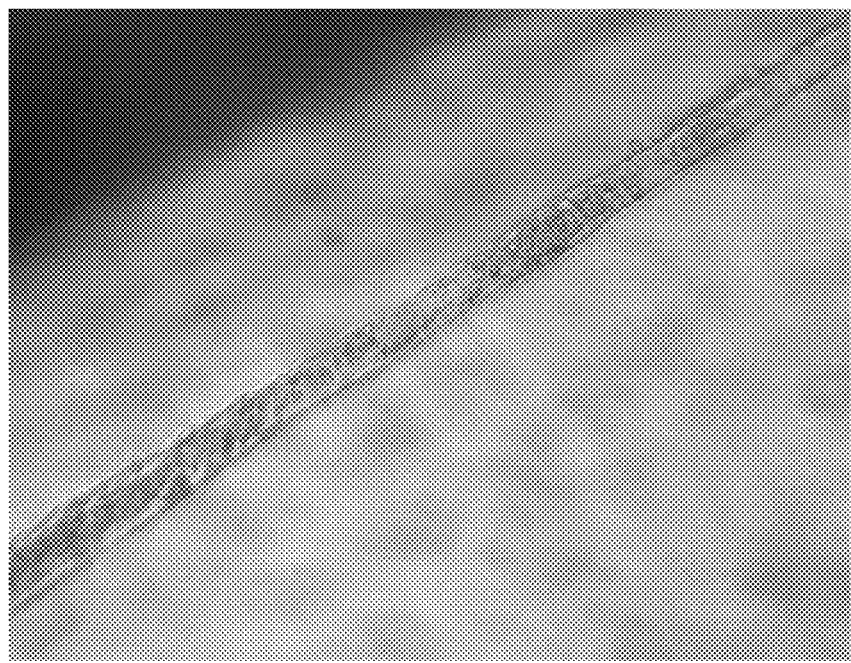
Figure 29D:
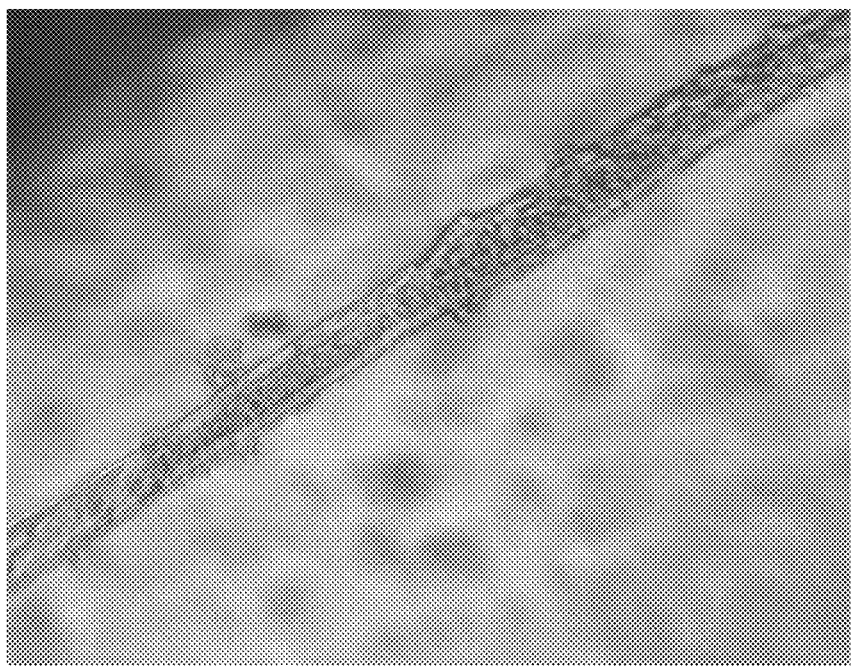

In some embodiments, endothelial cells are grown with and interact with SMS-derived ECM. In some embodiments, the endothelial cells migrate into the SMS-derived ECM (FIGS. 25A and 25B). In some embodiments, the endothelial cells actively proliferate within the SMS-derived ECMx (FIGS. 26A-26C). In some embodiments, endothelial cells differentiate into tubes and survived in that state for 1 day, 2 days, 3 days, 4 days, 5 days, 6 days, 1 week, 2 weeks, 3 weeks, 4 weeks, 1 month, 2 months, 3, months, 4 months, 5 months, 6 months, 9 months, 1 year, or longer, or a duration within a range defined by any two of the aforementioned durations. (FIGS. 27A and 27B). In some embodiments, the endothelial cells formed transiently aligned cells along the edges of aligned SMS cells with endothelial cells largely absent at the core between borders, which is reminiscent of larger tubular (vessel) structures (FIGS. 28A-28C).

Figure 30A:
FIGS. 30A and 30B depict human keratinocytes adhering to the surface of the SMS derived ECM presenting a typical confluent layer of cells (FIG. 30A—100×.
Figure 30B:

In some embodiments, keratinocytes are grown with and interact with SMS-derived ECM. In some embodiments, keratinocytes form an adherent layer on top of SMS-derived ECM (FIGS. 30A and 30B). In some embodiments, this structure of keratinocytes with SMS-derived ECM remained stable for 1 day, 2 days, 3 days, 4 days, 5 days, 6 days, 1 week, 2 weeks, 3 weeks, 4 weeks, 1 month, 2 months, 3, months, 4 months, 5 months, 6 months, 9 months, 1 year, or longer, or a duration within a range defined by any two of the aforementioned durations.

Figure 31A:
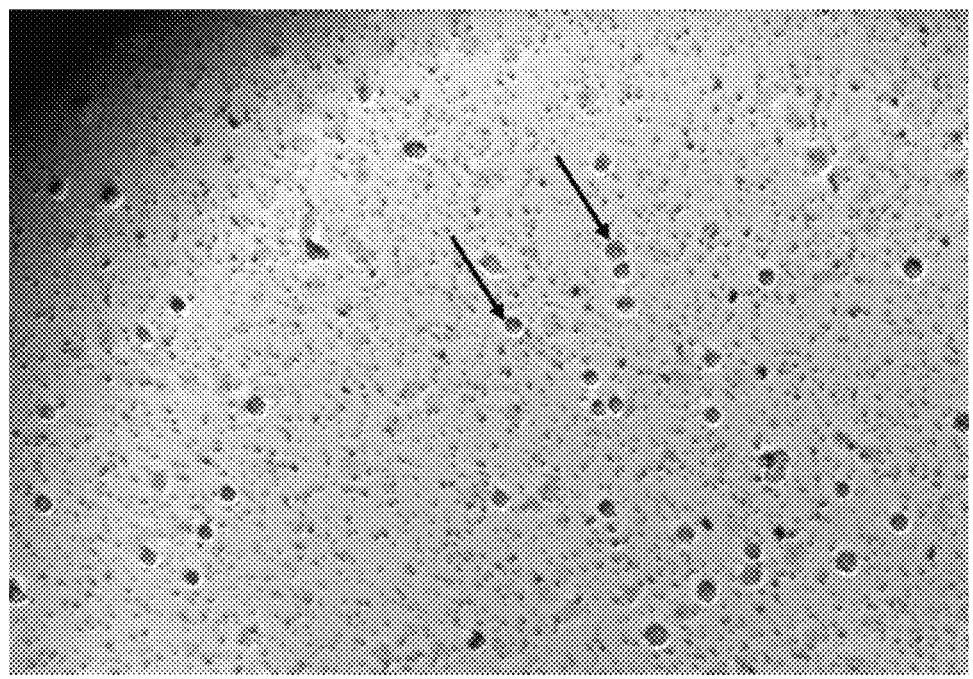
FIGS. 31A and 31B depict human skin fibroblast cells (arrows) migrating into the ECM derived by SMS cells (100×).
Figure 31B:
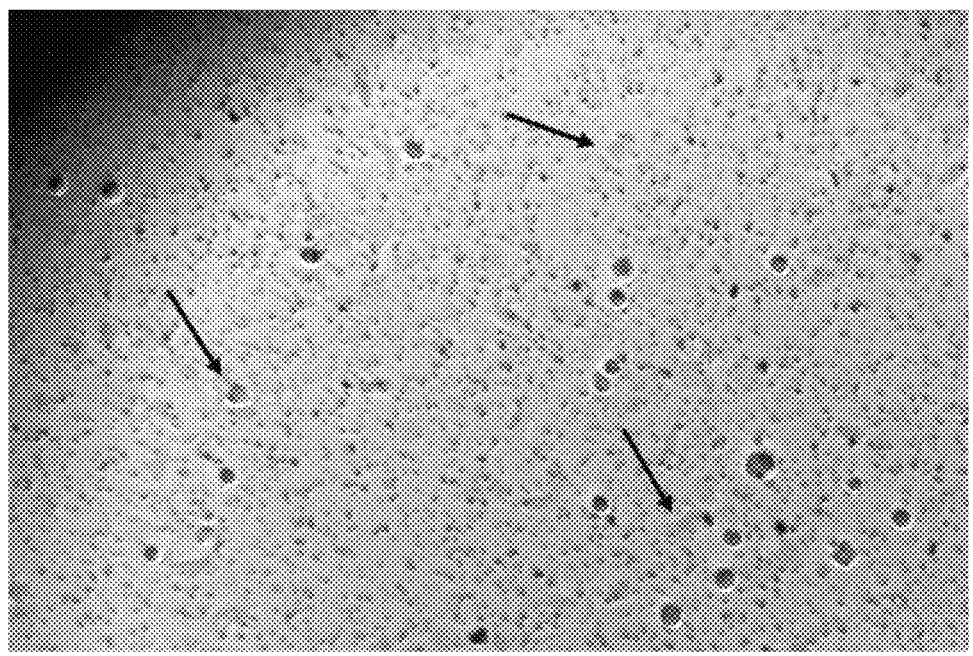
Figure 32A:
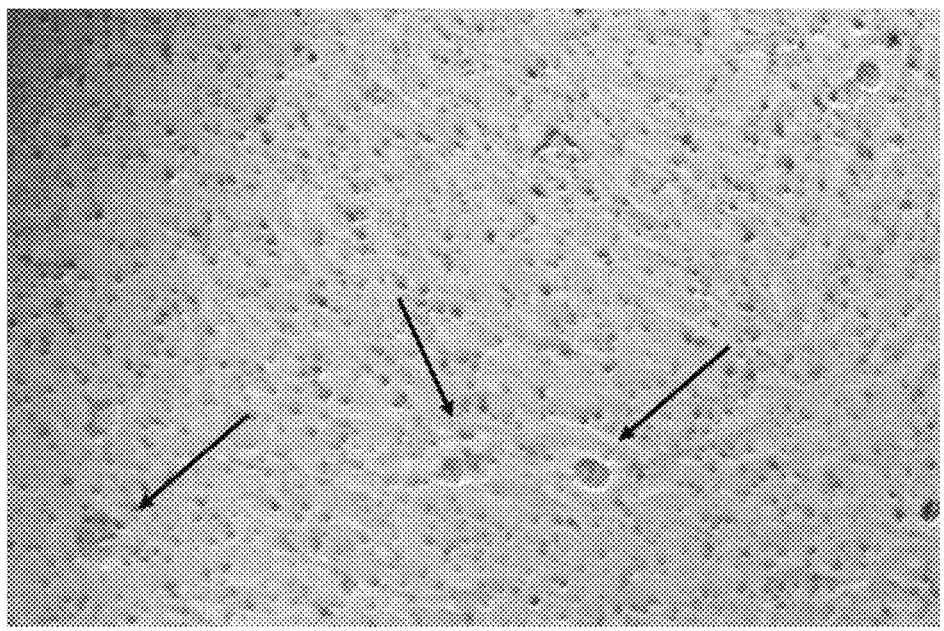
FIGS. 32A and 32B depict human skin fibroblast cells (arrows) actively proliferating within the ECM derived by SMS cells (100×).
Figure 32B:
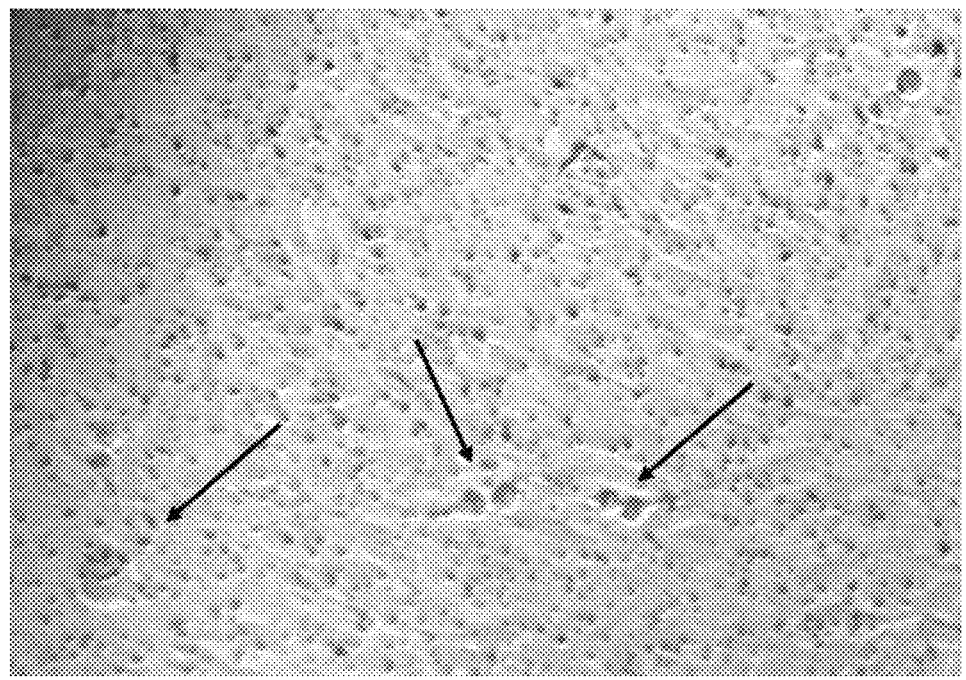

In some embodiments, fibroblast cells are grown with and interact with SMS-derived ECM. In some embodiments, the fibroblast cells migrate into SMS-derived ECM (FIGS. 31A and 31). In some embodiments, fibroblast cells migrate and proliferate within the matrix (FIGS. 32A and 32B). In some embodiments, fibroblast cells reach confluency in few days. In some embodiments, fibroblast cells survived within SMS-derived ECM for 1 day, 2 days, 3 days, 4 days, 5 days, 6 days, 1 week, 2 weeks, 3 weeks, 4 weeks, 1 month, 2 months, 3, months, 4 months, 5 months, 6 months, 9 months, 1 year, or longer, or a duration within a range defined by any two of the aforementioned durations.

In some alternatives, the ECM is also decellularized (e.g., by using a chemical, physical, and/or enzymatic approach). Preferably, a decellularization approach is configured such that the ECM scaffold maintains its structural and chemical integrity. In addition, various molecular components of the SMS derived ECM can be enriched or isolated. ECM in various tissues of various organs can be shown to be similar or identical to ECM from in vitro SMS cell culture. The ECM produced by the aforementioned SMS cells may be freeze dried into powder and stored as such. ECM in powder or other form is capable of being used for various applications such as promoting cell growth or cell differentiation in vitro (such as for 3D cell culture) or in vivo (such as in promoting wound healing) (or inhibiting tumor growth).

In some alternatives, ECM is produced by SMS cells growing on a scaffold. SMS cells are cultured on various scaffolds (e.g., native decellularized bone, soft decellularized collagen, a carbon support, such as an activated carbon, carbon black, a carbon film, a carbon cloth, nanotube, or microtube or a medical device or implant composed of carbon such as a stent or shunt) in a suitable growth medium (e.g., DMEM with or without serum). In some alternatives, the support is free-floating in the growth medium. Differentiation induction compounds may be added. Microscopic observation indicates that the SMS cells change shape drastically after differentiation, and the SMS cell differentiation varies depending on the nature of the scaffold and/or the type of differentiation compound added. SMS cell attachment, growth, and differentiation is influenced by varying the medium. SMS cells and cells derived from it produce extracellular matrix and tissue like structures attached to the scaffolds.

Produced ECM and tissue-like structures including SMS cells or made by SMS cells are favorable to nutrient access because they are highly porous as a result of the formation of various tubular structures. Cells and derivatives attached remain vital for months in culture medium (37° C. and 5% $CO_2$). SMS cells, cells derived from it, SMS-produced ECM, and structures thereof, attached to various scaffolds, can be used to enhance the biocompatibility and shorten the healing process of implanted scaffolds.

Structured scaffolds can also be produced de novo with SMS cells. SMS cells have a proclivity of organizing and positioning themselves in an ordered fashion during in vitro cell culture. After suitable molecular induction, SMS cells produce scaffolds that are well structured and can generate 3D bodies with pertinent geometric shapes. In some alternatives, SMS cells grown in suspension are incubated using an inductive medium in a polystyrene plate. After biweekly medium addition for about three weeks different scaffolds appear with various shapes. Accordingly, aspects of the invention described herein concern a three dimensional body generated from SMS cells (e.g., SMS cells in suspension culture with or without a scaffold, such as a carbon-based scaffold, including activated carbon, carbon black, a carbon film, a carbon cloth, nanotube, or microtube or a medical device or implant composed of carbon such as a stent or shunt).

Some alternatives concern the production of a soft tissue culture from peripheral blood. By this approach, peripheral blood (containing the anti-coagulate ACD) is centrifuged at low speed and the supernatant is removed. SMS cells are added to the pellet and the mix is cultured using growth medium in a suitable vessel (e.g., plate or flask). At the bottom of the vessel, a gel containing SMS cells forms, and this gel includes white and red blood cells. The gel can be removed from the flask, and washed (e.g., twice using Hanks' buffer) and the gel is frozen (e.g., at −20° C. or −70° C.). After several days the frozen gel can be removed from the freezer and thawed. Thawed gel can be washed several times using phosphate buffer solution (PBS) to remove most white blood and red blood cells, which are destroyed by the freeze/thaw cycle, whereas SMS cells are unaffected. Accordingly, some alternatives include a gel including SMS cells, white blood cells, and red blood cells and uses of this gel as an implant in the body. Preferably the gel being implanted is autologous in that it is prepared from peripheral blood from an individual that will become the recipient of the implant. The gel can also be incubated with a growth medium under standard conditions, and over time, the gel becomes gradually more sturdy and tissue-like. The tissue-like structures generated are organized and have tubule and capillary like structures.

SMS cells are also grown on a variety of substrates or surfaces in some alternatives. SMS cells can be grown on, e.g., a flask, container, chamber, channel, tube, vessel, niche, or bioreactor, wherein the surface of the flask, container, chamber, channel, tube, vessel, niche, or a bioreactor, which can be pretreated with etched surfaces of geometric shapes. The surface of these substrates may be pretreated with a chemical or physical treatment, including, for example, the use of borosilicate, mechanical abrasion, blasting, silicon carbide, solvent, acid, anodizing, the application of a carbon film such as carbon evaporation e.g., on a desired geometric shape. The pretreatment can provide a geometric shape or greater porosity on the surface of the vessel e.g. a flask, container, chamber, channel, tube, vessel, niche, or bioreactor. The geometric shape can include, for example, one or more line, curve, web, groove, ridge, or other shape. SMS cells deposited or introduced to the pretreated flask, container, chamber, channel, tube, vessel, niche, or bioreactor organize about the geometric shape, using the shape as a guide for the organization of cell culture growth.

In some alternatives, SMS cells are provided in a microfluidic device. SMS cells (and cells derived thereof) are introduced on a lab-on-a-chip device (e.g., a device that integrates one or several laboratory functions on a single chip that deals with handling particles in hollow microfluidic channels). In some alternatives, the SMS cells are used in a device (e.g., a multi-channel 3D microfluidic cell culture chip that simulates the activities, mechanics and physiological response of entire organs and organ systems) so as to evaluate the influence of a drug or medicament or treatment protocol. Accordingly, in some approaches, SMS cells are provided in a microfluidic device and a drug or medicament is provided to the microfluidic device in a manner that allows for contact of the drug or medicament with the SMS cells. Physiologic changes or morphologic changes of the SMS cells can be evaluated. In some alternatives, a subject for evaluation is identified, SMS cells are isolated from said subject's peripheral blood, and the SMS cells are contacted with a compound, drug, medicament or treatment protocol, e.g., by placing the SMS cells in a microfluidic device and introducing the compound, drug, medicament or treatment into the device such that the compound, drug, medicament or treatment contacts the SMS cells. Physiologic and/or morphologic and/or diagnostic evaluation of the SMS cells before, during and/or after contact with the compound, drug, medicament or treatment can be performed.

Resilient SMS cells may make the microfluidic chip applications more accessible (shelf life and expense, potential for differentiation, production of specific molecules). After being preserved in their undifferentiated form (the resilient form) cells integrated in the microfluidic circuits may be induced to exert a specific function or to differentiate, this may occur selectively, position based, via engineered channels that will provide to cells, occupying specific locations within the chip, so called "chambers", selective chemical inducers or other topical inducers (such as temperature, surface constitution, or pressure) converting cells at selective positions to desired function and used at that stage).

The invention is generally disclosed herein using affirmative language to describe the numerous embodiments. The invention also includes embodiments in which subject matter is excluded, in full or in part, such as substances or materials, method steps and conditions, protocols, or procedures.

EXAMPLES

Some aspects of the embodiments discussed above are disclosed in further detail in the following examples, which are not in any way intended to limit the scope of the present disclosure. Those in the art will appreciate that many other embodiments also fall within the scope of the invention, as it is described herein above and in the claims.

Example 1

Growing SMS Cells in Suspension with the Prevention of Differentiation

The following example demonstrates a method for growing SMS cells in an undifferentiated state for prolonged periods.

Small mobile stem (SMS) cells are grown in T25 flask using growth medium (37° C. and 5% $CO_2$). The SMS cell population may contain a heterogeneous cell population of undifferentiated SMS cells and SMS derived differentiated cells.

SMS undifferentiated cells are present as a floating and adherent fraction, as shown in FIG. 1. The floating fraction is predominantly undifferentiated SMS cells.

Floating undifferentiated SMS cells, distinguishable through their unique characteristic morphology, as explained previously, are obtained from the medium of the SMS cells grown in T25 flask.

Undifferentiated SMS cells can be isolated by differential centrifugation, removing clumps of cells or differentiated cells at low centrifugation speed followed by centrifuging undifferentiated SMS cells at high speed. Alternatively, the undifferentiated cells may be isolated by filtration, including differential filtration using filters having progressively smaller pore sizes to a pore size of 3-5 μm. The isolated undifferentiated SMS cells are examined under the microscope for homogeneity.

Undifferentiated SMS cells are grown in polypropylene tube (such as the bioreactor tubes: 15 ml provided by the manufacturer Techno Plastic Products AG, TPP).

The following example of growth medium is used: high sugar basal medium (Dulbecco's Modified Eagle Medium (DMEM), [+] 6 g/L D-glucose, [−] sodium pyruvate, [−] L-glutamine, [−] Phenol red), to which 1% GlutaMAX™-I (100×), 10% calf serum, and 5 μg/mL human insulin was added. Alternatively a medium not containing any calf serum can be used. The cells are suspended occasionally by swirling.

Complete medium is replaced every week by centrifuging the SMS cells at 4200 g for 15 min. The centrifugation may be varied at 3000 g, 3500 g, 4000 g, 4100 g, 4200 g, 4300 g, 4500 g, or 5000 g or by centrifugation at a speed that is within a range defined by any two of the aforementioned speeds, and the time adjusted accordingly.

Figure 2:
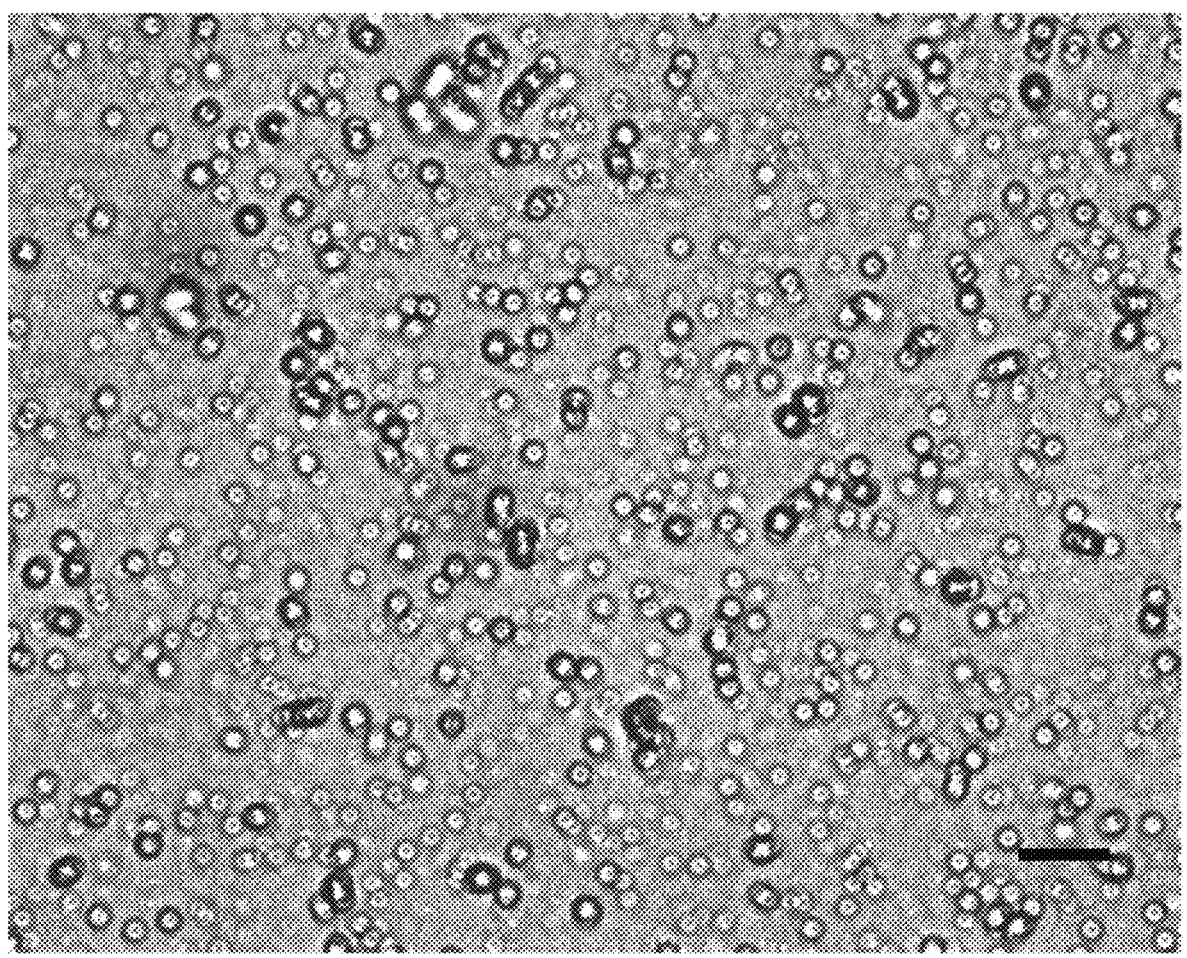
FIG. 2 is a digitally enhanced microscope image depicting undifferentiated SMS cells obtained by isolation from the floating T25 cultured fraction and culturing in suspension (400×; bar=15 μm).
Figure 3:
FIG. 3 shows SMS cell cultures centrifuged at 4200 g for 15 min. The SMS cells were cultured in the bioreactor polypropylene tubes shown in the figure in a high glucose DMEM medium, in the absence of serum (left) and in the presence of serum (right) (10 mL each). Both cultures following centrifugation produced a large pellet, with a slight difference in pellet shape. The supernatant for each culture following centrifugation is clear.
Figure 4:
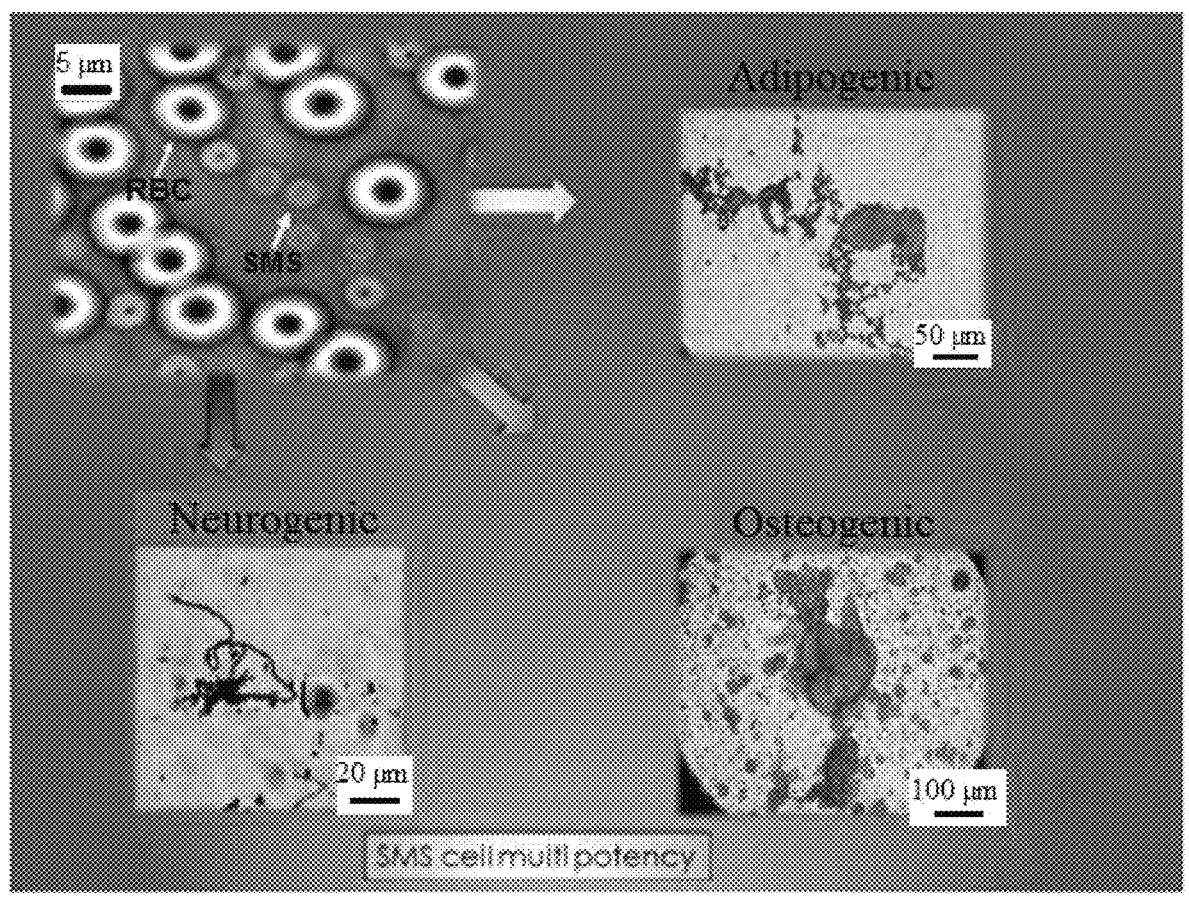
FIG. 4 depicts that SMS cells cultured in T25 flasks may be differentiated into multiple cell lines following neurogenic, osteogenic, and adipogenic induction.
Figure 5:
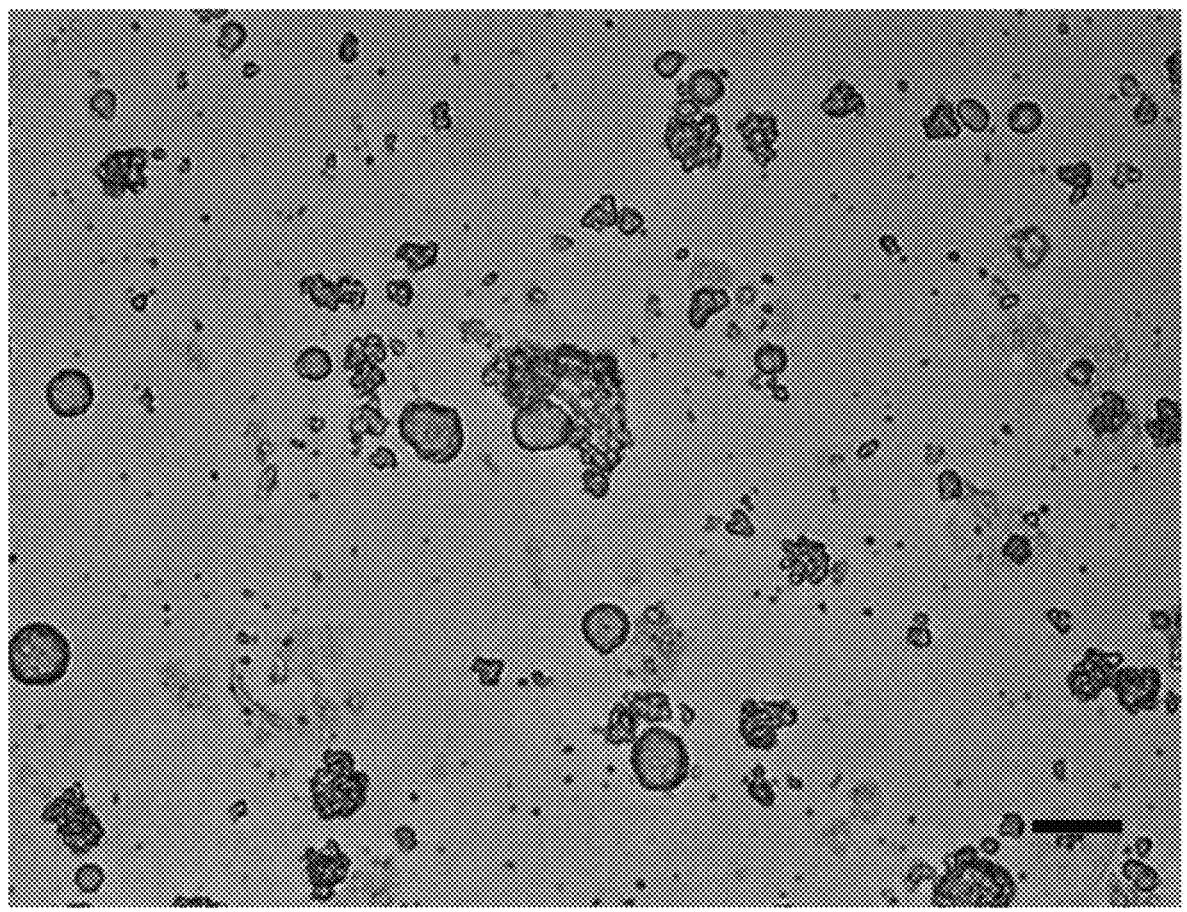
FIG. 5 depicts differentiated SMS cells cultured in a 6 well plate in an osteogenic inductive medium. The SMS cells differentiated into osteogenic cell lines that are several times the original size of undifferentiated SMS cells (200×; bar=30 μm).
Figure 6:
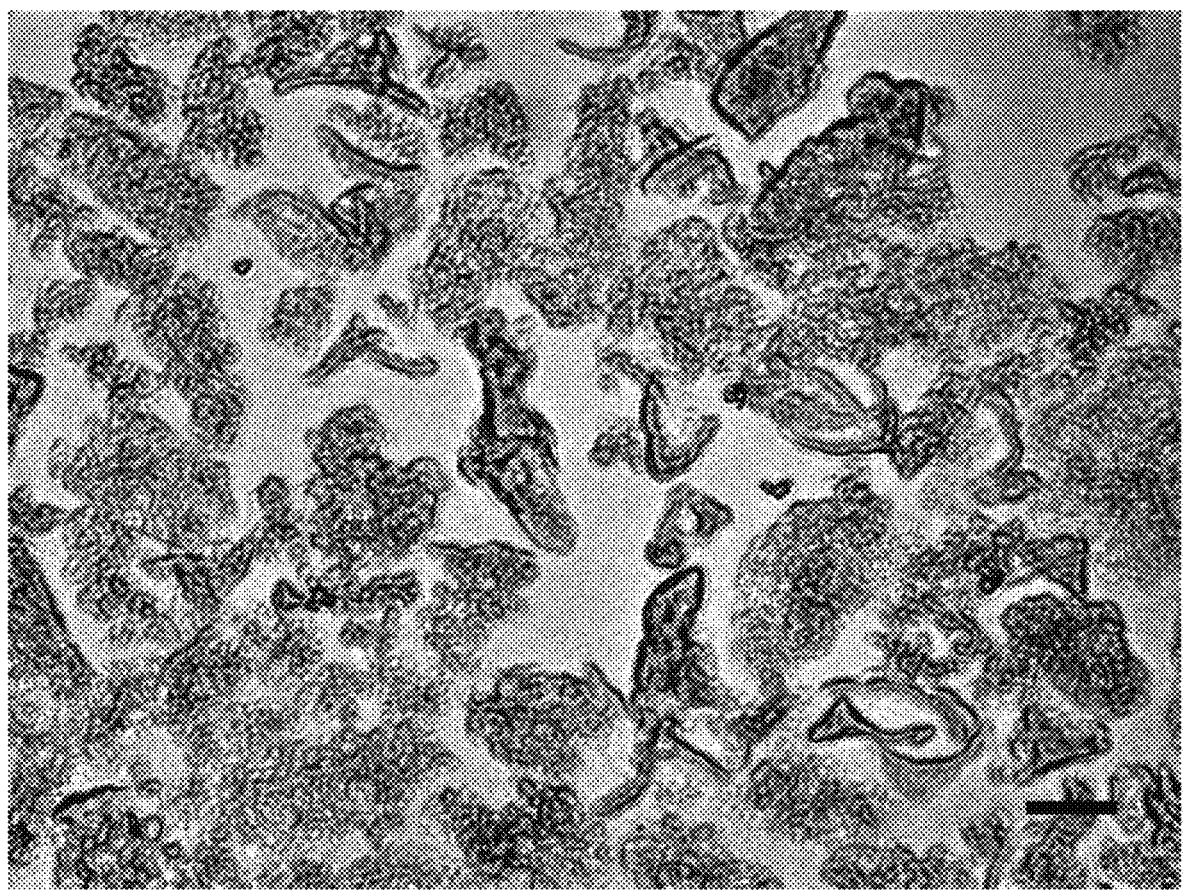
FIG. 6 depicts differentiated SMS cells cultured in a 6 well plate in an osteogenic inductive medium. The SMS cells differentiated into osteogenic cell lines (400×; bar=15 μm).
Figure 7:
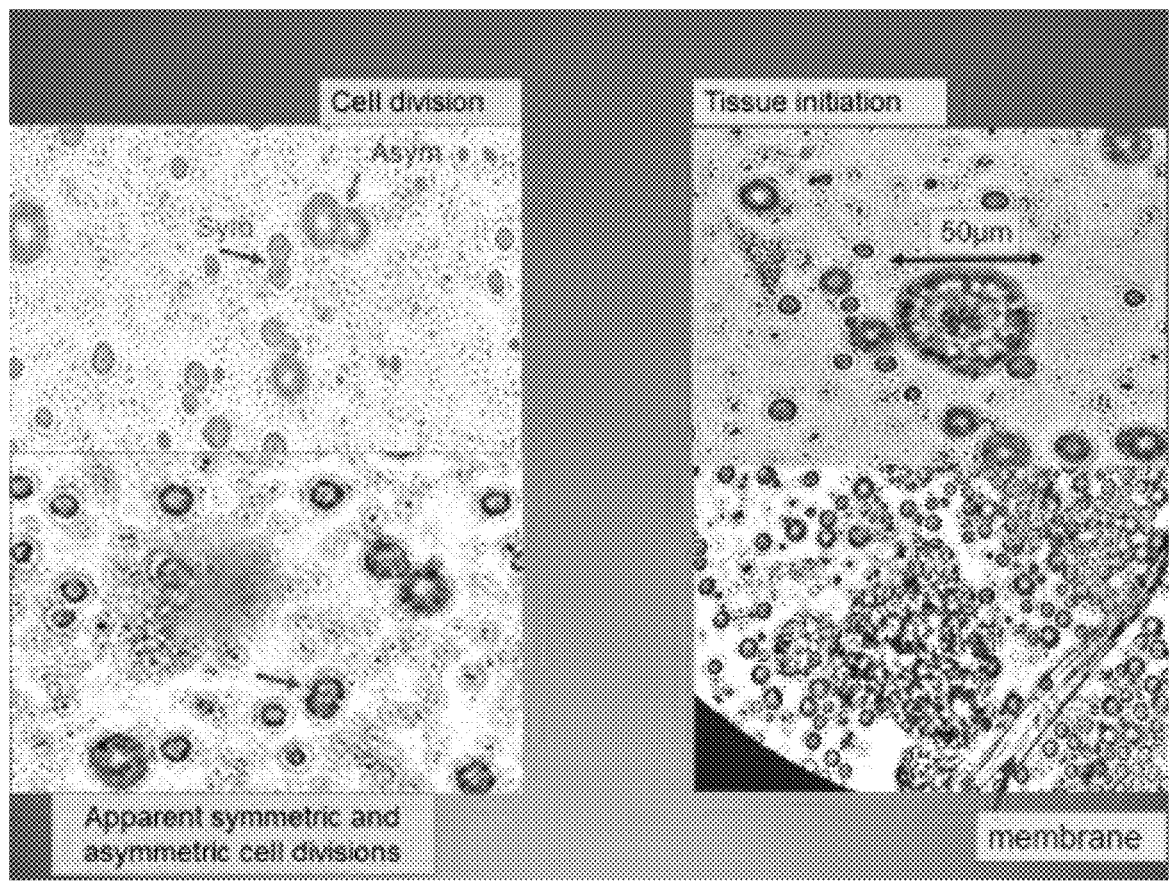
FIG. 7 illustrates the drastic changes in SMS cell morphology after changes in culture condition. The co-presence of SMS cells and the enlarged cells can be seen. Both cell types are actively dividing, some undergoing asymmetric division.

Under these conditions the volume size of the medium (cell crowdedness) is growth limiting to SMS cells. The SMS cell homogeneity is assessed microscopically (see FIG. 2) and the SMS cell count is estimated by assessing spectroscopically turbidity of the suspension and/or by measuring the size of the pellet after centrifugation at high speed (see FIG. 3).

The SMS cell growth potential is assessed by inoculating cells into a new tube with growth medium. SMS cells grow mainly as individual cells not as clumps and remain under this condition mainly undifferentiated. The suspension culture is scalable such that increasing the volume of the medium increases the number of cells obtained (see FIG. 3).

Example 2

Use of SMS Cells for the Production of Molecules

Undifferentiated SMS cells have a variety of applications. This example shows that SMS cells may be differentiated into a variety of cell types.

As shown in Table 1 below, and in the appropriate figures (FIG. 4-13), SMS cells are capable of differentiating into a variety of cell types.

TABLE 1

Small Mobile Stem Cell Differentiation Conditions and Cell Types

| Differ-entiated Cell product number | Flask | Induction conditions | Resulting observed differ-entiation | FIG. |
|---|---|---|---|---|
| 1 | T25 | Neurogenic medium: 1 mM β-mercaptoethanol (BME) was added to DMEM + 10% FBS medium for 24 h. Cells were washed with D-Hanks buffer solution three times, and treated with DMEM, 2% DMSO and 200 μM butylated hydroxyanisole. | Neuronal cells | 4 |
| 2 | T25 | Adipogenic medium: DMEM + 10% FBS, 1 μmol/L dexamethasone, 5 μg/mL insulin, 0.5 μmol/L isobutylmethylxanthine, and 60 μmol/L indomethacin. | Adipocytes | 4 |
| 3 | T25 | Osteogenic medium: DMEM + 10% FBS, 0.1 μmol/L dexamethasone (Sigma), 0.05 mmol/L ascorbic acid-2-phosphate (Sigma) and 10 mmol/L β-glycerophosphate. | Osteocytes | 4 |
| 4 | 6 Well Plate | Osteogenic medium: Mesenpro ™ basal medium (no supplement) + GlutaMAX ™ + 10% FBS (or 10% CS), 0.1 μmol/L dexamethasone (Sigma), 0.05 mmol/L ascorbic acid-2-phosphate (Sigma) and 10 mmol/L β-glycerophosphate. | Osteocytes and bone scaffold | 5; 6 |
| 5 | 6 Well Plate | Mesenpro ™ basal medium (no supplement) + GlutaMAX ™ + 10% calf serum | Large suspended round dark cells with slightly rough edges | 7 |
| 6 | 6 Well Plate | Mesenpro ™ basal medium (no supplement) + GlutaMAX ™ | Large adherent round smooth edges forming Cuboidal floating epithelial cells | 8A; 8B |
| 8 | 6 Well Plate | Mesenpro ™ basal medium (no supplement) + | Large suspended round cells, slightly | 9A; 9B |

TABLE 1-continued

Small Mobile Stem Cell Differentiation Conditions and Cell Types

| Differentiated Cell product number | Flask | Induction conditions | Resulting observed differentiation | FIG. |
|---|---|---|---|---|
| | | GlutaMAX ™ + 10% calf serum | protruding edges with transparent cytoplasm | |
| 9 | 6 Well Plate | Mesenpro ™ basal medium (no supplement) + GlutaMAX ™ + 10% calf serum | Large floating round cells with transparent cytoplasm | 10 |
| 10 | 6 Well Plate | Mesenpro ™ basal medium (no supplement) + GlutaMAX ™ + 10% calf serum | Large floating flat irregular shaped cells with extensions and transparent cytoplasm | 11 |
| 11 | 6 Well Plate | Stempro ™ basal medium (no supplement) + GlutaMAX ™ + 10% calf serum | Large round smooth edges adherent cells consistent shape with transparent cytoplasm | 12 |
| 12 | 6 Well Plate | Mesenpro ™ basal medium (no supplement) + GlutaMAX ™ + 1-5% DMSO | Large adherent flat cells with irregular shape and extensions | 13A; 13B; 13C |

SMS cell functionality is assessed by testing differentiation capacity of SMS cells using the various assays described in Table 1 that include suitable inductive media in polystyrene plates (T25 flasks and 6 well plates).

In addition, native or genetically modified SMS cells can be used to produce various small and large compounds including but not restricted to proteins. SMS cells can be used for various applications such as differentiation into other cells, formation of tissues or tissue like structures, organoids or organs.

Furthermore, SMS cells can be applied as a substrate for the process of generating spatially-controlled cell patterns using 3D printing (3D bioprinting). This can be achieved by using a 3D bioprinter, which includes, for example, Bio-Bot1®, 3D-Bioplotter®, 3DS Alpha®, and 3Dynamic Omega®.

Figure 14A:
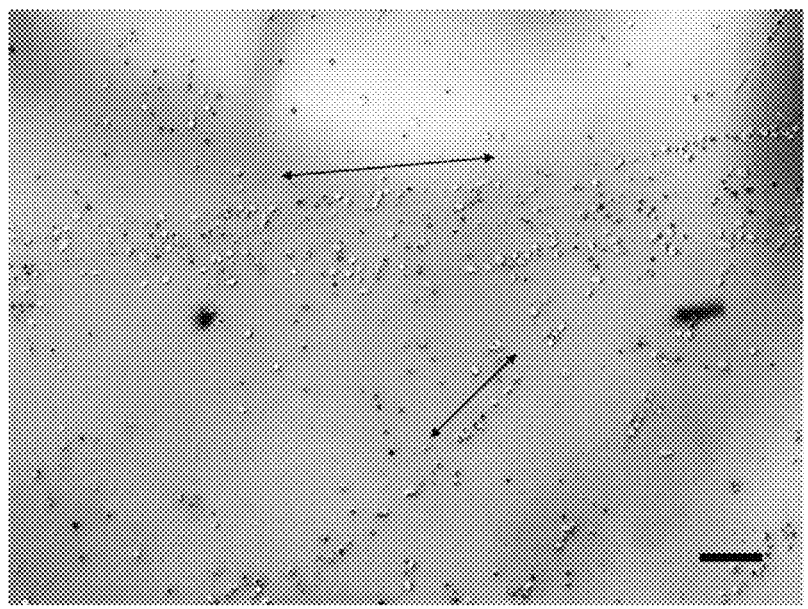
FIG. 14A depicts SMS cells co-cultured with fibroblast cells (same source) in a T25 flask. The alignment of the larger fibroblasts is apparently directed by the aligned SMS cells (40×; bar=150 μm).
Figure 14B:
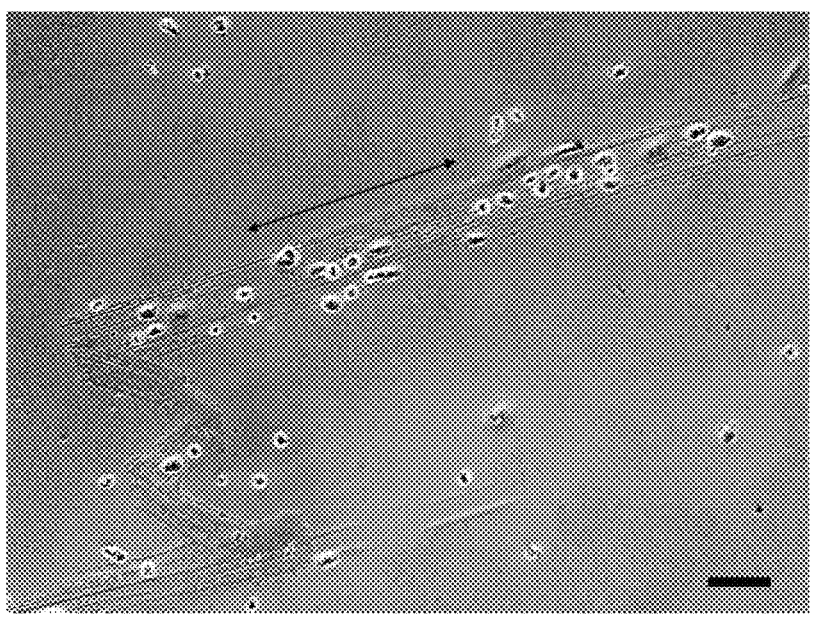
FIG. 14B depicts SMS cells co-cultured with fibroblast cells (same source) in a T25 flask. The alignment of the larger fibroblasts is apparently directed by the aligned SMS cells (40×; bar=150 μm).
Figure 15:
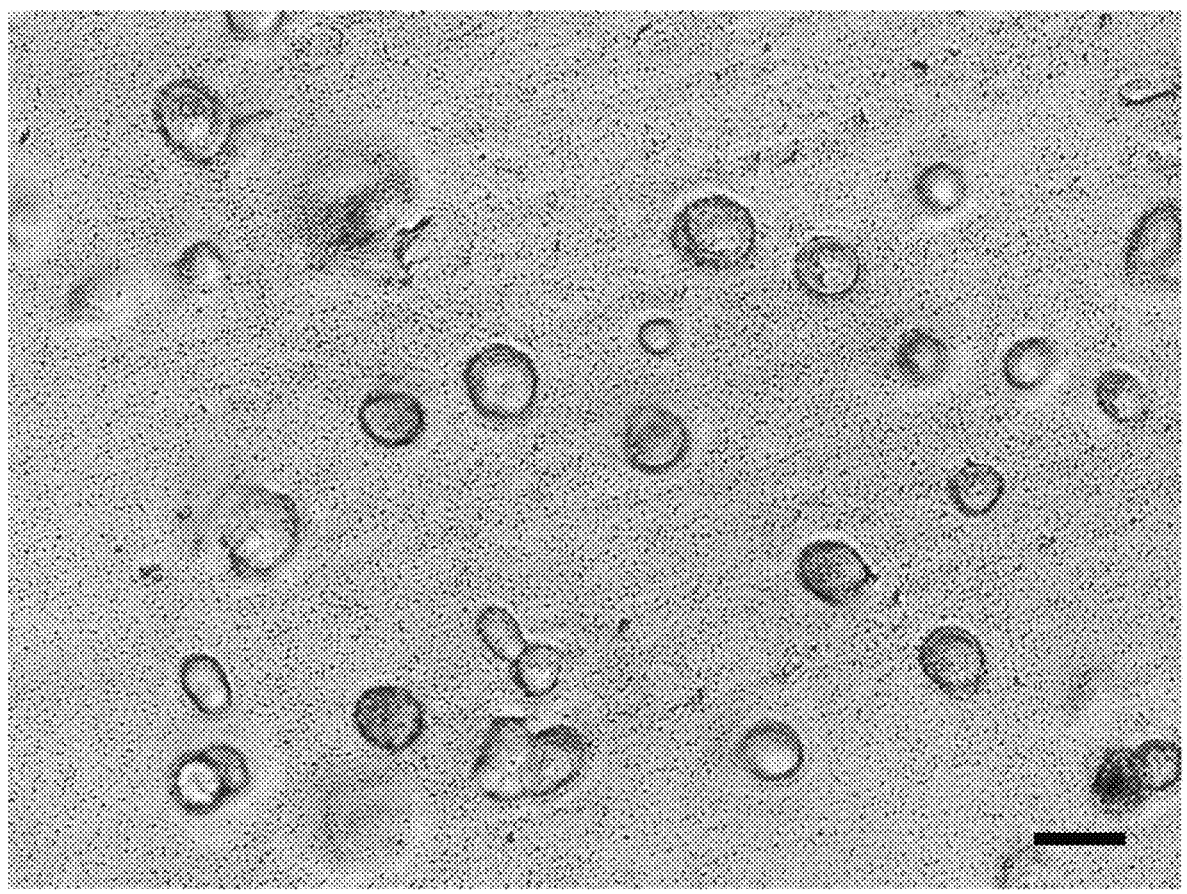
FIG. 15 depicts SMS cells co-cultured with fibroblast cells (same source) in a T25 flask. The alignment of the larger fibroblasts is apparently directed by the aligned SMS cells (400×; bar=15 μm).

In addition, genetically modified SMS cells (containing a marker) can be used to trace cellular interactions, differentiation and other cell based activities, as shown in FIGS. 14A and 14B and FIG. 15.

Example 3

Production of Extracellular Matrix in Culture Flask

This example demonstrates the procedure for producing extracellular matrix (ECM) in culture flask using SMS cells.

SMS cells are grown in suspension under optimal proliferation non-differentiating condition, as described in Example 1. The SMS cell culture medium is switched by centrifuging the cells at high speed (for example, at 4200 g for 15 min) and suspending in a new growth medium.

SMS cells are seeded on T25 or plates (polystyrene; physical surface inducers) and grown using a growth medium (37° C. and 5% $CO_2$). Chemical inducers of ECM production are provided to the medium, including, for example, a hedgehog inhibitor and a TGF/BMP activator, at growth conditions (37° C. and 5% $CO_2$). The complete medium is added or replaced twice weekly.

Figure 16:
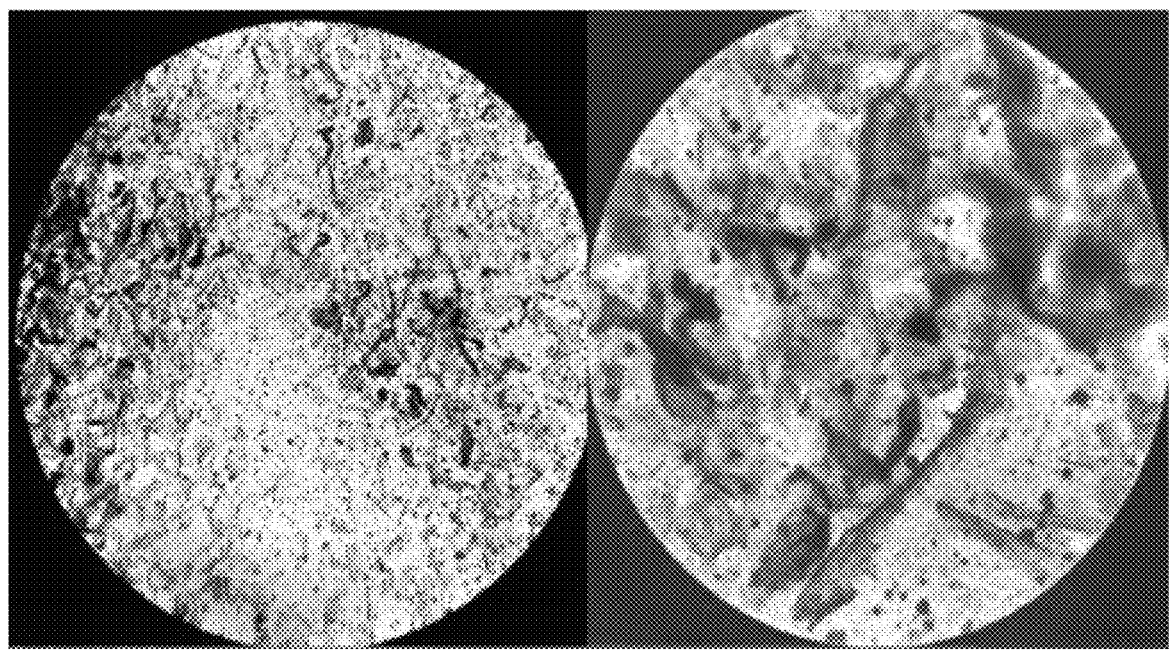
FIG. 16 depicts extracellular membrane formation promotion from SMS cells using a hedgehog antagonist (left, 100×; right, 400×). The hedgehog antagonist results in the production of large and diverse amounts of extracellular matrix as a consequence of cell signaling control.

After about two weeks, floating ECM is harvested by centrifugation at high speed. Adherent ECM is harvested by scrapping the bottom using a scrapper. Various ECMs are produced depending on induction and growth conditions, as shown in FIG. 16.

Figure 17:
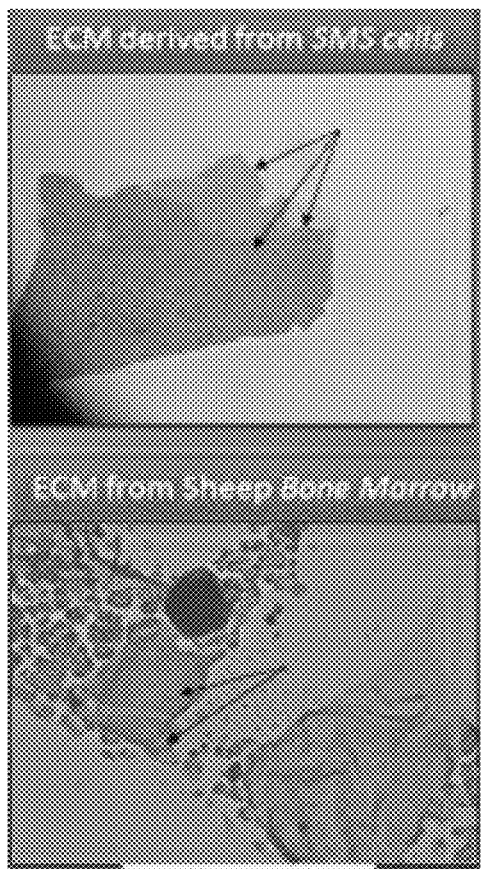
FIG. 17 outlines the formation of membranous extracellular matrix. Highly organized layers of extracellular matrices are produced by cultured SMS cells, comparable to extracellular matrix obtained from sheep bone marrow. The formation of membranous extracellular matrix was induced. At the bottom of the culture flask a dense mainly cell free ECM layer appears. Detaching by scraping indicated lower density than water. Further examination indicated the presence of three distinguishable sub-layers: the first was a smooth cell free layer in contact with the plastic of the flask; the second was also a smooth layer; and the third had a rough surface containing cells. The first and the second layer were clearly distinctive due to differential staining using the metachromatic dye safranin.
Figure 18A:
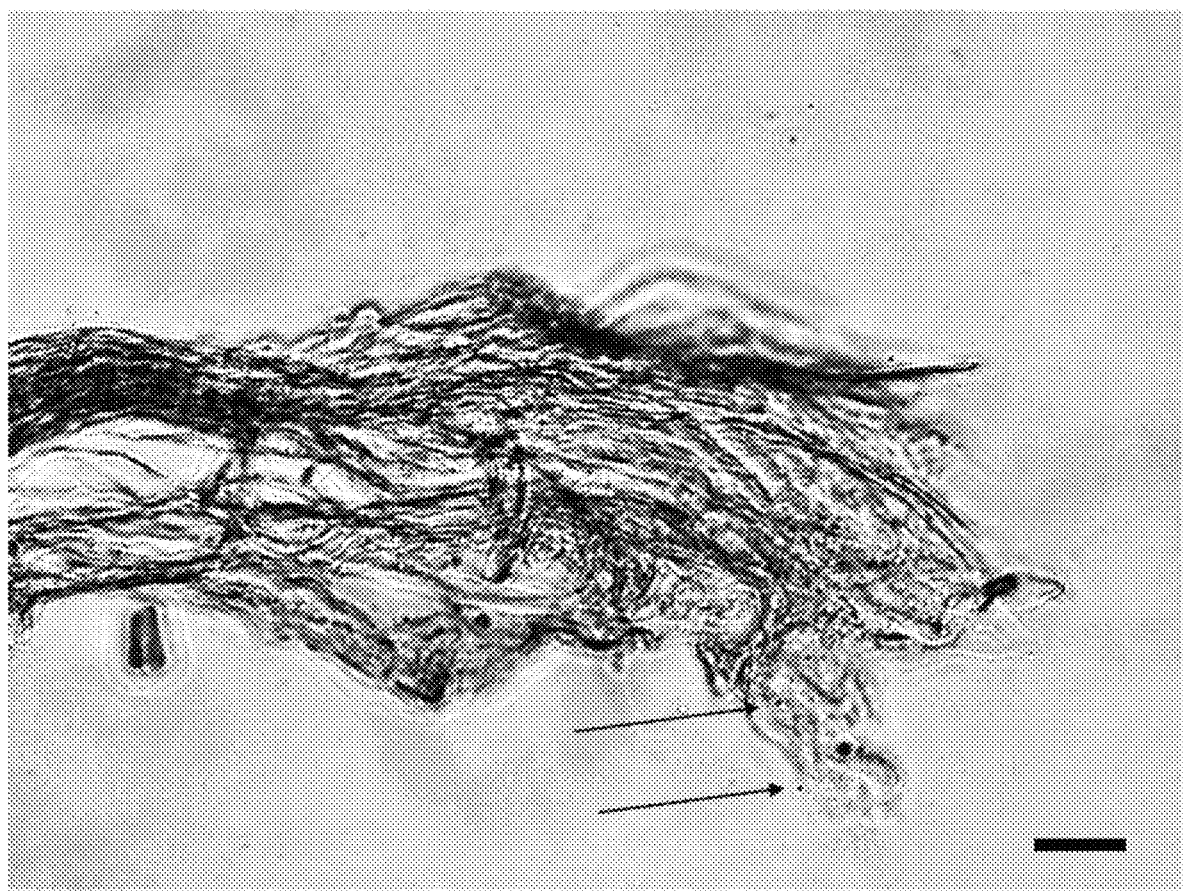
FIG. 18A depicts an initial culture of SMS cells (1-2 weeks) with a scaffold of mainly collagen fiber. SMS cells (arrows) attach preferentially to the fibers, rather than to the bottom of the polystyrene 6 well plate (200×; bar=30 μm).
Figure 18B:
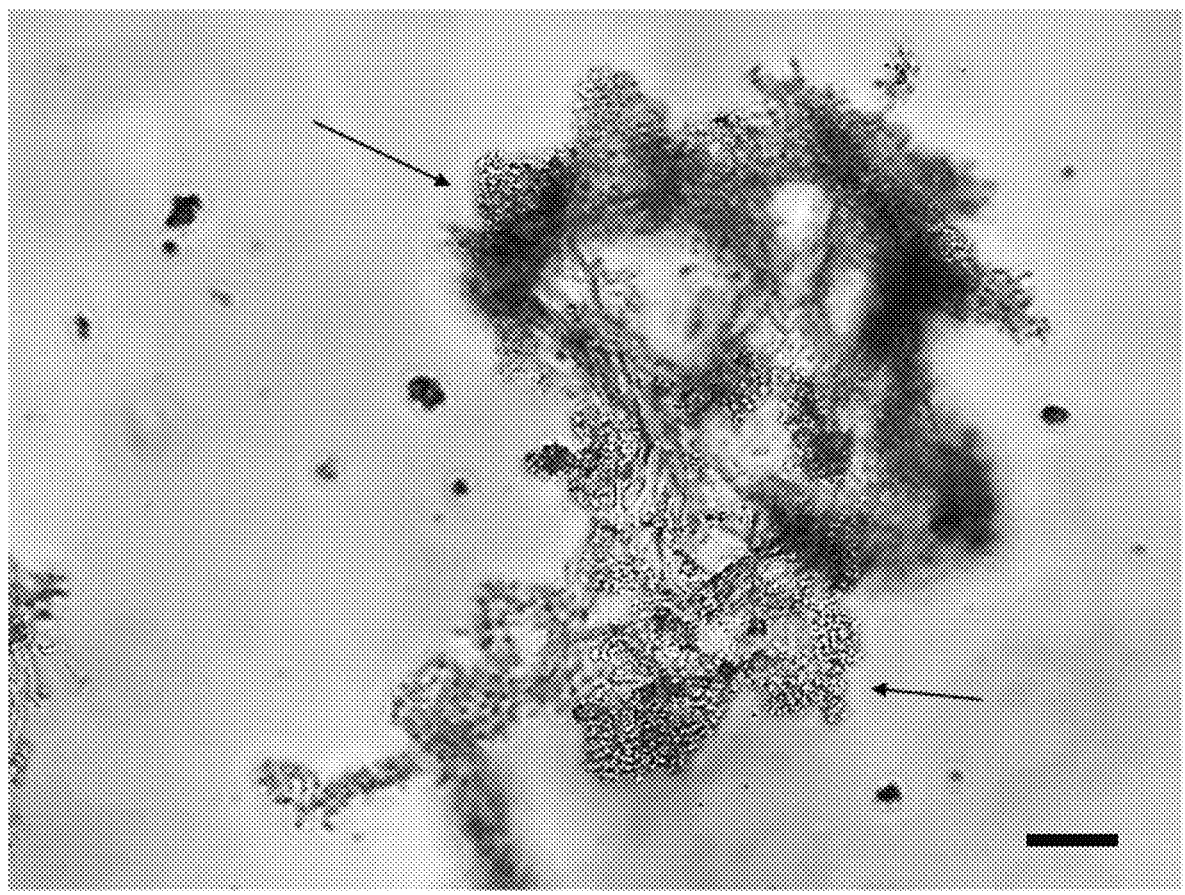
FIG. 18B depicts a late culture of SMS cells (4 weeks) in a 6 well plate with a scaffold of mainly collagen fiber. SMS cells attach preferentially to the fibers, and proliferate and differentiate to form extracellular matrix (arrows) (200×; bar=30 μm).
Figure 19A:
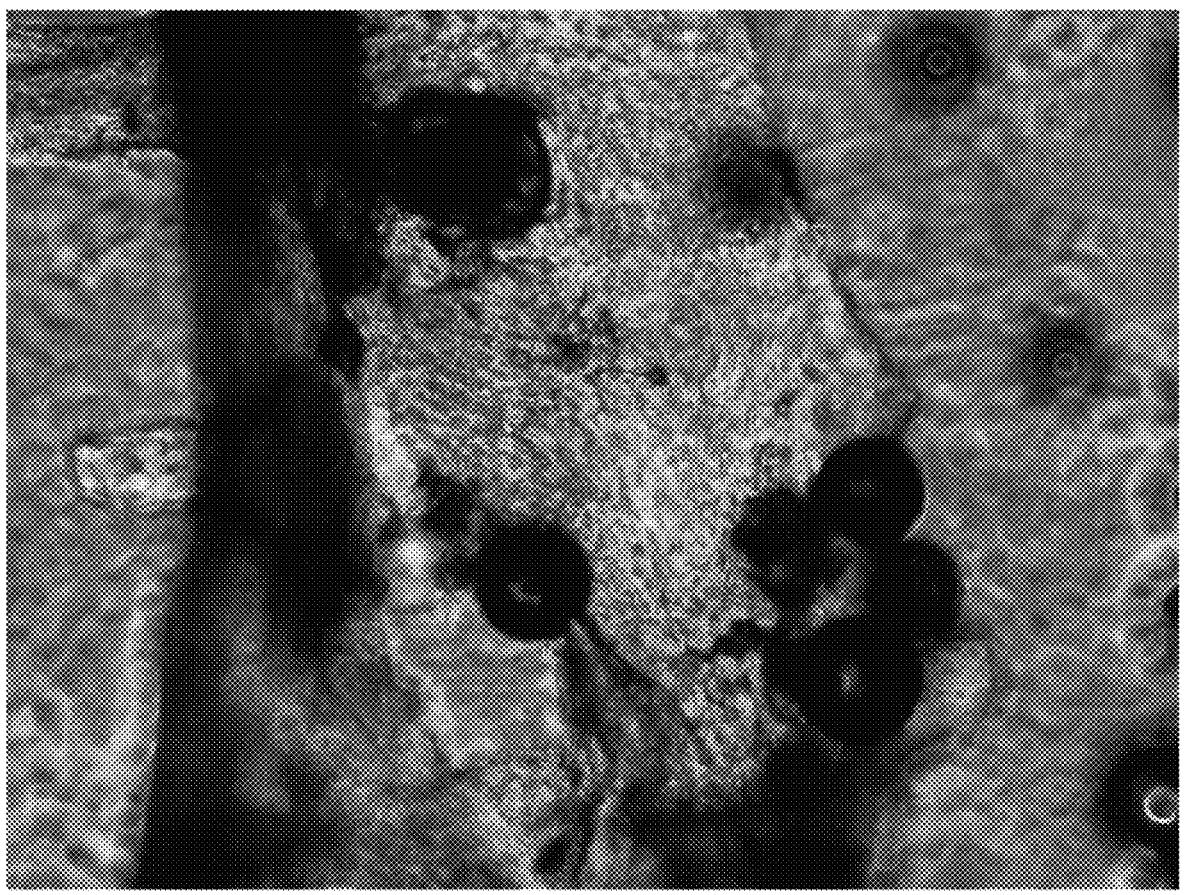
FIG. 19A depicts decellularized bone scaffold prior to co-culture with SMS cells.
Figure 19B:
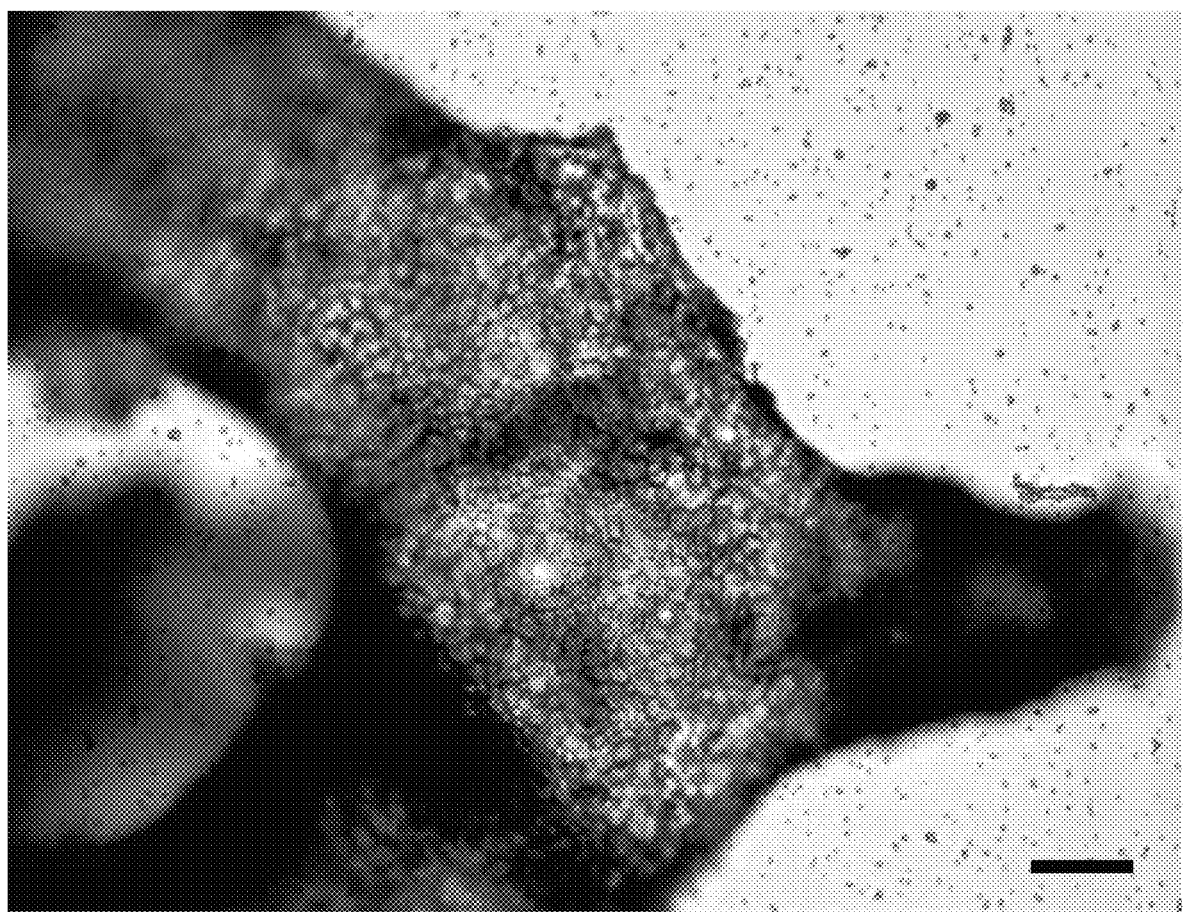
FIG. 19B depicts decellularized bone scaffold following incubation with SMS cells for 3 weeks. The differentiated SMS cells attach at the bone surface (100×; bar=60 μm).
Figure 19C:
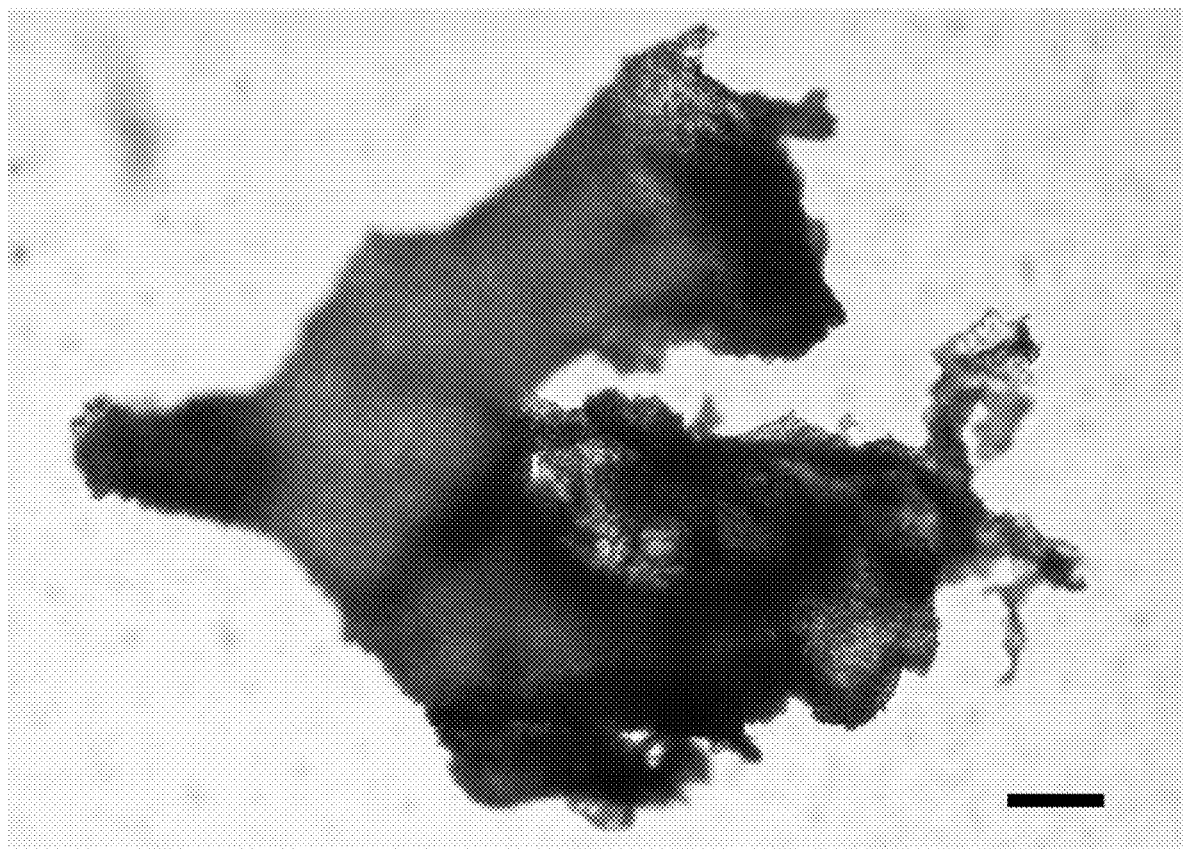
FIG. 19C depicts decellularized bone scaffold following incubation with SMS cells for 6 weeks. After six weeks, the growth of soft tissue is observed at the bone surface, which is derived from the SMS cells (40×; bar=150 μm).

ECM is decellularized using various methods known in the art. For example, chemical, physical, and enzymatic methods can be employed to decellularize the ECM, ensuring that the ECM scaffold maintains its structural and chemical integrity. In addition, various molecular components of the SMS derived ECM are enriched or isolated. ECM in various tissues of various organs can be shown to be similar or identical to ECM from in vitro SMS cell culture, as shown in FIG. 17.

SMS cell produced ECM may be freeze dried into powder and stored as such. ECM in powder or other form is capable of being used for various applications such as promoting cell growth or cell differentiation in vitro (such as for 3D cell culture) or in vivo (such as in promoting wound healing) (or inhibiting tumor growth).

Example 4

Production of Extracellular Matrix after Attaching SMS Cells to a Scaffold

This example provides the general procedure for the production of scaffolds including ECM SMS cells and cells derived therefrom.

SMS cells cultured in the presence of various scaffolds (such as native decellularized bone, soft decellularized collagen) attach favorably to scaffolds. SMS cells incubated in various growth media (37° C. and 5% $CO_2$) grow and differentiate after attaching to scaffolds. As shown in FIGS. 18A and 18B and FIGS. 19A, 19B, and 19C, microscopic observation indicates that SMS cells change shape drastically by differentiation, and that SMS cell differentiation varies depending on the nature of the scaffold.

SMS cell attachment, growth, and differentiation is influenced by varying the medium. SMS cells and cells derived from it produce extracellular matrix and tissue like structures attached to the scaffolds.

Figure 20:
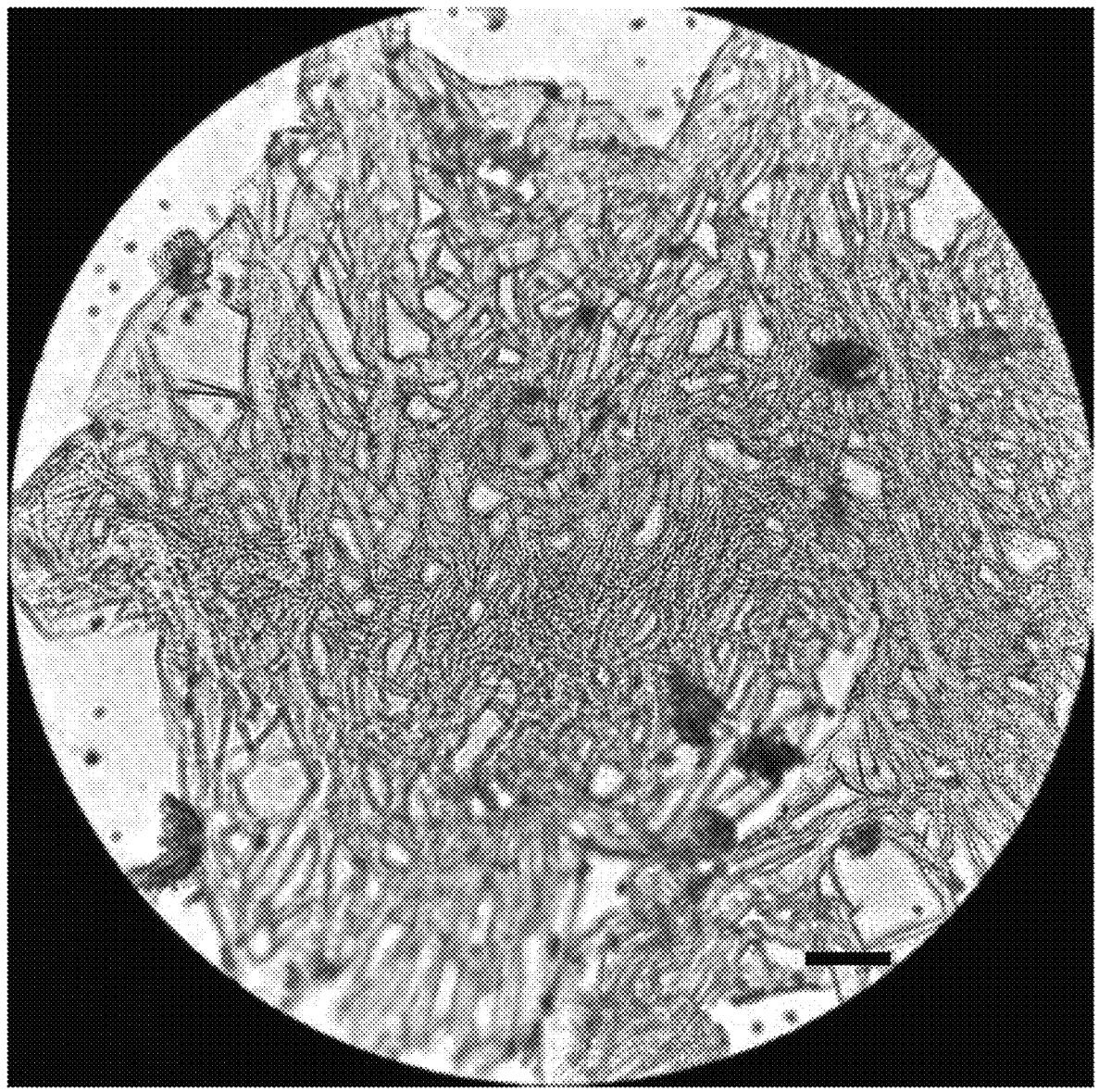
FIG. 20 depicts SMS cell derived tissue like structure, with tubule and porous morphology (200×; bar=30 μm).

Produced ECM and tissue-like structures are favorable to nutrient access because they are highly porous as a result of the formation of various tubular structures, as shown in FIG. 20. Cells and derivatives attached remain vital for months in culture medium (37° C. and 5% $CO_2$).

SMS cells, cells derived from it, SMS-produced ECM, and structures thereof, attached to various scaffolds, can be used to enhance the biocompatibility and shorten the healing process of implanted scaffolds.

Example 5

De Novo Production of Structured Scaffolds Using SMS Cells

This example details the de novo production of structured scaffolds using SMS cells.

SMS cells have a proclivity of organizing and positioning in an ordered fashion during in vitro cell culture. After suitable molecular induction, SMS cells produce scaffolds that are well structured and represent 3D bodies with pertinent geometric shapes.

Figure 21A:
FIG. 21A shows the de novo formation of scaffolds resembling bone fragments, derived from SMS cell culture using an inductive medium (200×; bar=30 μm).
Figure 21B:
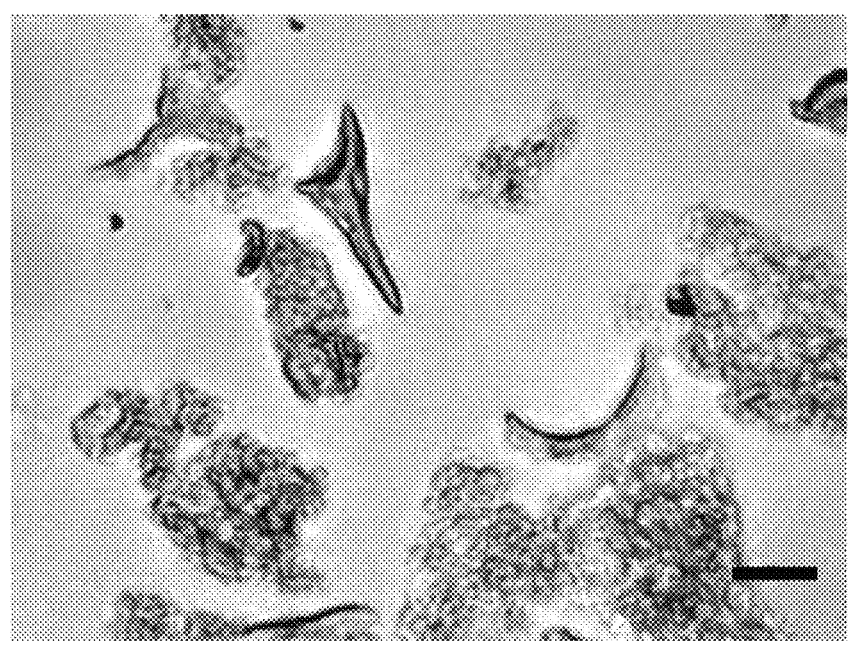
FIG. 21B shows the de novo formation of scaffolds resembling bone fragments, derived from SMS cell culture using an inductive medium (400×; bar=15 μm).

SMS cells grown in suspension are incubated using an inductive medium (37° C. and 5% $CO_2$) in a polystyrene plate. After biweekly medium addition for about three weeks different scaffolds appear with various shapes, as shown in FIGS. 21A and 21B.

Example 6

Production of Soft Tissue from Peripheral Blood

This example provides the general procedure for the production of soft tissue culture from peripheral blood.

Peripheral blood (containing the anti-coagulate ACD) is centrifuged at low speed and the supernatant is removed. SMS cells are added to the pellet and the mix is cultured using growth medium in a polystyrene flask for four days (37° C. and 5% $CO_2$).

At the bottom of the culture flask, a gel containing SMS cells forms, and includes white and red blood cells.

The gel is removed from the flask, washed twice using Hanks' buffer and is frozen at −20° C. After several days the frozen gel is removed and thawed. Thawed gel is washed several times using phosphate buffer solution (PBS) to remove most white blood and red blood cells, which are destroyed by the freeze/thaw cycle, whereas SMS cells are unaffected.

The washed gel is cut into smaller pieces and incubated in a flask or plate using a growth medium under standard conditions (37° C. and 5% $CO_2$), and become gradually more sturdy and more tissue-like.

The tissue-like structure demonstrates an organized structure and develops tubule and capillary like structures. The tissue-like structure does not contain white or red blood cells.

Figure 22:
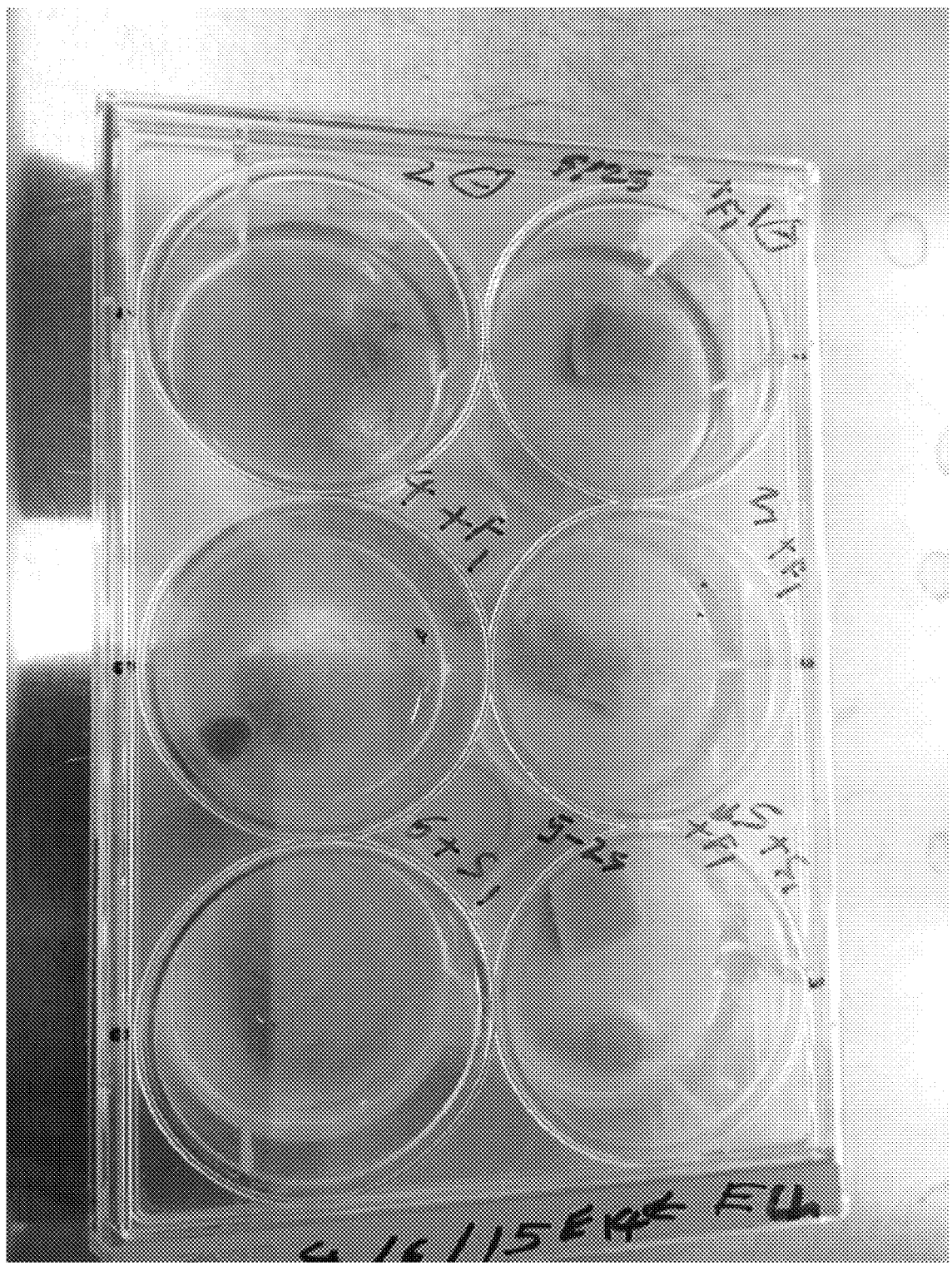
FIG. 22 shows soft tissue made using only peripheral blood components, including SMS cells. The tissue changes from a gel like transparent tissue to a darker and sturdier tissue.
Figure 23:
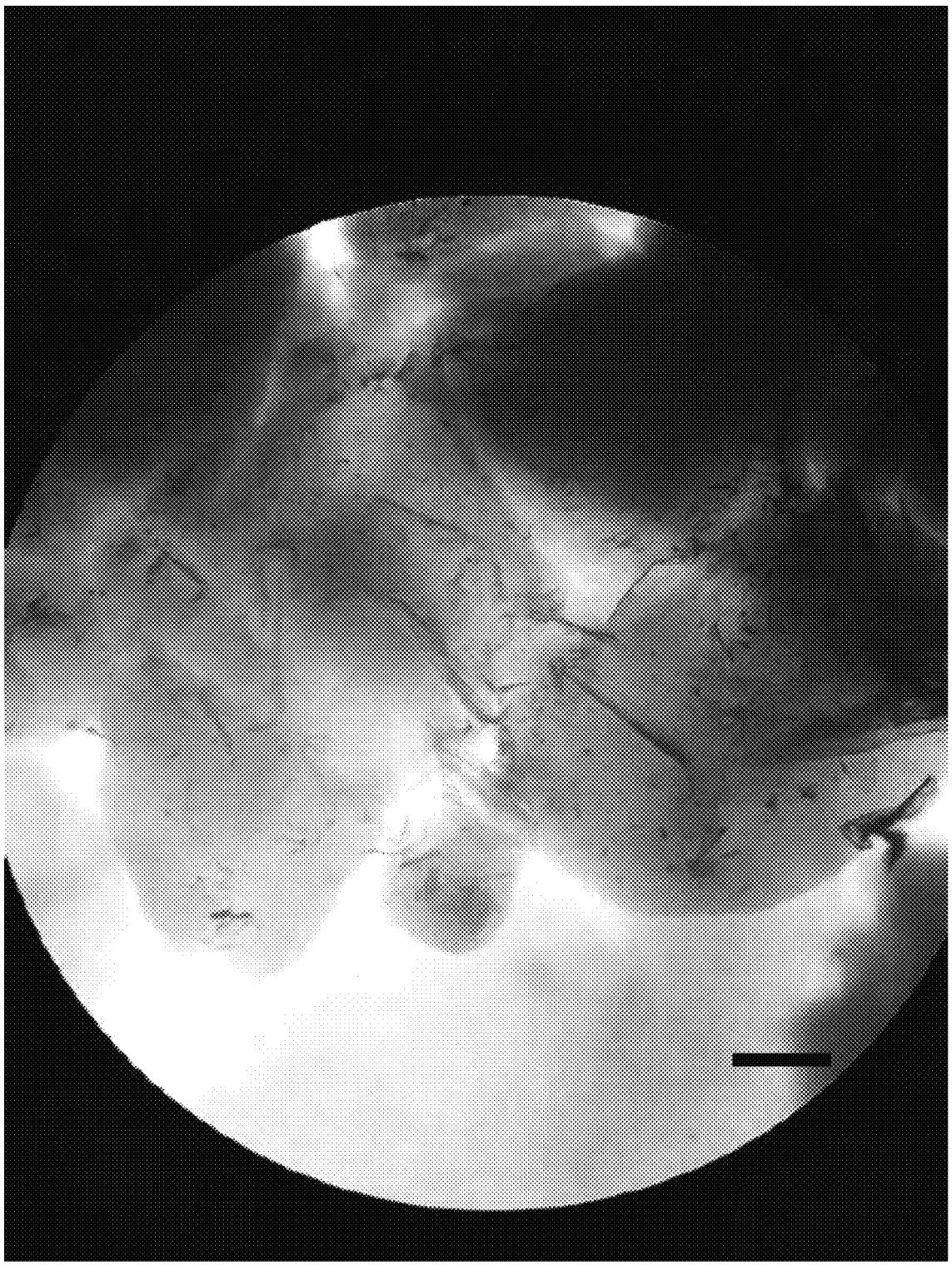
FIG. 23 shows soft tissue made using only peripheral blood components, including SMS cells, and shows tubular structures (40×; bar=150 μm).
Figure 24:
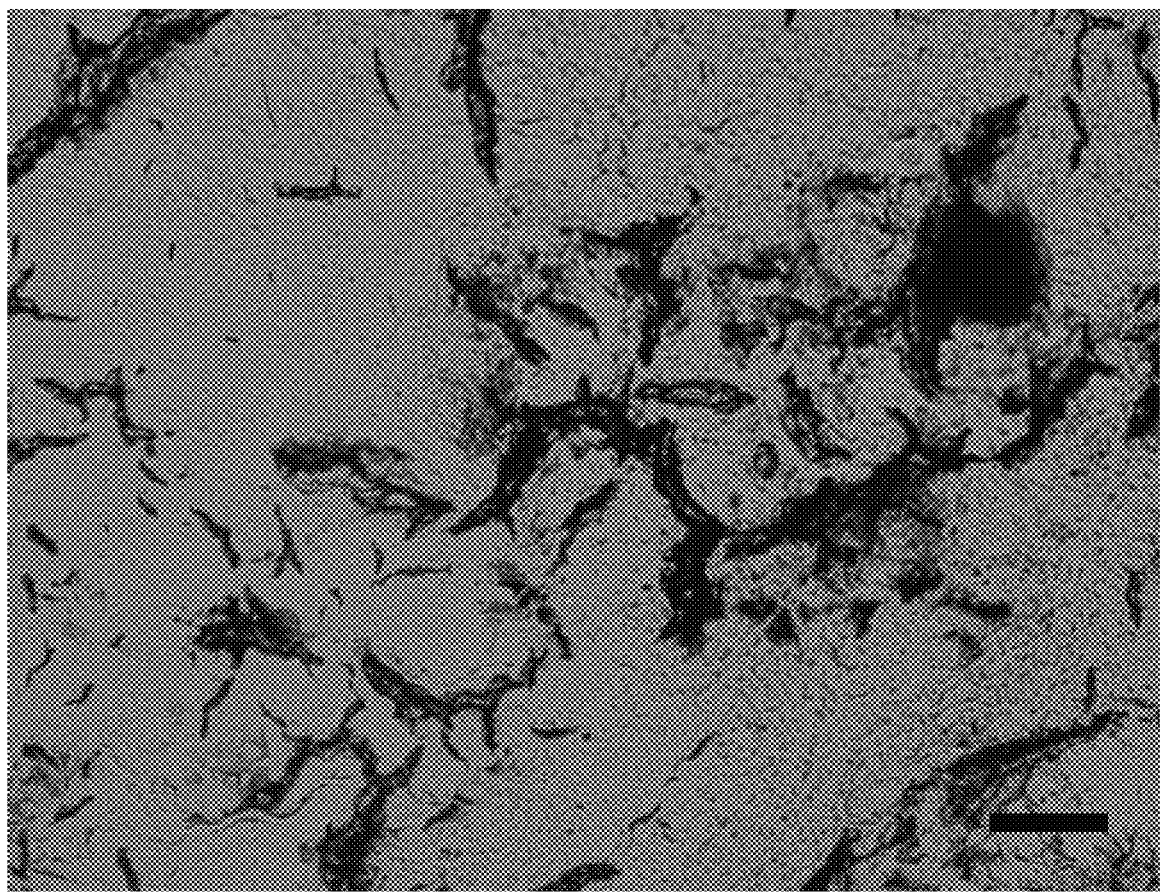
FIG. 24 depicts microscopic examination using trichrome staining of the soft tissue. The micrographs indicate the presence of capillary and vessel like structures, and show obvious multidimensional growth, extensions, and the merger of the tubule (40×; bar=150 μm).

As shown in FIGS. 22, 23, and 24, microscopic examination and staining show the presence of SMS cells and SMS derived cells.

Example 7

SMS Cells Introduced on a Surface

This example demonstrates the use of SMS cells on a substrate or surface.

SMS cells are introduced to a flask, container, chamber, channel, tube, vessel, niche, or bioreactor, wherein the surface of the flask, container, chamber, channel, tube, vessel, niche, or bioreactor is pretreated with etched surfaces of geometric shapes. The surface may be pretreated with a chemical or physical treatment, including, for example, the use of borosilicate, mechanical abrasion, blasting, silicon carbide, solvent, acid, anodizing, or other pretreatment assays. The pretreatment is used to provide a geometric shape on the surface of the flask, container, chamber, channel, tube, vessel, niche, or bioreactor. The geometric shape can include, for example, one or more line, curve, web, groove, ridge, or other shape.

SMS cells deposited or introduced to the pretreated flask, container, chamber, channel, tube, vessel, niche, or bioreactor organize about the geometric shape, using the shape as a guide for the organization of cell culture growth.

Example 8

SMS Cells on a Microfluidic Device

This example demonstrates the use of SMS cells on a microfluidic device.

SMS cells (and cells derived thereof) are introduced on a lab-on-a-chip device (that is a device that integrates one or several laboratory functions on a single chip that deals with handling particles in hollow microfluidic channels).

Including the use in cell or tissue or organ on a chip (a multi-channel 3D microfluidic cell culture chip that simulates the activities, mechanics and physiological response of entire organs and organ systems).

Resilient SMS cells may make the microfluidic chip applications more accessible (shelf life and expense, potential for differentiation, production of specific molecules). After being preserved in their undifferentiated form (the resilient form) cells integrated in the microfluidic circuits may be induced to exert a specific function or to differentiate, this may occur selectively, position based, via engineered channels that will provide to cells, occupying specific locations within the chip, so called "chambers", selective chemical inducers or other topical inducers (such as temperature or pressure) converting cells at selective positions to desired function and used at that stage).

Example 9

Increasing the Concentration and Yield of SMS Cells in Suspension

This example demonstrates the process for increasing small mobile stem cell concentration in suspension.

SMS cells were grown in suspension at 5% $CO_2$ 37° C. and maximal humidity for several weeks using the induction growth medium DMEM (Gibco, catalog N: 31053-0028) and 10% fetal bovine serum (Sigma, catalog N: F2442), 0.1 µmol/L dexamethasone (Sigma, catalog N: D4902), 0.05 mmol/L ascorbic acid-2-phosphate (Sigma, catalog N: 49752)) and 10 mmol/L β-glycerophosphate (Sigma, catalog N: G9422). Medium was replaced once weekly.

Cell concentration was significantly increased when grown in this medium as compared to the control population of cells grown in a medium of DMEM and fetal bovine serum.

Example 10

Cellular Interaction with SMS-Derived ECM

This example demonstrates the interaction of endothelial cells, keratinocytes, and fibroblasts with extracellular matrix-derived SMS cells.

Interaction of Endothelial Cells with SMS-Derived ECM

SMS cells grown in suspension were washed twice using the basal medium DMEM (Gibco, catalog N: 11054-020). The cells were incubated in a 6 well culture plate (TPP catalog N: 92406), at 5% $CO_2$ 37° C. and maximal humidity for 2 weeks, using the growth medium of DMEM (Gibco, catalog N: 11054-020) and 10% fetal bovine serum (Sigma, catalog N: F2442). Medium was replaced twice weekly following the first week. SMS cells produce a stable adherent layer of extracellular matrix (ECM). The wells were washed three times with basal medium 200 (Gibco, catalog N: M200-500) before endothelial cell application.

Human umbilical cord vascular endothelial cells purchased from life technology (Catalog Number: C-003-5C, Lot: 1786264) were added to each well (100K), and incubated at 5% $CO_2$ 37° C. and maximal humidity using 2 mL of the growth medium of basal medium 200 (Gibco, catalog N: M200-500), 2% supplement large vessel endothelial supplement (LVES; Gibco, catalog N: 14608-01), for each well. Medium was replaced twice weekly.

The endothelial cells were observed migrating into the extracellular matrix made by SMS cells (FIGS. 25A and 25B), and actively proliferating within the matrix (FIGS. 26A-26C). After several days, some of the endothelial cells differentiated into tubes and survived in that state for the duration of the experiment (several weeks) (FIGS. 27A and 27B). These results are unexpected because the same endothelial cells are expected to form tubes in Geltrex® (Gibco, catalog N; A14132-02), the ECM matrix derived from animal origin, but will survive for only few hours and undergo apoptosis.

The endothelial cells formed transiently aligned cells along the edges of aligned SMS cells with endothelial cells largely absent at the core between borders, which is reminiscent of larger tubular (vessel) structures (FIGS. 28A-28C).

After about two weeks after the initiation of culture, the endothelial cells formed long stable vessels. These vessels were firmly anchored at both ends at the plate's adherent cell layer, but eventually expanded above in the 3D space, and were otherwise detached from the cell adherent layer (FIGS. 29A-29D).

Interaction of Keratinocytes with SMS-Derived ECM

SMS cells grown in suspension were washed twice using the basal medium DMEM (Gibco, catalog N: 11054-020). The cells were incubated in a 6 well culture plate (TPP catalog N: 92406), at 5% $CO_2$ 37° C. and maximal humidity for 2 weeks, using the growth medium of DMEM (Gibco, catalog N: 11054-020) and 10% fetal bovine serum (Sigma, catalog N: F2442). Medium was replaced once weekly. SMS cells produce a stable adherent layer of extracellular matrix.

Normal neonatal Human Epidermal Keratinocytes purchased from Lonza (catalog N: 00192906 lot: 0000357051) were added to each well (100K), incubated at 5% $CO_2$ 37° C. and maximal humidity, using 3 mL growth medium DMEM (Gibco, catalog N: 11054-020) and 15% fetal bovine serum (Sigma, catalog N: F2442) for each well. Medium was replaced twice weekly.

The keratinocyte cells formed an adherent layer on top of the extracellular matrix made by SMS cells (FIGS. 30A and 30B). This structure remained stable for several weeks.

Interaction of Fibroblast with SMS-Derived ECM

SMS cells grown in suspension were washed twice using the basal medium DMEM (Gibco, catalog N: 11054-020). The cells were incubated in a 6 well culture plate (TPP catalog N: 92406), at 5% $CO_2$ 37° C. and maximal humidity for 2 weeks, using the growth medium of DMEM (Gibco, catalog N: 11054-020) and 10% fetal bovine serum (Sigma, catalog N: F2442). Medium was replaced twice weekly following the first week. SMS cells produce a stable adherent layer of extracellular matrix (ECM).

Normal human skin fibroblasts from Lonza (catalog N: CC-2511, lot: 0000473428) were added to each well (100K), incubated at 5% $CO_2$ 37° C. and maximal humidity, using 2 mL growth medium DMEM (Gibco, catalog N: 11054-020) in addition 10% fetal bovine serum (Sigma, catalog N: F2442) for each well. Medium was replaced twice weekly.

The fibroblast cells were observed migrating into the extracellular matrix made by SMS cells (FIGS. 31A and 31B), migrating and proliferating within the matrix (FIGS. 32A and 32B) and reaching confluency in few days. Fibroblasts survived in that state for the duration of the experiment (several weeks).

Example 11

Differentiation of SMS Cells into Neural Cells

This example demonstrates the differentiation of small mobile stem cells into neural cells in cell culture.

SMS cells were grown in suspension and were washed twice using the basal medium DMEM (Gibco, catalog N: 31053-0028). The cells were incubated in a 6 wells culture plate (TPP catalog N: 92406) at 5% $CO_2$ 37° C. and maximal humidity for 2 weeks, using the growth medium DMEM (Gibco, catalog N: 31053-0028) and 10% Bovine Calf serum (Sigma, catalog N: 12133C). The medium was replaced twice weekly following the first week. SMS cells were then incubated with β-mercaptoethanol (Sigma, catalog N: M3148) for 24 hours, washed three times using Hanks buffered salt solution (Gibco, catalog N: 14025-092), and incubated at 5% $CO_2$ 37° C. and maximal humidity, using the neurogenic induction medium, composed of DMEM (Gibco, catalog N: 31053-0028), 2% DMSO (Sigma, catalog N: D2438) and 200 μM butylated hydroxyanisole (Sigma, catalog N: B1253). Medium was replaced twice weekly.

Figure 33A:
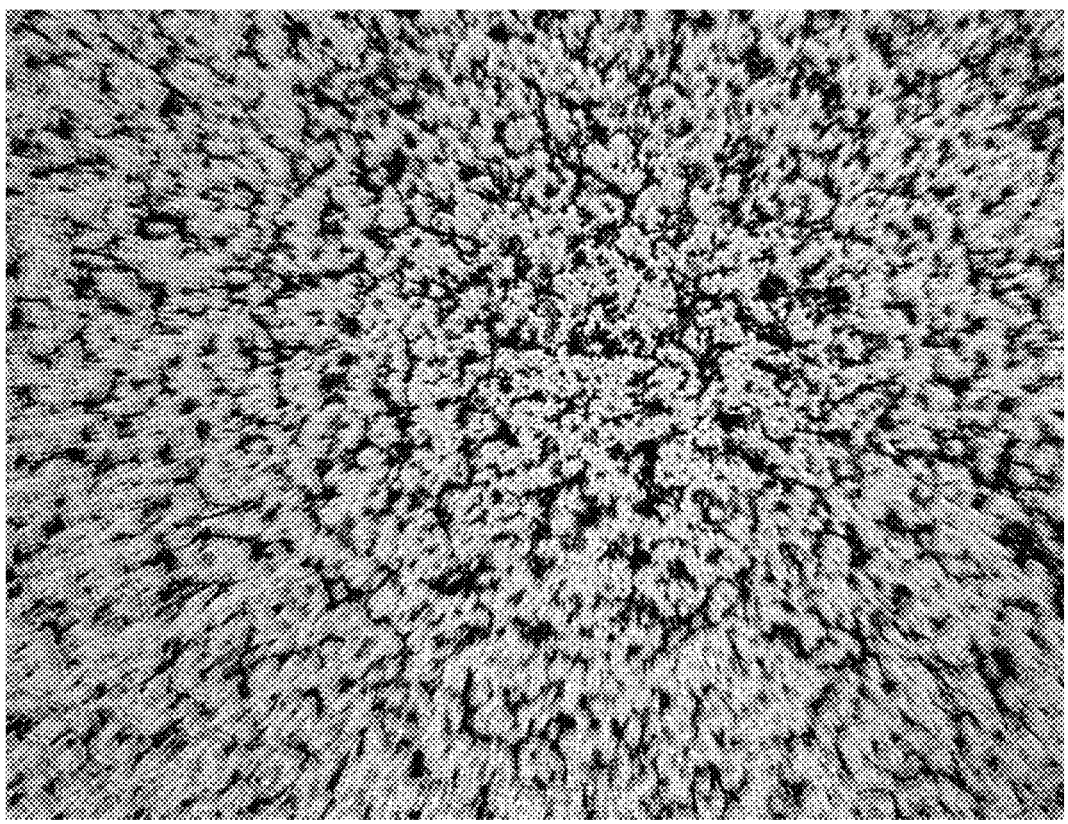
FIGS. 33A, 33B, and 33C depict SMS cells induced in neurogenic medium (FIG. 33A—200×.
Figure 33B:
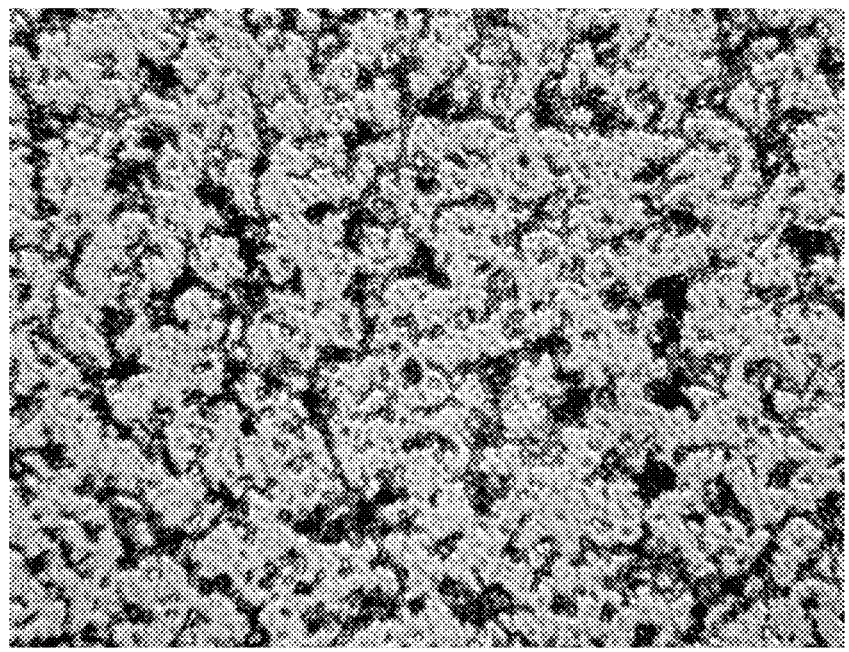
Figure 33C:
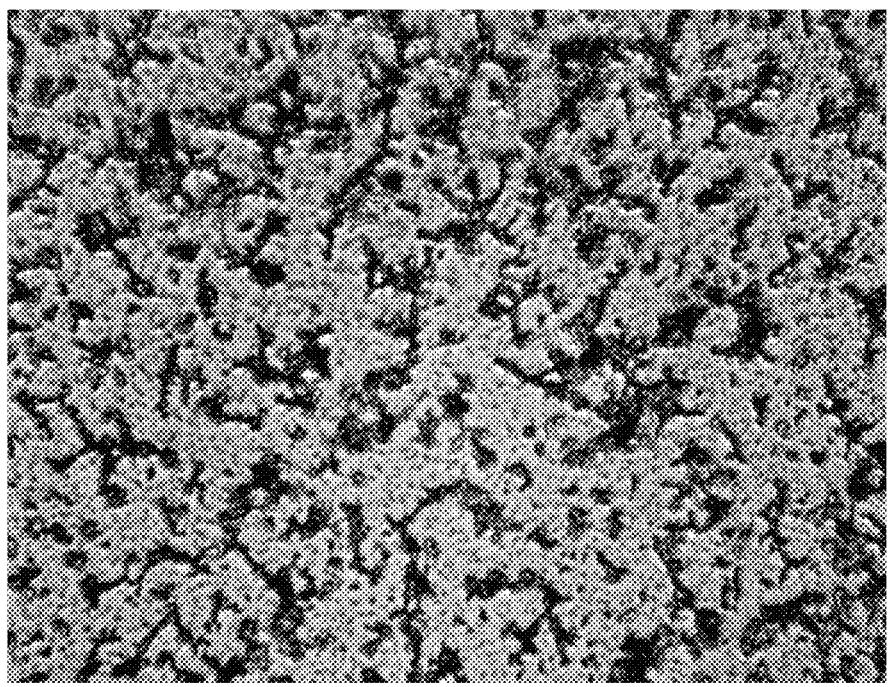

After two weeks, cells exhibited dramatic morphological changes consistent with neural cells (FIGS. 33A-33C). These cells remained stable for several months at differentiation medium in the absence of any serum or additives. Proteomic analysis demonstrated the presence of neural specific proteins such as doublecortin domain containing protein 2C (DCDC2) and keratin associated protein (KR-TAP) 5-1.

Example 12

Differential Expression of Proteins by Induction of SMS Cells Grown in Suspension This example provides methods for the differential expression of a variety of proteins from small mobile stem cells grown in suspension.

SMS cells were grown in suspension at 5% $CO_2$ 37° C. and maximal humidity for several weeks using the induction growth medium DMEM (Gibco, catalog N: 31053-0028) and 10% bovine calf serum (Sigma, catalog N: 12133C), 0.1 μmol/L dexamethasone (Sigma, catalog N: D4902), 0.05 mmol/L ascorbic acid-2-phosphate (Sigma, catalog N: 49752)) and 10 mmol/L β-glycerophosphate (Sigma, catalog N: G9422).

As a control cells were grown in a control medium of DMEM and 10% bovine calf serum. Cells grown in the induction growth medium demonstrated the differential production of proteins; examples: coagulation factor XIII A chain, Apolipoprotein E, Antithrombin III, BMP1, Vitronectin.

Example 13

Anti-Microbial Protein Production Using SMS Cells

This example provides methods for the production of anti-microbial proteins from small mobile stem cells grown in suspension.

SMS cells can be cultured for years under standard conditions without any antibiotics. The proteomic analysis of ECM derived from in vitro cultured SMS cells demonstrates the following proteins that are considered anti-microbial proteins (AMP): collectin, C-type lectin family 4, septin 12, and pancreatic ribonuclease.

Example 14

Enlargement of SMS Cells

This example provides methods for the enlargement of small mobile stem cells.

Figure 8A:
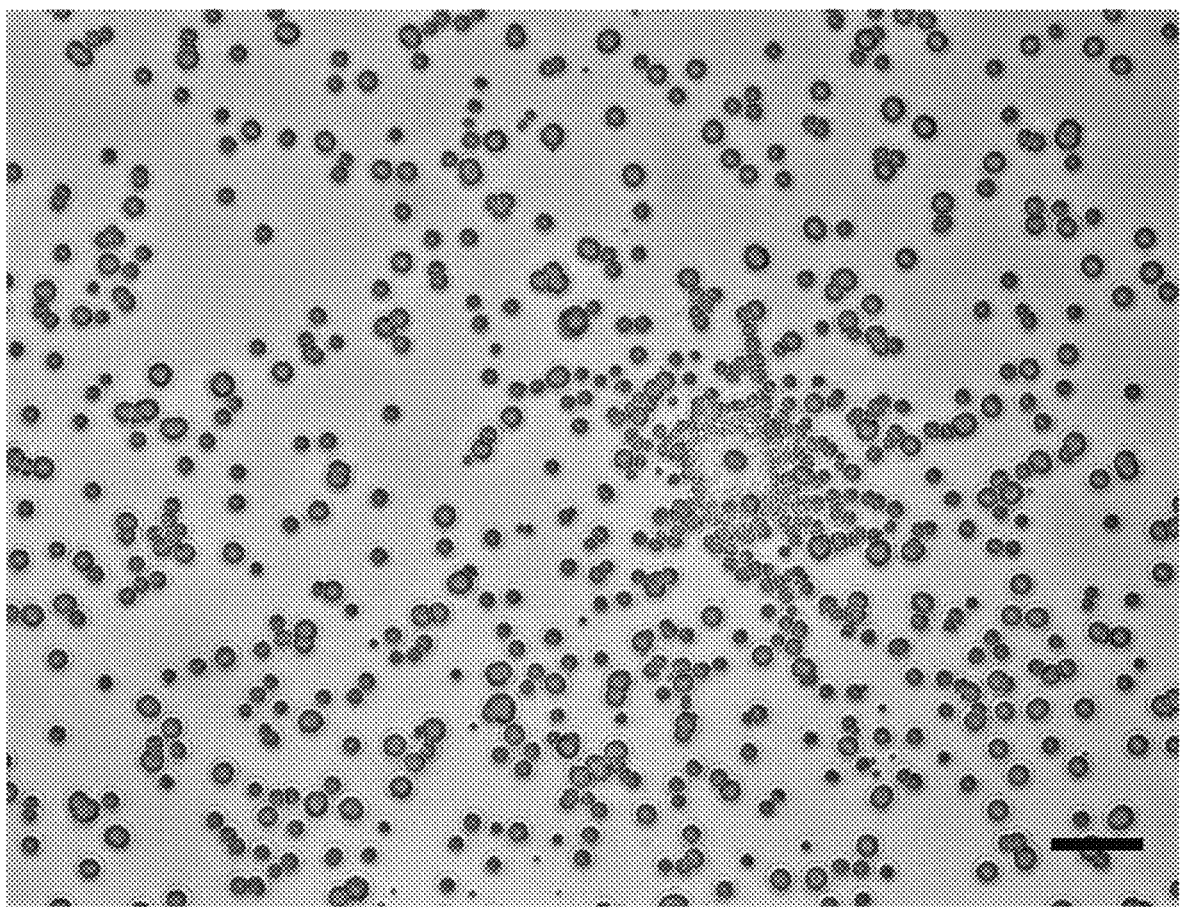
FIG. 8A depicts differentiated SMS cells cultured in a 6 well plate in an inductive medium. The SMS cells are enlarged and undergo morphological changes and aggregate sideways (200×; bar=30 μm).
Figure 8B:
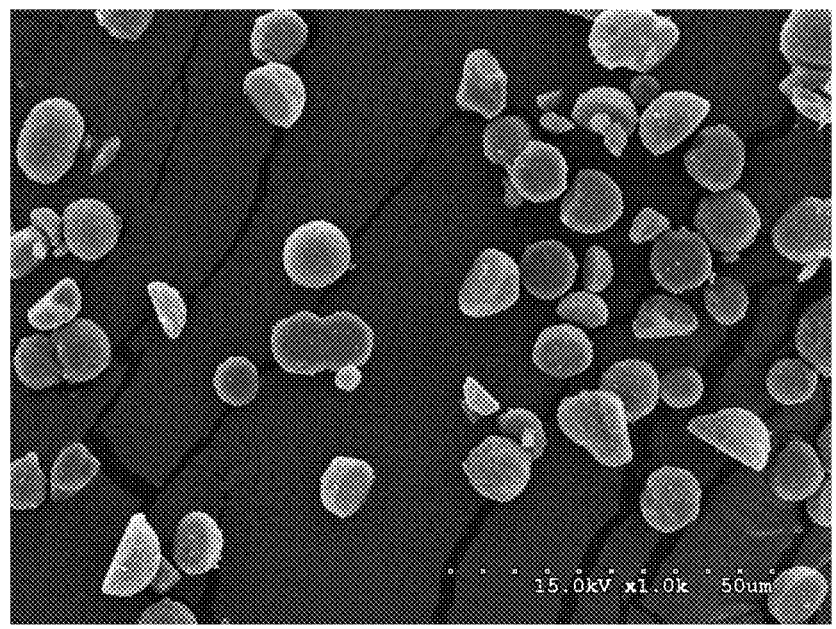
FIGS. 8B and 8C depicts a scanning electron micrographs of enlarged SMS derived cells following serum deprivation. SMS cells adhered and gradually underwent morphological changes resulting in enlarged cells.
Figure 8C:
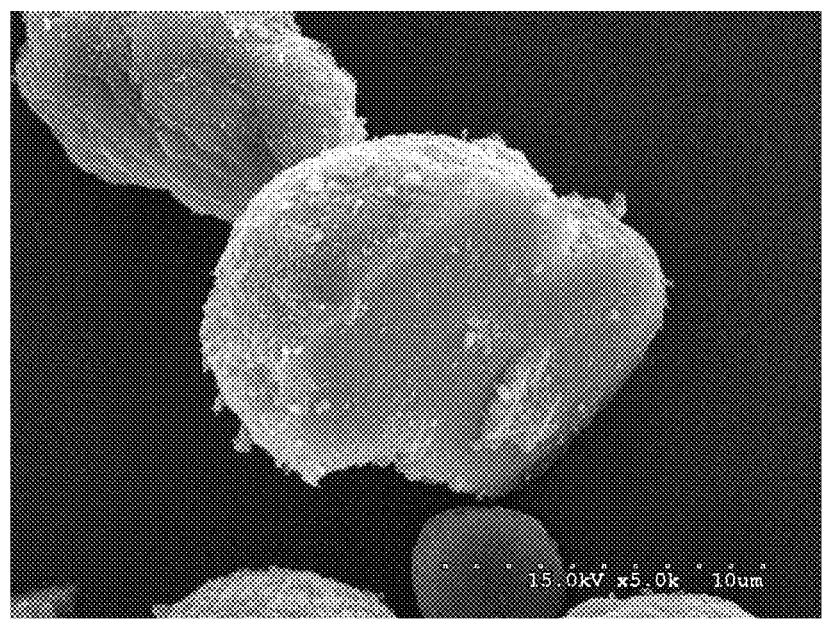
Figure 8D:
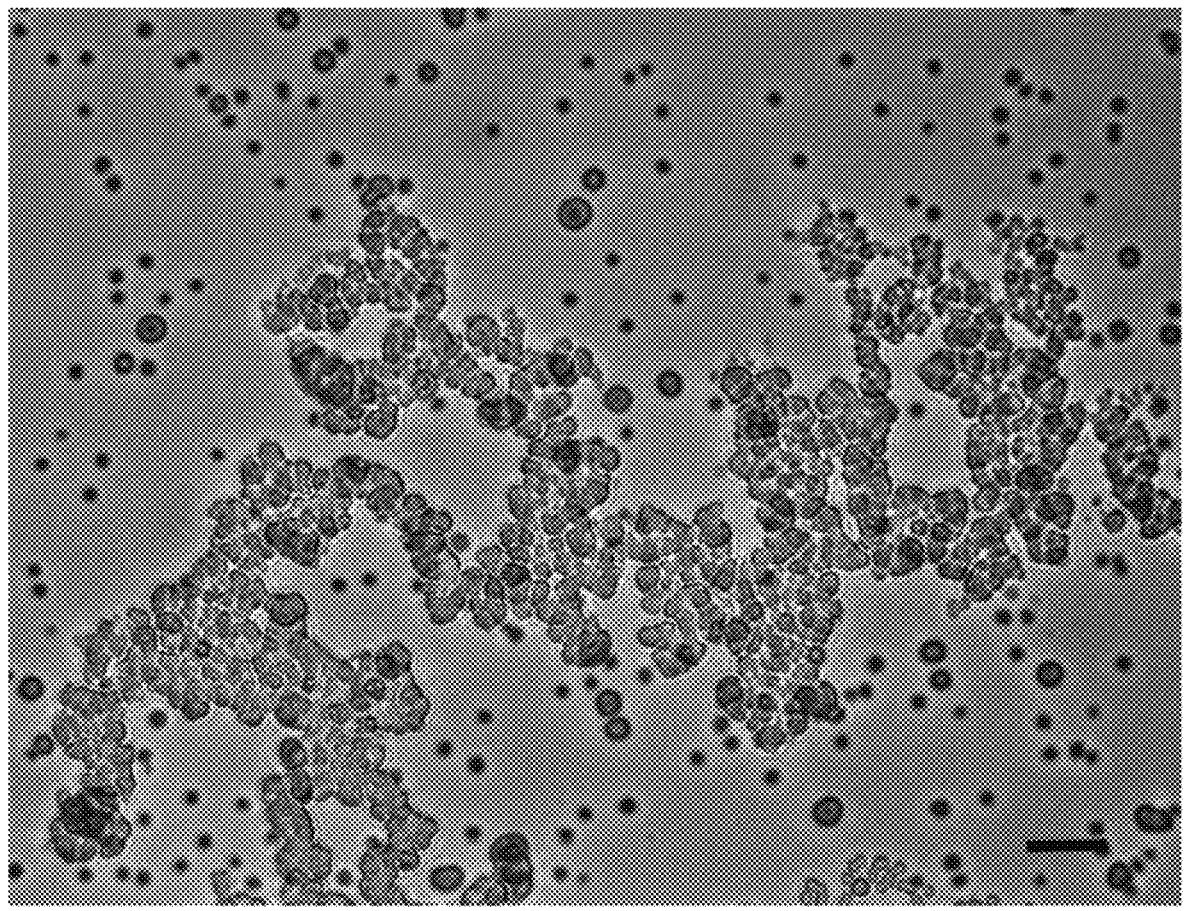
FIG. 8D depicts differentiated SMS cells cultured in a 6 well plate in an inductive medium. The cell aggregate floats, indicating that the cells have lost adherence to the flask. Cells have undergone morphological changes, have become cuboidal, and adhered sideways to each other, indicating a switch in polarity, creating an apical and basal surface, such as in epithelial cells (400×; bar=15 μm).
Figure 9A:
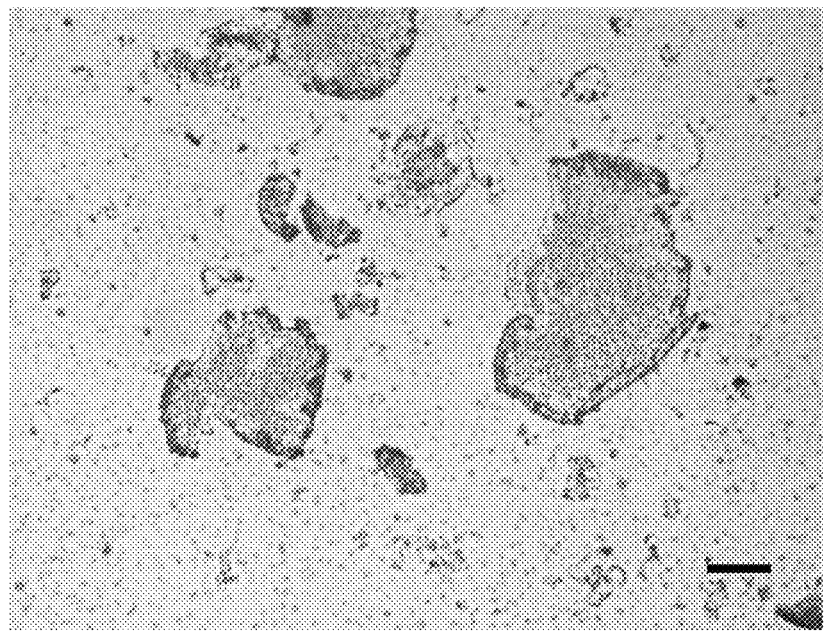
FIG. 9A depicts large suspended round cells, slightly protruding edges, with a transparent cytoplasm. The cells were derived from SMS cells cultured in a 6 well plate, and having undergone gross morphological changes (400×; bar=15 μm).
Figure 9B:
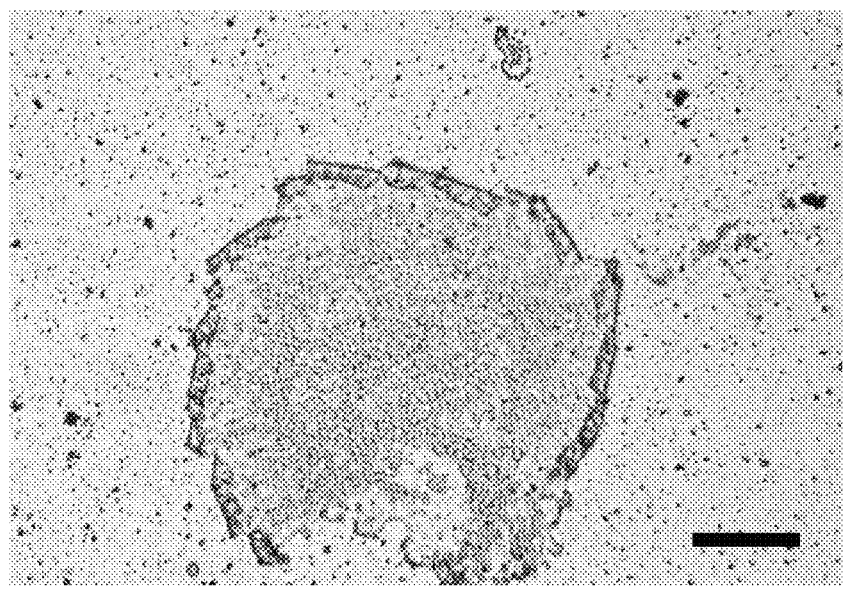
FIG. 9B depicts large suspended round cells, slightly protruding edges, with a transparent cytoplasm. The cells were derived from SMS cells cultured in a 6 well plate, and having undergone gross morphological changes (400×; bar=15 μm).
Figure 10:
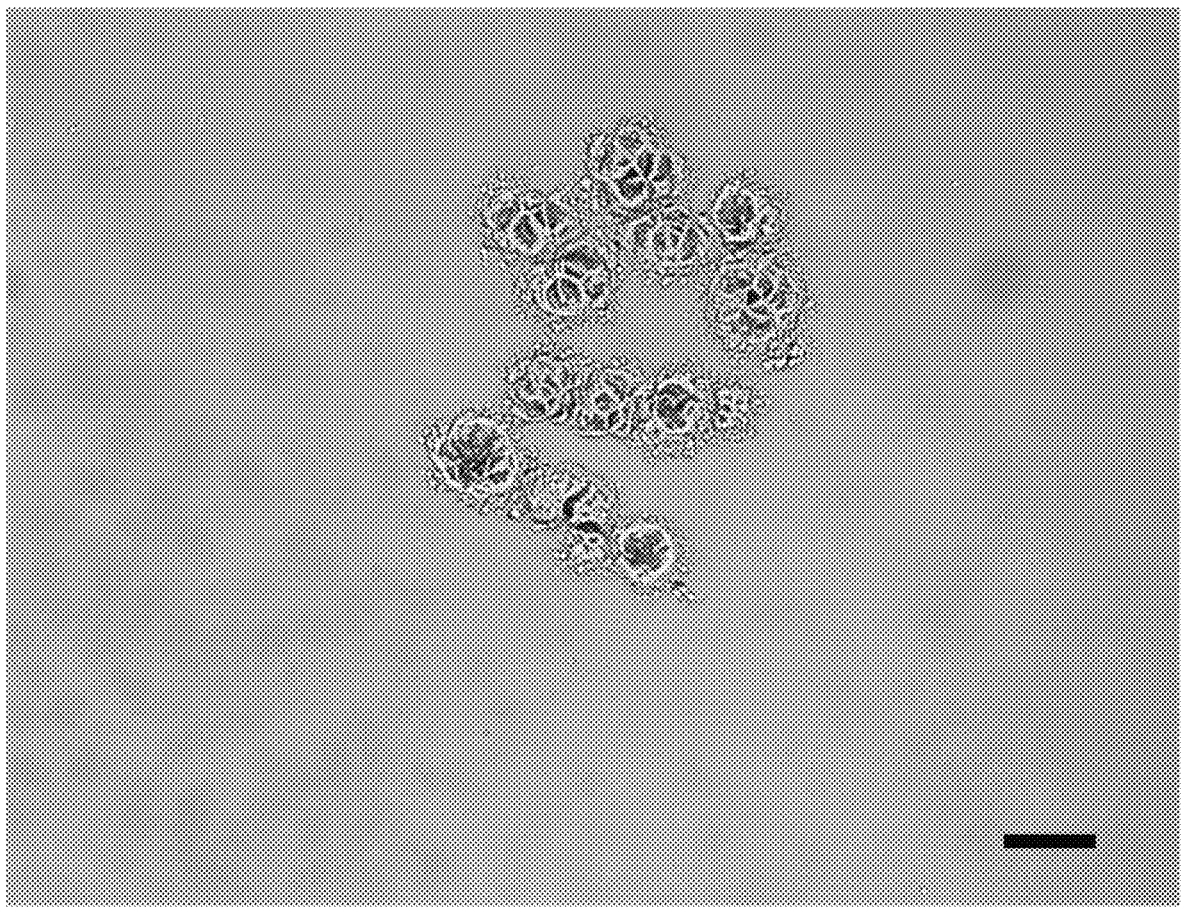
FIG. 10 depicts large flat floating round cells with low buoyancy and a transparent cytoplasm. The cells were derived from SMS cells cultured in a 6 well plate, and having undergone gross morphological changes (200×; bar=30 μm).
Figure 11:
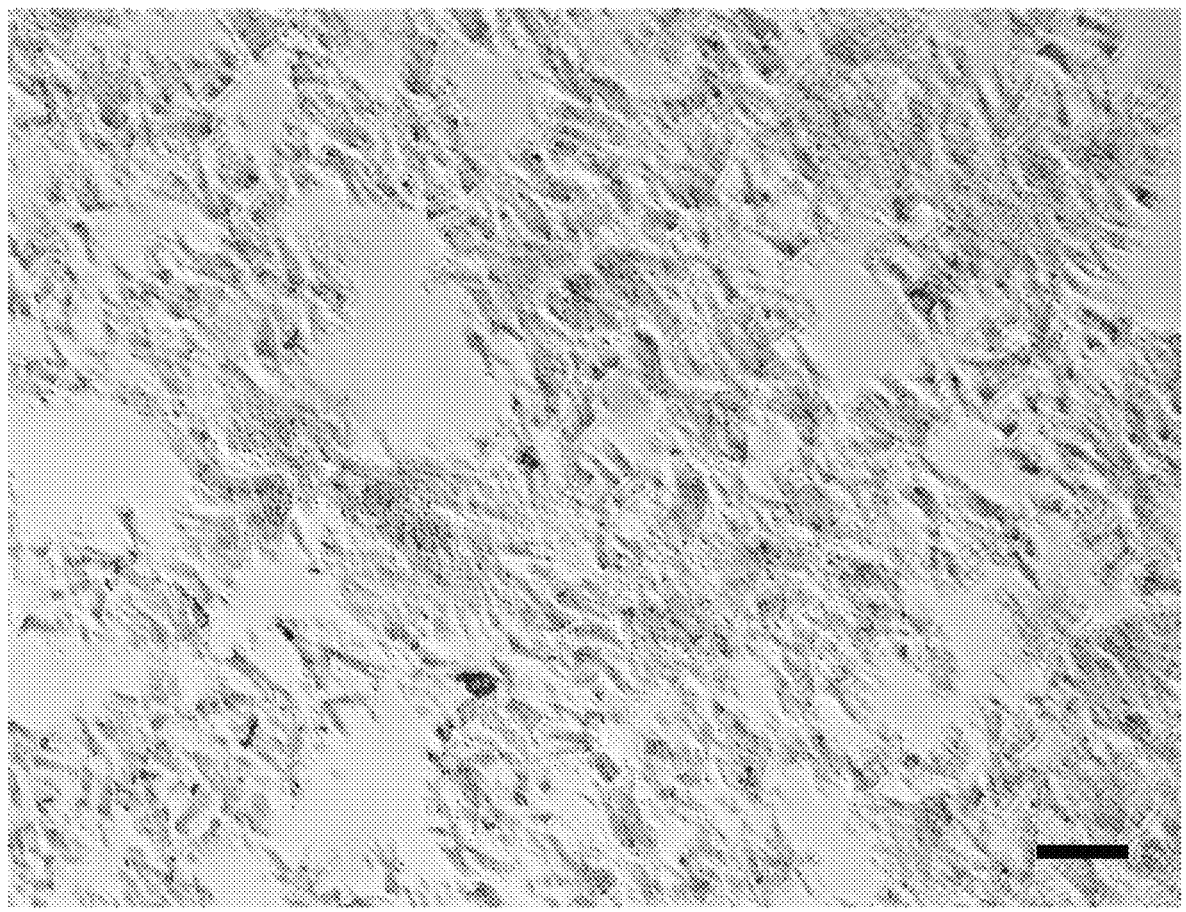
FIG. 11 depicts large floating flat irregular shaped cells with extension and transparent cytoplasm, derived from SMS cells cultured in a 6 well plate in an inductive medium (200×; bar=30 μm).
Figure 12:
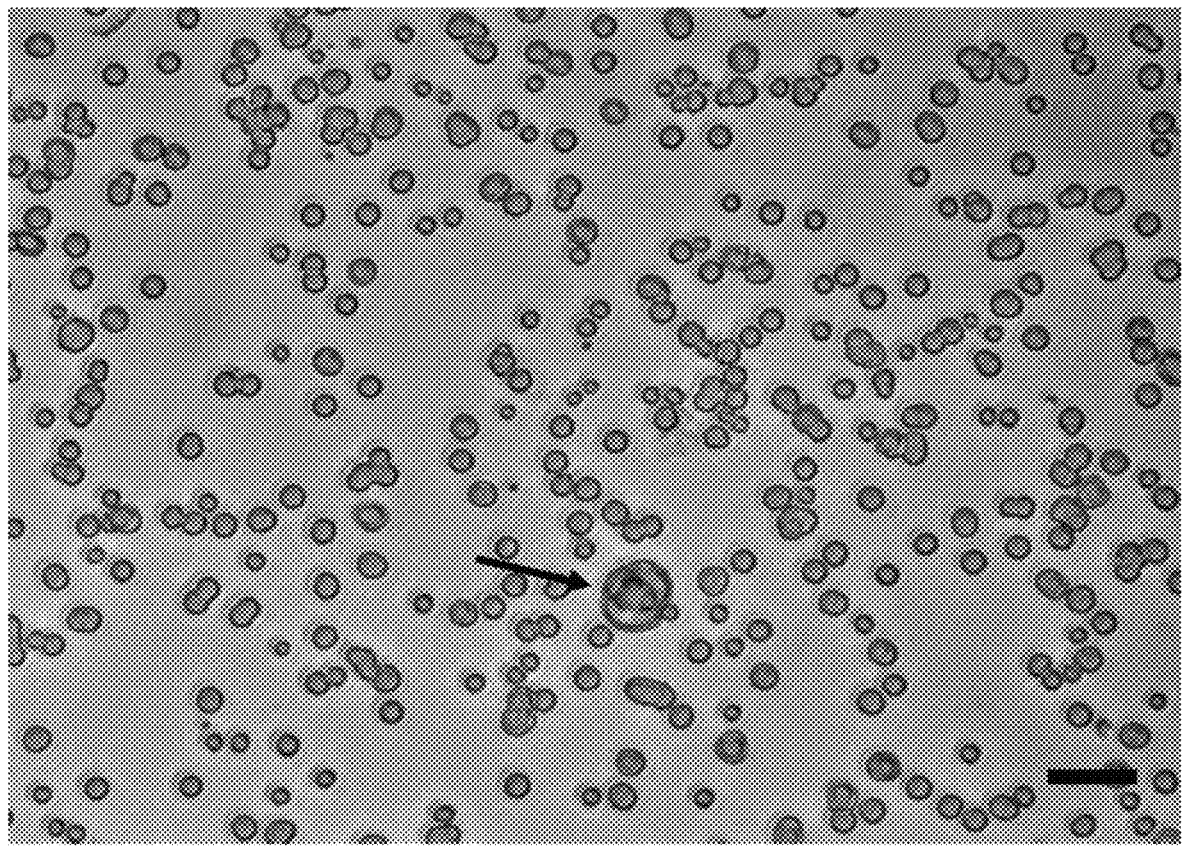
FIG. 12 depicts adherent cells with large round smooth edges, having a consistent shape and transparent cytoplasm (arrow), derived from SMS cells cultured in a 6 well plate in an inductive medium (400×; bar=15 μm).
Figure 13A:
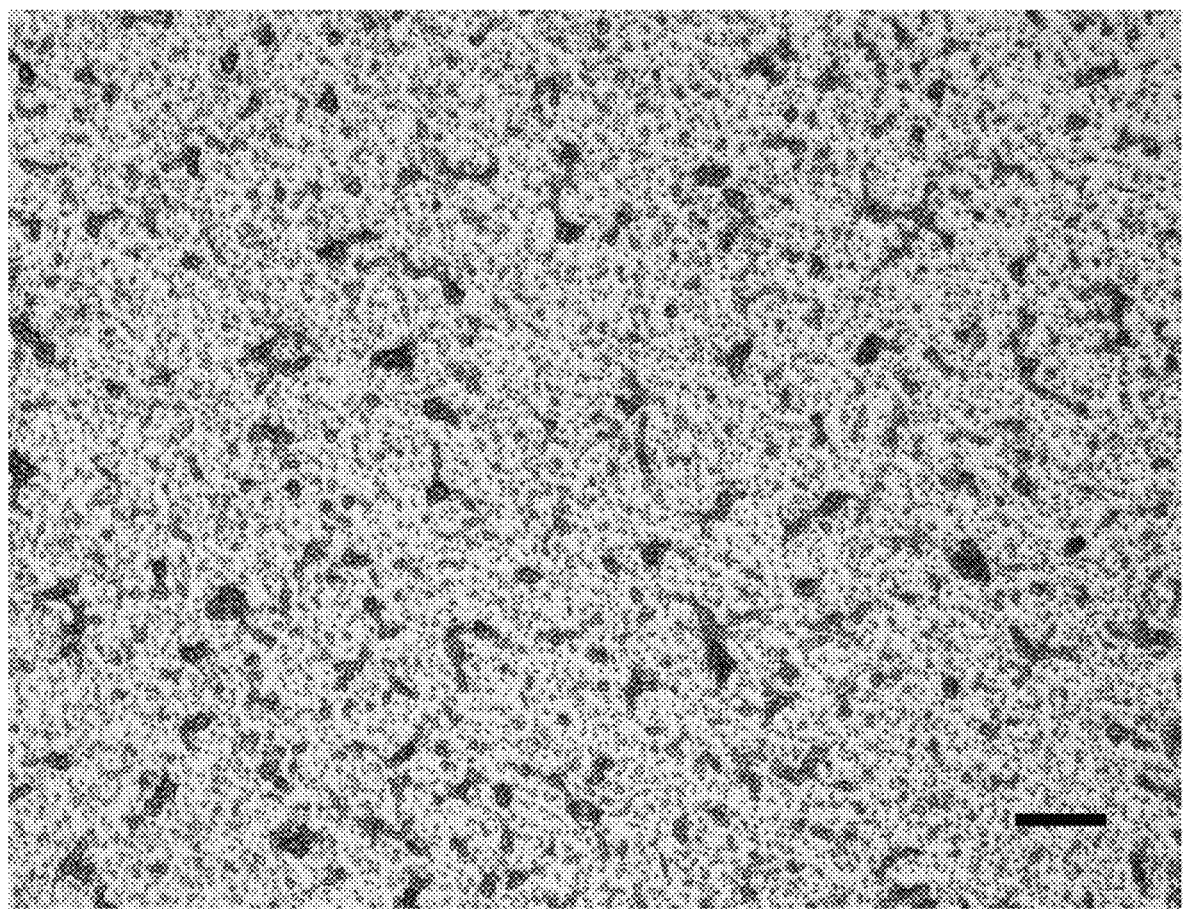
FIG. 13A depicts large adherent flat cells with irregular shape and extensions, derived from SMS cells cultured in a 6 well plate in an inductive medium (40×; bar=150 μm).
Figure 13B:
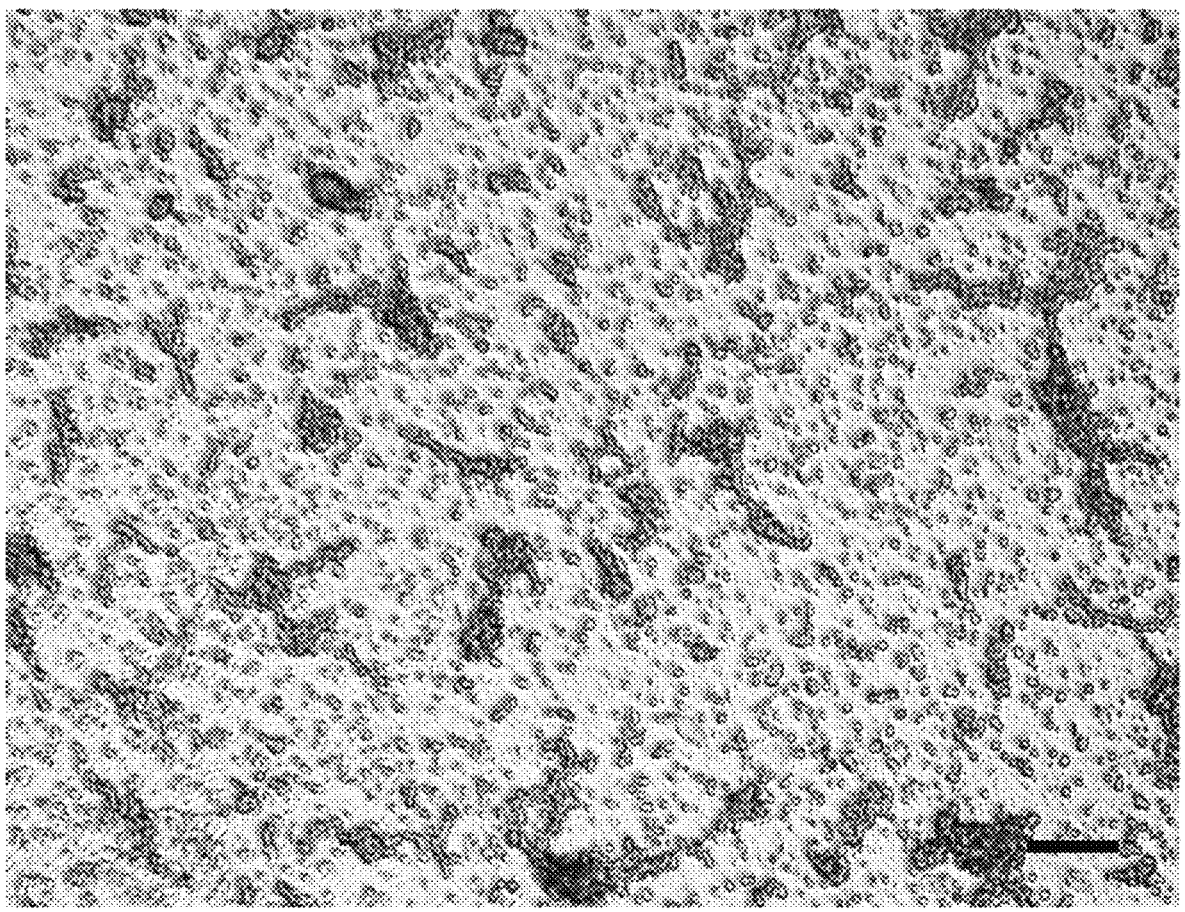
FIG. 13B depicts large adherent flat cells with irregular shape and extensions, derived from SMS cells cultured in a 6 well plate in an inductive medium (100×; bar=60 μm).
Figure 13C:
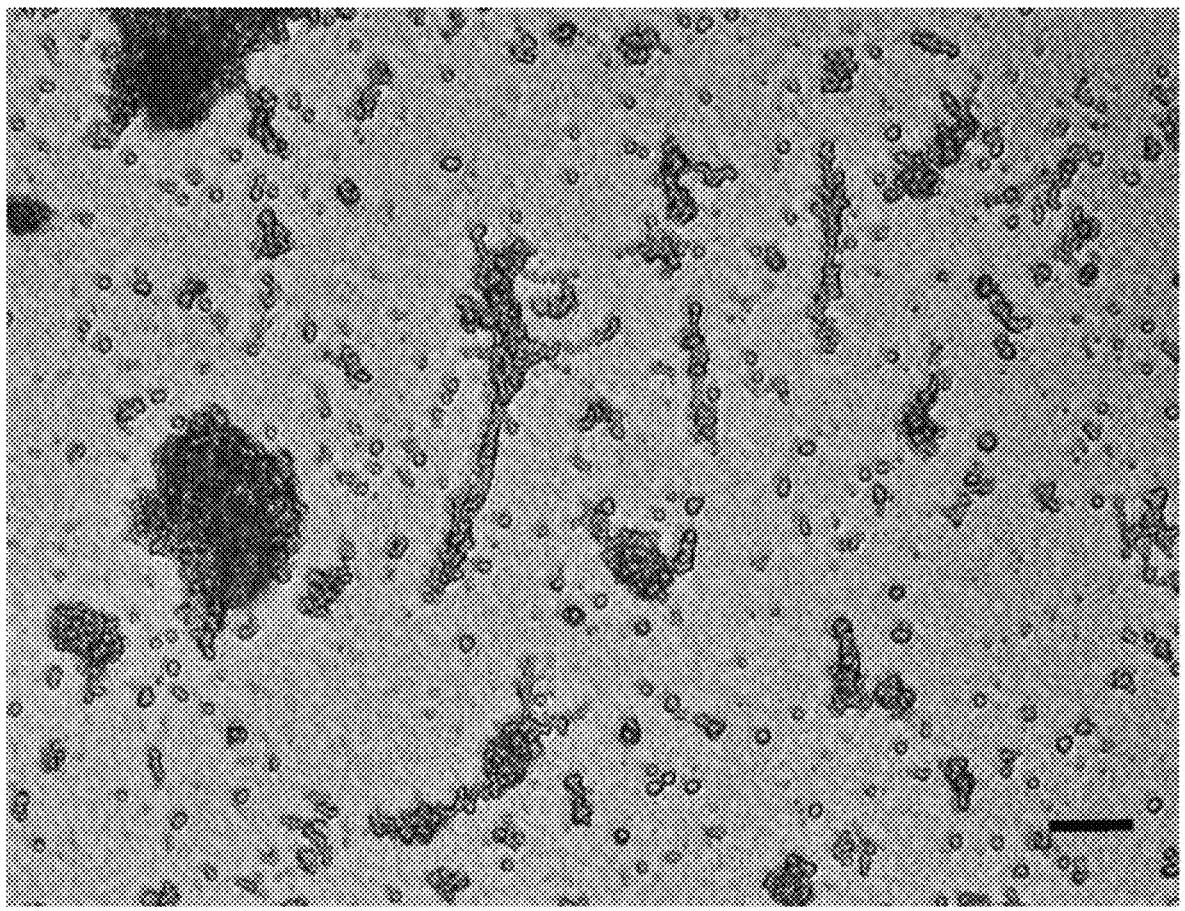
FIG. 13C depicts large adherent flat cells with irregular shape and extensions, derived from SMS cells cultured in a 6 well plate in an inductive medium (200×; bar=30 μm).

SMS cells grown in suspension, were washed twice using the basal medium MesenPRO™ (Gibco, catalog N: 127747-010). The cells were incubated in a 6 wells culture plate (TPP catalog N: 92406), at 5% $CO_2$ 37° C. and maximal humidity using the basal medium MesenPRO™ (Gibco, catalog N: 127747-010). SMS cells adhered to the plate, and gradually exhibited morphological changes resulting in enlarged cells (FIGS. 8B and 8C).

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of suspension culturing a population of small mobile stem (SMS) cells, comprising:
   culturing an isolated population of SMS cells in a vessel configured to promote the growth of SMS cells in a suspension, wherein the vessel is a polypropylene vessel or a pretreated siliconized vessel containing high glucose Dulbecco's Modified Eagle Medium (DMEM) comprising calf serum, thereby maintaining the isolated population of SMS cells in suspension in an undifferentiated state,
   wherein said SMS cells are adherent equi-dimensional cells with strict radial symmetry,
   wherein said SMS cells exhibit a translucent cytoplasm, and
   wherein the SMS cells are from 4.5 to 5.5 m in diameter and are highly mobile, and
   wherein the SMS cells are derived from umbilical cord, peripheral blood, bone marrow, or solid tissue.

2. The method of claim 1, wherein the vessel is a flask, container, chamber, channel, tube, niche, or bioreactor.

3. The method of claim 2, wherein at least a portion of a surface of the flask, container, chamber, channel, tube, niche, or bioreactor is etched.

4. The method of claim 3, wherein the at least a portion of the surface of the flask, container, chamber, channel, tube, niche, or bioreactor is etched with a geometric shape, a line, a web, a groove, a ridge or a curve.

5. The method of claim 2, wherein the channel is a microfluidic channel.

6. The method of claim 1, further comprising isolating or passaging the isolated population of SMS cells.

7. The method of claim 6, further comprising transfecting an isolated population of SMS cells with a gene that encodes a gene product.

8. The method of claim 7, further comprising isolating or purifying the gene product.

9. The method of claim 1, further comprising separating the isolated population of suspended SMS cells from adherent cells.

10. The method of claim 1, wherein the cells are cultured with movement or circulation of medium.

* * * * *